Figure 5:
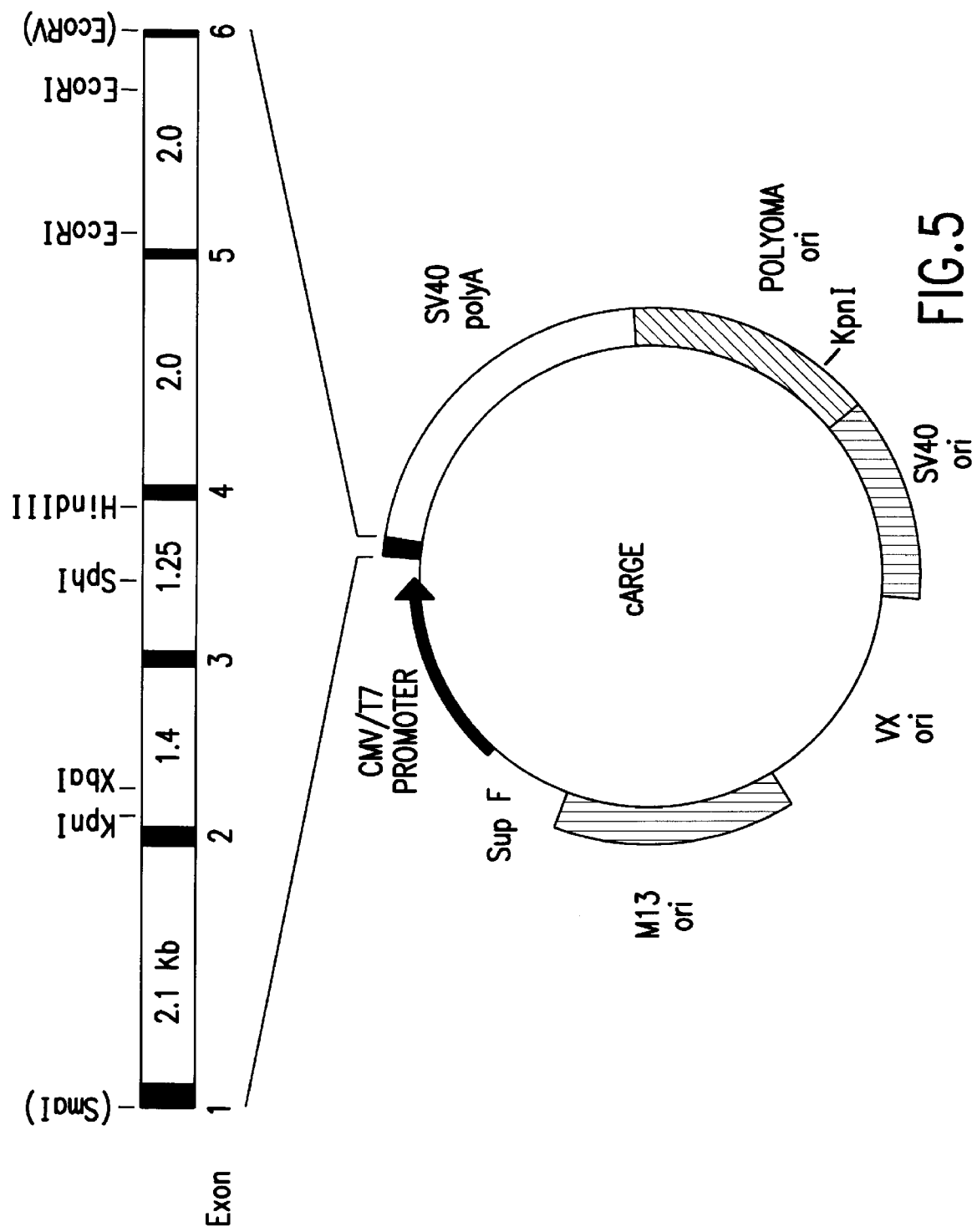

United States Patent [19]
Shoyab et al.

[11] Patent Number: 5,830,995
[45] Date of Patent: *Nov. 3, 1998

[54] FANPHIREGULINS: A FAMILY OF HEPARIN-BINDING EPITHELIAL CELL GROWTH FACTORS

[75] Inventors: Mohammed Shoyab, Seattle; Vicki Lynn McDonald, Kent, both of Wash.; James Garrett Bradley, Minnetonka, Minn.; Gregory D. Plowman, Seattle, Wash.

[73] Assignee: Bristol-Myers Squibb Company, New York, N.Y.

[ * ] Notice: The term of this patent shall not extend beyond the expiration date of Pat. No. 5,115,096.

[21] Appl. No.: 885,089

[22] Filed: May 18, 1992

Related U.S. Application Data

[63] Continuation-in-part of Ser. No. 297,816, Jan. 17, 1989, Pat. No. 5,115,096, which is a continuation-in-part of Ser. No. 181,884, Apr. 15, 1988, abandoned, which is a continuation-in-part of Ser. No. 148,327, Jan. 25, 1988, abandoned.

[51] Int. Cl.$^6$ .................................................. C07K 9/00
[52] U.S. Cl. ........................... 530/322; 530/324; 530/397
[58] Field of Search ................................. 530/322, 397, 530/324

[56] References Cited

U.S. PATENT DOCUMENTS 5,115,096  5/1992  Shoyab et al. ........................... 530/322

FOREIGN PATENT DOCUMENTS

89/0549  10/1989  South Africa .

OTHER PUBLICATIONS

Shoyab et al., "Amphiregulin: A bifunctional growth–modulating glycoprotein produced by the phorbol 12–myristate 13–acetate–treated human breast adenocarcinoma cell line MCF–7" 1988, Proc. Natl. Acad. Sci. 85:6528–6532.

Shoyab et al., "Structure and function of human Amphiregulin: A member of the Epidermal Growth Factor Family" 1989, Science 243:1074–76.

Plowman et al., "The amphiregulin gene encodes a novel epidermal growth factor–related protein with tumor–inhibiting activity" 1990, Molecular and Cellular Biology 10:1969–1981.

Kimura et al., "Structure, expression and function of a schwannoma–derived growth factor" 1990 Nature 348:257–260.

Todaro et al., "Cellular and viral ligands that interact with the EGF receptor" 1990, Seminars in Cancer Biology 1:257–263.

Higashiyama et al., "A heparin–binding growth factor secreted by macrophage–like cells that is related to EGF" 1991, Science 251:936–39.

Cook et al., "A heparin sulfate–regulated human keratinocyte autocrine factor is similar or Identical to Amphiregulin" 1991, Molecular and Cellular Biology 11:2547–2557.

Scott et al. (1983a) *Nature,* 302, 538–540.

Scott et al. (1983b) *Science,* 221, 236–240.

Ullrich et al. (1983) *Nature,* 303, 621–625.

Gray et al. (1983) *Nature,* 303, 722–725.

Brake et al. (1984) *Proc. Nat. Acad. Sci., USA,* 81, 4642–4646.

*Primary Examiner*—Jon P. Weber
*Attorney, Agent, or Firm*—Pennie & Edmonds LLP

[57] ABSTRACT

The present invention is directed to a family of heparin-binding epithelial cell growth factors termed amphiregulins (AR). In particular, it relates to the isolation of AR genes from different animal species, expression of the genes, identification of various forms of biologically active AR products, purification of the AR products, antibodies specific for AR, and uses of AR. AR is detectable in several normal human epithelial cells and in a high percentage of human colon cancers. In addition to stimulating the growth of these cultured epithelial cells, AR may have a wide range of applications including, but not limited to, accelerating the growth of normal epithelial cells. In some tumor cell lines, primarily of breast or ovarian carcinomas, AR serves as a direct growth inhibitor. On the other hand, AR may function as a growth stimulatory molecule in colorectal carcinomas and other pathologies of increased epithelial proliferation. In this regard AR may serve as a useful marker for disease staging and prognosis and reagents that specifically block AR may be of therapeutic use in controlling tumor cell growth and in disorders such as psoriasis.

12 Claims, 37 Drawing Sheets

AR. BOVINE cDNA SEQUENCE

```
                MetArgAlaProLeuLeuProProAlaProValValLeuSerLeuLeuIle
CTCTAGAACA ATGAGAGCCCCGCTGCTGCCGCCGGCGCCCGTGGTGCTGTCGCTCCTCAT          60

PheGlySerAlaHisTyrThrAlaGlyLeuAspValAsnAspThrTyrSerGlyLysGly
    CTTTGGCTCAGCCCATTATACTGCTGGATTAGACGTCAATGACACCTACTCTGGAAAAGG       120

GluProPheSerGlyAspHisSerAlaAspArgPheGluValThrSerArgSerGluIle
    GGAACCATTTTCTGGGGACCACAGTGCTGACAGATTTGAGGTGACCTCAAGAAGTGAGAT       180

SerSerAlaSerGluThrProProGlyGlyGluLeuSerSerValIleAspTyrAspTyr
    TTCCTCTGCAAGTGAAACGCCTCCTGGTGGCGAACTGTCCTCCGTGATCGACTATGACTA       240

AlaGluGluTyrAspAsnGluProGlnIleSerGlyTyrIleValAspAspSerValArg
    TGCAGAAGAGTATGATAATGAACCACAGATATCTGGCTATATTGTAGATGATTCAGTCAG       300

ValGluGlnValValLysProLysLysAsnLysThrGluSerGluLysThrSerAspLys
    AGTTGAACAGGTAGTTAAGCCTAAGAAAAACAAAACGGAAAGTGAAAAGACTTCAGATAA       360

ProLysArgLysLysLysGlyGlyLysAsnGlyLysAsnArgArgAsnArgLysLysLys
    ACCCAAGAGAAAGAAAAAGGGAGGCAAAAATGGAAAAAATAGAAGAAACAGAAAGAAGAA       420

AsnLeuCysAspThrGluPheGlnAsnPheCysIleHisGlyLysCysThrPheLeuGlu
    AAATCTGTGTGATACAGAATTTCAAAATTTCTGCATTCATGGAAAATGTACATTTTTAGA       480

GlnLeuGluThrValSerCysGlnCysTyrProGluTyrPheGlyGluArgCysGlyGlu
    GCAACTGGAAACAGTATCATGCCAATGTTATCCAGAGTACTTTGGTGAACGATGTGGGGA       540

LysSerMetLysThrGlnSerMetValAspSerAspLeuSerLysIleAlaLeuAlaAla
    AAAGTCCATGAAGACTCAGAGCATGGTCGACAGCGATTTATCAAAAATTGCTTTAGCAGC       600

IleAlaAlaPheValSerAlaMetThrPheThrAlaIleAlaValPheIleThrIleLeu
    TATAGCTGCTTTCGTCTCTGCCATGACCTTCACAGCTATTGCTGTTTTTATTACAATCCT       660

LeuArgArgArgCysLeuArgGlyTyrGluGlyValAlaGluGluArgLysLysLeuArg
    GCTTCGAAGACGATGCCTCAGGGGATATGAAGGTGTCGCTGAAGAACGAAAGAAACTTCG       720

GlnGluAsnGlyAsnAlaHisAlaValAla**
    ACAAGAAAATGGAAATGCACATGCTGTAGCATAACTGAAGGGTATCAGATCGGAGTCACT       780

GCCA                                                                 784
```

FIG.1A

AR, RAT cDNA CONSENSUS SEQUENCE

```
MetArgThrProSerLeuSerLeuAlaLeuSerValLeuSerLeuLeuValLeuGlySer
ATGAGAACTCCGTCGCTTTCGCTGGCGCTCTCAGTGCTGTCGCTGCTGGTCTTAGGCTCA                60

GlyHisTyrAlaAlaGlyLeuGluLeuAsnGlyThrSerSerGlyLysGlyGluProSer
GGCCATTATGCAGCTGGGTTGGAACTCAATGGCACCAGCTCTGGGAAAGGAGAACCGTCC                120

SerGlyAspHisSerAlaGlyGlyLeuValValSerGluValSerThrIleSerGluMet
TCTGGGGACCACAGTGCTGGTGGACTTGTGGTTTCTGAGGTCTCTACCATAAGCGAAATG                180

ProSerGlySerGluLeuSerThrGlyAspTyrAspTyrSerGluGluTyrAspAsnGlu
CCTTCTGGCAGTGAACTCTCCACAGGGGACTATGACTACTCGGAGGAGTATGATAACGAA                240

ProGlnIleSerGlyTyrIleValAspAspSerValArgValGluGlnValIleLysPro
CCACAAATATCCGGCTATATTGTGGACGACTCAGTCAGAGTTGAACAGGTGATTAAGCCT                300

LysGluAsnLysThrGluGlyGluLysSerSerGluLysProLysArgLysLysLysGly
AAGGAAAACAAGACAGAAGGAGAAAAGTCTTCAGAAAAACCCAAAAGAAAGAAAAAGGGA                360

GlyLysGlyGlyLysGlyArgArgAsnArgLysLysLysLysAsnProCysAlaAlaLys
GGCAAAGGCGGAAAAGGCAGAAGAAACAGGAAGAAGAAAAAGAATCCGTGTGCCGCCAAG                420

PheGlnAsnPheCysIleHisGlyGluCysArgTyrIleGluAsnLeuGluValValThr
TTTCAGAACTTCTGCATTCATGGTGAATGCAGATACATCGAGAACCTGGAGGTGGTGACC                480

CysHisCysHisGlnAspTyrPheGlyGluArgCysGlyGluLysThrMetLysThrGln
TGCCATTGTCATCAGGATTACTTTGGCGAACGGTGTGGAGAAAAAACCATGAAGACTCAG                540

LysLysAspAspSerAspLeuSerLysIleAlaLeuAlaAlaIleIleValPheValSer
AAGAAGGATGACAGCGACCTATCCAAGATCGCGTTAGCAGCCATAATTGTCTTTGTCTCC                600

AlaValSerValAlaAlaIleGlyIleIleThrAlaValLeuLeuArgLysArgPhePhe
GCCGTAAGCGTCGCAGCTATTGGCATCATTACCGCCGTCCTGCTTCGGAAACGATTCTTC                660

ArgGluTyrGluGluAlaGluGluArgArgArgLeuArgGlnGluAsnGlyThrAlaHis
AGGGAATATGAAGAAGCAGAGGAAAGAAGGAGGCTGCGGCAAGAAAACGGGACTGCACAT                720

AlaIleAla***
GCCATAGCCTAGCTGATGGC                                                         740
```

FIG. 1B

AR, MOUSE cDNA CONSENSUS SEQUENCE

```
MetArgThrProLeuLeuProLeuAlaArgSerValLeuLeuLeuLeuValLeuGlySer
ATGAGAACTCCGCTGCTACCGCTGGCGCGCTCAGTGCTGTTGCTGCTGGTCTTAGGCTCA          60

GlyHisTyrAlaAlaAlaLeuGluLeuAsnAspProSerSerGlyLysGlyGluSerLeu
GGCCATTATGCAGCTGCTTTGGAGCTCAATGACCCCAGCTCAGGGAAAGGCGAATCGCTT         120

SerGlyAspHisSerAlaGlyGlyLeuGluLeuSerValGlyArgGluValSerThrIle
TCTGGGGACCACAGTGCCGGTGGACTTGAGCTTTCTGTGGGAAGAGAGGTTTCCACCATA         180

SerGluMetProSerGlySerGluLeuSerThrGlyAspTyrAspTyrSerGluGluTyr
AGCGAAATGCCTTCTGGCAGTGAACTCTCCACAGGGGACTACGACTACTCAGAGGAGTAT         240

AspAsnGluProGlnIleSerGlyTyrIleIleAspAspSerValArgValGluGlnVal
GATAATGAACCACAAATATCCGGCTATATTATAGATGATTCAGTCAGAGTTGAACAGGTG         300

IleLysProLysLysAsnLysThrGluGlyGluLysSerThrGluLysProLysArgLys
ATTAAGCCCAAGAAAAACAAGACAGAAGGAGAAAAGTCTACAGAAAAACCCAAAAGGAAG         360

LysLysGlyGlyLysAsnGlyGluGlyArgArgAsnLysLysLysLysAsnProCysThr
AAAAAGGGAGGCAAAAATGGAGAAGGCAGAAGGAATAAGAAGAAAAAGAATCCATGCACT         420

AlaLysPheGlnAsnPheCysIleHisGlyGluCysArgTyrIleGluAsnLeuGluVal
GCCAAGTTTCAGAACTTTTGCATTCATGGCGAATGCAGATACATCGAGAACCTGGAGGTG         480

ValThrCysAsnCysHisGlnAspTyrPheGlyGluArgCysGlyGluLysSerMetLys
GTGACATGCAATTGTCATCAAGATTACTTTGGTGAACGGTGTGGAGAAAAATCCATGAAG         540

ThrHisSerGluAspAspLysAspLeuSerLysIleAlaValValAlaValThrIlePhe
ACTCACAGCGAGGATGACAAGGACCTATCCAAGATTGCAGTAGTAGCTGTCACTATCTTT         600

ValSerAlaIleIleLeuAlaAlaIleGlyIleGlyIleValIleThrValHisLeuTrp
GTCTCTGCCATCATCCTCGCAGCTATTGGCATCGGCATCGTTATCACAGTGCACCTTTGG         660

LysArgTyrPheArgGluTyrGluGlyGluThrGluGluArgArgArgLeuArgGlnGlu
AAACGATACTTCAGGGAATATGAAGGAGAAACAGAAGAAAGAAGGAGGCTTCGACAAGAA         720

AsnGlyThrValHisAlaIleAla***
AATGGGACTGTGCACGCCATTGCCTAGCTGAGGACAATGCAGGGTAAAAGTTGAATCATT         780

GCCAAGCCACACCGGAAATGACATTGGTCCTTCTTTCAGAAAAGGAAGTGGAGCTTTCGG         840

ATGGTTCCAGATGCCCAGTTGTCACTTTTTATGATAGTCTTACTTCTGTACATAAAGAGA         900

TGTGTGAAGATAAAATATTTTTTTCATGTTGTAAATAATTTATTTAATATTTAAGTGTTA         960

TTTATTTTATAGCTCATTAAACTTTTTTTAAACAAAAA                               998
```

FIG.1C

AMPHIREGULIN PRECURSOR
DEDUCED AMINO ACID SEQUENCE FORM CDNA CLONES

```
AR, human    MRAPLLPPAPVVLSLLILGSGHYAAGLDLNDTYSGKREPFSGDHSADGFE    50
AR, bovine   MRAPLLPPAPVVLSLLIFGSAHYTAGLDVNDTYSGKGEPFSGDHSADRFE    50
AR, rat      MRTPSLSLALSVLSLLVLGSGHYAAGLELNGTSSGKGEPSSGDHSAGGL-    49
AR, mouse    MRTPLLPLARSVLLLLVLGSGHYAAALELNDPSSGKGESLSGDHSAGGLE    50
             **.* *. * ** **..**.**.*.*..*.. *** *. ******. .

AR, human    VTSRSEMSSGSEISPVSEMPSSSEPSSGADYDYSEEYDNEPQIPGYIVDD    100
AR, bovine   VTSRSEISSASETPPGGEL------SSVIDYDYAEEYDNEPQISGYIVDD     94
AR, rat      --VVSEVSTISEMPSGSELSTG-------DYDYSEEYDNEPQISGYIVDD     90
AR, mouse    LSVGREVSTISEMPSGSELSTG-------DYDYSEEYDNEPQISGYIIDD     93
             .*.*. ** .. .*.          ****.*********.***.**
                              ↓

AR, human    SVRVEQVVKPPQNKTESENTSDKPKRKKKGGKNGKNRRNRKKK-NPCNAE    149
AR, bovine   SVRVEQVVKPKKNKTESEKTSDKPKRKKKGGKNGKNRRNRKKK-NLCDTE    143
AR, rat      SVRVEQVIKPKENKTEGEKSSEKPKRKKKGGKGGKGRRNRKKKKNPCAAK    140
AR, mouse    SVRVEQVIKPKKNKTEGEKSTEKPKRKKKGGKNGEGRRN-KKKKNPCTAK    142
             *******.** .****.*....***********.*..*** *** * *...
                                                              ↓

AR, human    FQNFCIHGECKYIEHLEAVTCKCQQEYFGERCGEKSMKTHSMIDSSLSKI    199
AR, bovine   FQNFCIHGKCTFLEQLETVSCQCYPEYFGERCGEKSMKTQSMVDSDLSKI    193
AR, rat      FQNFCIHGECRYIENLEVVTCHCHQDYFGERCGEKTMKTQKKDDSDLSKI    190
AR, mouse    FQNFCIHGECRYIENLEVVTCNCHQDYFGERCGEKSMKTHSEDDKDLSKI    192
             ********.* ..*.**.*.*.* ..*********.***.. *..****

AR, human    ALAAIAAFMSAVILTAVAV---ITVQLRRQYVRKYEGEAEERKKLRQENG    246
AR, bovine   ALAAIAAFVSAMTFTAIAV--FITILLRRRCLRGYEGVAEERKKLRQENG    241
AR, rat      ALAAIIVFVSAVSVAAIGI--ITAVLLRKRFFREYE-EAEERRRLRQENG    237
AR, mouse    AVVAVTIFVSAIILAAIGIGIVITVHLWKRYFREYEGETEERRRLRQENG    242
             *..*. *.**. .*...   ...*... * ** .***..******

AR, human    NVHAIA    252
AR, bovine   NAHAVA    247
AR, rat      TAHAIA    243
AR, mouse    TVHAIA    248
             ..**.*
```

FIG.2

AMPHIREGULIN GENE
EXON-INTRON JUNCTIONS

```
                        Exon 1 ↓ Exon 2
AR, human    MRAPLLPPAPVVLSLLILGSGHYAAGLDLNDTYSGKREPFSGDHSADGFE    50
AR, bovine   MRAPLLPPAPVVLSLLIFGSAHYTAGLDVNDTYSGKGEPFSGDHSADRFE    50
AR, mouse    MRTPLLPLARSVLLLLVLGSGHYAAALELNDPSSGKGESLSGDHSAGGLE    50
             **.**** * ** **..**.**.*.*..**. *** *. ******. .*

AR, human    VTSRSEMSSGSEISPVSEMPSSSEPSSGADYDYSEEYDNEPQIPGYIVDD    100
AR, bovine   VTSRSEISSASETPPGGEL------SSVIDYDYAEEYDNEPQISGYIVDD    94
AR, mouse    LSVGREVSTISEMPSGSELSTG-------DYDYSEEYDNEPQISGYIIDD    93
             .*.*. **  .. .*.          ****.*********.***.**

Exon 2 ↓ Exon 3
AR, human    SVRVEQVVKPPQNKTESENTSDKPKRKKKGGKNGKNRRNRKKK-NPCNAE    149
AR, bovine   SVRVEQVVKPKKNKTESEKTSDKPKRKKKGGKNGKNRRNRKKK-NLCDTE    143
AR, mouse    SVRVEQVIKPKKNKTEGEKSTEKPKRKKKGGKNGEGRRN-KKKKNPCTAK    142
             *******.** .****.*....*************..*** *** * *...

Exon 3 ↓ Exon 4
AR, human    FQNFCIHGECKYIEHLEAVTCKCQQEYFGERCGEKSMKTHSMIDSSLSKI    199
AR, bovine   FQNFCIHGKCTFLEQLETVSCQCYPEYFGERCGEKSMKTQSMVDSDLSKI    193
AR, mouse    FQNFCIHGECRYIENLEVVTCNCHQDYFGERCGEKSMKTHSEDDKDLSKI    192
             ********.* ..*.**.*.*.* ..*************.* *..****

Exon 4 ↓ Exon 5
AR, human    ALAAIAAFMSAVILTAVAV---ITVQLRRQYVRKYEGEAEERKKLRQENG    246
AR, bovine   ALAAIAAFVSAMTFTAIAV--FITILLRRRCLRGYEGVAEERKKLRQENG    241
AR, mouse    AVVAVTIFVSAIILAAIGIGIVITVHLWKRYFREYEGETEERRRLRQENG    242
             *..*. *.**. .*...    *.. *... * *** .***..******

AR, human    NVHAIA    252
AR, bovine   NAHAVA    247
AR, mouse    TVHAIA    248
             ..**.*
```

FIG.3

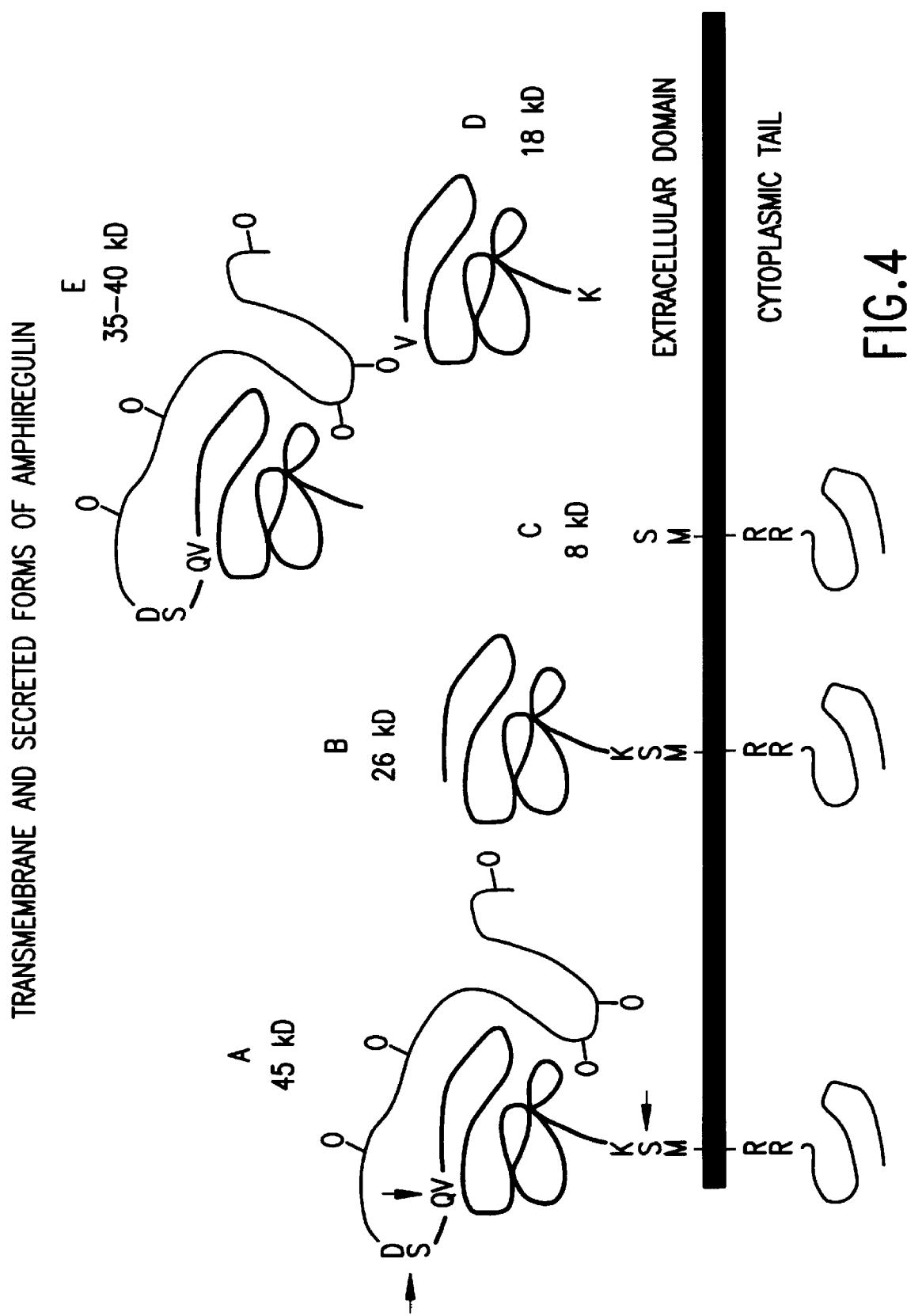

```
                    1              5             10              15             20              25             30             35              40             45
AR         C N A E F Q N F  C I M   - G E  C K Y I E H L E A V T  C K C Q Q E Y F G E R C  G E K S M K T H S
TGF-α        C P D S M T Q F  C F M   - G T  C R F L V Q E D K P A  C V C M S G Y Y G A R C  E M A D E L A V V
EGF          C P L S M D G Y  C L M   - D G V  C M Y I E A L D K Y A  C N C V V G Y I G E R C  Q Y R D L K W W E
VGF          C G P E G D G Y  C L M   - G D  C I M A R D I D G M Y  C R C S M G T T G I R C  Q M V V L V D Y Q 50              55             60             65             70             75             80              85
AR         M I D S S L S K - I A L A A I A A F M S A V - I L T A V A V I T Y Q L R R Q Y V R K
TGF-α      A A S Q K K Q A I T A L V V V S I V A L A V L I I T C V L I M C C Q V R K H C E W C
EGF        L R H A G H G Q Q Q K Y I V V A V C V V V L V M L L L S L W G A M Y Y R T Q K L L
VGF        R S E N P N T T T S Y I P S P G I M L V L V G I I I I T C C L L S V Y R F T R R T K
```

FIG. 9 pLMASMKT

```
                HpaI/DraI ***  ***  ***            LacSD           CroSD           BglII
CTGTTGGTTGGGGTAAGCGCAAAACCAGTTAAATAAGTAACACAGGAAACAGGATCACTAAGGAGGTTCAGATCT

Met Val Val Lys Pro Pro Gln Asn Lys Thr Glu Ser Glu Asn Thr Ser Asp Lys Pro Lys
ATG GTA GTT AAG CCC CCC CAA AAC AAG ACG GAA AGT GAA AAT ACT TCA GAT AAA CCC AAA

Arg Lys Lys Gly Gly Lys Asn Gly Lys Asn Arg Arg Asn Arg Lys Lys Asn Pro
AGA AAG AAA AAG GGA GGC AAA AAT GGA AAA AAT AGA AGA AAC AGA AAG AAA AAT CCA

Cys Asn Ala Glu Phe Gln Asn Phe Cys Ile His Gly Glu Cys Lys Tyr Ile Glu His Leu
TGT AAT GCA GAA TTT CAA AAT TTC TGC ATT CAC GGA GAA TGC AAA TAT ATA GAG CAC CTG

Glu Ala Val Thr Cys Lys Cys Gln Gln Glu Tyr Phe Gly Glu Arg Cys Gly Glu Lys Ser
GAA GCA GTA ACA TGC AAA TGT CAG CAA GAA TAT TTC GGT GAA CGG TGT GGG GAA AAG TCC

DraI/HpaI
Met Lys Thr ***  XbaI
ATG AAA ACT TAA TCTAGAGTCGATCCGTGACTAATTGGGACCCTAGAGTCCCCTTTTTATTTTAACCGCCCT
```

FIG. 25A pLMAAAT

```
                HpaI/DraI *** *** ***   LacSD       CroSD       BglII
CTGTTGGTTGGGGTAAGGCAAAACCAGTTAAATAAGTAACACAGGAAACAGGATCACTAAGGAGGTTCAGATCT

Met Val Val Lys Pro Pro Gln Asn Lys Thr Glu Ser Glu Asn Thr Ser Asp Lys Pro Lys
ATG GTA GTT AAG CCC CCC CAA AAC AAG ACG GAA AGT GAA AAT ACT TCA GAT AAA CCC AAA

Arg Lys Lys Lys Gly Gly Lys Asn Gly Lys Asn Arg Arg Asn Arg Lys Lys Lys Asn Pro
AGA AAG AAA AAG GGA GGC AAA AAT GGA AAA AAT AGA AAC AGA AAG AAA AAT CCA

Cys Asn Ala Glu Phe Gln Asn Phe Cys Ile His Gly Glu Cys Lys Tyr Ile Glu His Leu
TGT AAT GCA GAA TTT CAA AAT TTC TGC ATT CAC GGA GAA TGC AAA TAT ATA GAG CAC CTG

Glu Ala Val Thr Cys Lys Cys Gln Gln Glu Tyr Phe Gly Glu Arg Cys Gly Glu Lys Asp
GAA GCA GTA ACA TGC AAA TGT CAG CAA GAA TAT TTC GGT GAA CGG TGT GGG GAA AAG GAC

DraI/HpaI
Leu Leu Ala ***  XbaI
CTC CTG GCC TAA TCTAGAGTCGATCCGTGACTAATTGGGGACCCTAGAGGTCCCCTTTTTATTTTAACCGCCCT
```

FIG. 25B

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 784 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: CDS
        ( B ) LOCATION: 11..751

( x i ) SEQUENCE DESCRIPTION: SEQ ID NO:1:

```
CTCTAGAACA  ATG  AGA  GCC  CCG  CTG  CTG  CCG  CCG  GCG  CCC  GTG  GTG  CTG         4 9
            Met  Arg  Ala  Pro  Leu  Leu  Pro  Pro  Ala  Pro  Val  Val  Leu
             1             5                       10

TCG  CTC  CTC  ATC  TTT  GGC  TCA  GCC  CAT  TAT  ACT  GCT  GGA  TTA  GAC  GTC      9 7
Ser  Leu  Leu  Ile  Phe  Gly  Ser  Ala  His  Tyr  Thr  Ala  Gly  Leu  Asp  Val
 15                 20                            25
```

```
AAT GAC ACC TAC TCT GGA AAA GGG GAA CCA TTT TCT GGG GAC CAC AGT        145
Asn Asp Thr Tyr Ser Gly Lys Gly Glu Pro Phe Ser Gly Asp His Ser
 30              35                  40                  45

GCT GAC AGA TTT GAG GTG ACC TCA AGA AGT GAG ATT TCC TCT GCA AGT        193
Ala Asp Arg Phe Glu Val Thr Ser Arg Ser Glu Ile Ser Ser Ala Ser
             50                  55                  60

GAA ACG CCT CCT GGT GGC GAA CTG TCC TCC GTG ATC GAT TAT GAC TAT        241
Glu Thr Pro Pro Gly Gly Glu Leu Ser Ser Val Ile Asp Tyr Asp Tyr
         65                  70                  75

GCA GAA GAG TAT GAT AAT GAA CCA CAG ATA TCT GGC TAT ATT GTA GAT        289
Ala Glu Glu Tyr Asp Asn Glu Pro Gln Ile Ser Gly Tyr Ile Val Asp
             80                  85                  90

GAT TCA GTC AGA GTT GAA CAG GTA GTT AAG CCT AAG AAA AAC AAA ACG        337
Asp Ser Val Arg Val Glu Gln Val Val Lys Pro Lys Lys Asn Lys Thr
         95                 100                 105

GAA AGT GAA AAG ACT TCA GAT AAA CCC AAG AGA AAG AAA AAG GGA GGC        385
Glu Ser Glu Lys Thr Ser Asp Lys Pro Lys Arg Lys Lys Lys Gly Gly
110                 115                 120                 125

AAA AAT GGA AAA AAT AGA AGA AAC AGA AAG AAG AAA AAT CTG TGT GAT        433
Lys Asn Gly Lys Asn Arg Arg Asn Arg Lys Lys Lys Asn Leu Cys Asp
                130                 135                 140

ACA GAA TTT CAA AAT TTC TGC ATT CAT GGA AAA TGT ACA TTT TTA GAG        481
Thr Glu Phe Gln Asn Phe Cys Ile His Gly Lys Cys Thr Phe Leu Glu
            145                 150                 155

CAA CTG GAA ACA GTA TCA TGC CAA TGT TAT CCA GAG TAC TTT GGT GAA        529
Gln Leu Glu Thr Val Ser Cys Gln Cys Tyr Pro Glu Tyr Phe Gly Glu
        160                 165                 170

CGA TGT GGG GAA AAG TCC ATG AAG ACT CAG AGC ATG GTC GAC AGC GAT        577
Arg Cys Gly Glu Lys Ser Met Lys Thr Gln Ser Met Val Asp Ser Asp
    175                 180                 185

TTA TCA AAA ATT GCT TTA GCA GCT ATA GCT GCT TTC GTC TCT GCC ATG        625
Leu Ser Lys Ile Ala Leu Ala Ala Ile Ala Ala Phe Val Ser Ala Met
190                 195                 200                 205

ACC TTC ACA GCT ATT GCT GTT TTT ATT ACA ATC CTG CTT CGA AGA CGA        673
Thr Phe Thr Ala Ile Ala Val Phe Ile Thr Ile Leu Leu Arg Arg Arg
                210                 215                 220

TGC CTC AGG GGA TAT GAA GGT GTC GCT GAA GAA CGA AAG AAA CTT CGA        721
Cys Leu Arg Gly Tyr Glu Gly Val Ala Glu Glu Arg Lys Lys Leu Arg
            225                 230                 235

CAA GAA AAT GGA AAT GCA CAT GCT GTA GCA TAACTGAAGG GTATCAGATC          771
Gln Glu Asn Gly Asn Ala His Ala Val Ala
        240                 245

GGAGTCACTG CCA                                                         784

( 2 ) INFORMATION FOR SEQ ID NO:2:

( i ) SEQUENCE CHARACTERISTICS:
        ( A ) LENGTH: 247 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Arg Ala Pro Leu Leu Pro Pro Ala Pro Val Val Leu Ser Leu Leu
 1               5                  10                  15

Ile Phe Gly Ser Ala His Tyr Thr Ala Gly Leu Asp Val Asn Asp Thr
             20                  25                  30

Tyr Ser Gly Lys Gly Glu Pro Phe Ser Gly Asp His Ser Ala Asp Arg
         35                  40                  45
```

| Phe | Glu | Val | Thr | Ser | Arg | Ser | Glu | Ile | Ser | Ser | Ala | Ser | Glu | Thr | Pro |
| | 50 | | | | | 55 | | | | | 60 | | | | |

| Pro | Gly | Gly | Glu | Leu | Ser | Ser | Val | Ile | Asp | Tyr | Asp | Tyr | Ala | Glu | Glu |
| 65 | | | | | 70 | | | | | 75 | | | | | 80 |

| Tyr | Asp | Asn | Glu | Pro | Gln | Ile | Ser | Gly | Tyr | Ile | Val | Asp | Asp | Ser | Val |
| | | | | 85 | | | | | 90 | | | | | 95 | |

| Arg | Val | Glu | Gln | Val | Val | Lys | Pro | Lys | Asn | Lys | Thr | Glu | Ser | Glu |
| | | | 100 | | | | | 105 | | | | | 110 | |

| Lys | Thr | Ser | Asp | Lys | Pro | Lys | Arg | Lys | Lys | Lys | Gly | Gly | Lys | Asn | Gly |
| | | | 115 | | | | | 120 | | | | | 125 | | |

| Lys | Asn | Arg | Arg | Asn | Arg | Lys | Lys | Lys | Asn | Leu | Cys | Asp | Thr | Glu | Phe |
| | 130 | | | | | 135 | | | | | 140 | | | | |

| Gln | Asn | Phe | Cys | Ile | His | Gly | Lys | Cys | Thr | Phe | Leu | Glu | Gln | Leu | Glu |
| 145 | | | | | 150 | | | | | 155 | | | | | 160 |

| Thr | Val | Ser | Cys | Gln | Cys | Tyr | Pro | Glu | Tyr | Phe | Gly | Glu | Arg | Cys | Gly |
| | | | | 165 | | | | | 170 | | | | | 175 | |

| Glu | Lys | Ser | Met | Lys | Thr | Gln | Ser | Met | Val | Asp | Ser | Asp | Leu | Ser | Lys |
| | | | 180 | | | | | 185 | | | | | 190 | | |

| Ile | Ala | Leu | Ala | Ala | Ile | Ala | Ala | Phe | Val | Ser | Ala | Met | Thr | Phe | Thr |
| | | | 195 | | | | | 200 | | | | | 205 | | |

| Ala | Ile | Ala | Val | Phe | Ile | Thr | Ile | Leu | Leu | Arg | Arg | Arg | Cys | Leu | Arg |
| | 210 | | | | | 215 | | | | | 220 | | | | |

| Gly | Tyr | Glu | Gly | Val | Ala | Glu | Glu | Arg | Lys | Lys | Leu | Arg | Gln | Glu | Asn |
| 225 | | | | | 230 | | | | | 235 | | | | | 240 |

| Gly | Asn | Ala | His | Ala | Val | Ala |
| | | | | 245 | | |

(2) INFORMATION FOR SEQ ID NO:3:

(i) SEQUENCE CHARACTERISTICS:
        (A) LENGTH: 740 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: CDS
        (B) LOCATION: 1..729

(xi) SEQUENCE DESCRIPTION: SEQ ID NO:3:

| ATG | AGA | ACT | CCG | TCG | CTT | TCG | CTG | GCG | CTC | TCA | GTG | CTG | TCG | CTG | CTG | 48 |
| Met | Arg | Thr | Pro | Ser | Leu | Ser | Leu | Ala | Leu | Ser | Val | Leu | Ser | Leu | Leu | |
| | 250 | | | | | 255 | | | | | 260 | | | | | |

| GTC | TTA | GGC | TCA | GGC | CAT | TAT | GCA | GCT | GGG | TTG | GAA | CTC | AAT | GGC | ACC | 96 |
| Val | Leu | Gly | Ser | Gly | His | Tyr | Ala | Ala | Gly | Leu | Glu | Leu | Asn | Gly | Thr | |
| | 265 | | | | | 270 | | | | | 275 | | | | | |

| AGC | TCT | GGG | AAA | GGA | GAA | CCG | TCC | TCT | GGG | GAC | CAC | AGT | GCT | GGT | GGA | 144 |
| Ser | Ser | Gly | Lys | Gly | Glu | Pro | Ser | Ser | Gly | Asp | His | Ser | Ala | Gly | Gly | |
| 280 | | | | | 285 | | | | | 290 | | | | | 295 | |

| CTT | GTG | GTT | TCT | GAG | GTC | TCT | ACC | ATA | AGC | GAA | ATG | CCT | TCT | GGC | AGT | 192 |
| Leu | Val | Val | Ser | Glu | Val | Ser | Thr | Ile | Ser | Glu | Met | Pro | Ser | Gly | Ser | |
| | | | | 300 | | | | | 305 | | | | | 310 | | |

| GAA | CTC | TCC | ACA | GGG | GAC | TAT | GAC | TAC | TCG | GAG | GAG | TAT | GAT | AAC | GAA | 240 |
| Glu | Leu | Ser | Thr | Gly | Asp | Tyr | Asp | Tyr | Ser | Glu | Glu | Tyr | Asp | Asn | Glu | |
| | | | 315 | | | | | 320 | | | | | 325 | | | |

| CCA | CAA | ATA | TCC | GGC | TAT | ATT | GTG | GAC | GAC | TCA | GTC | AGA | GTT | GAA | CAG | 288 |
| Pro | Gln | Ile | Ser | Gly | Tyr | Ile | Val | Asp | Asp | Ser | Val | Arg | Val | Glu | Gln | |
| | | 330 | | | | | 335 | | | | | 340 | | | | |

| | | | | | | | | | | | | | | | | |
|---|---|---|---|---|---|---|---|---|---|---|---|---|---|---|---|---|
| GTG | ATT | AAG | CCT | AAG | GAA | AAC | AAG | ACA | GAA | GGA | GAA | AAG | TCT | TCA | GAA | 336 |
| Val | Ile | Lys | Pro | Lys | Glu | Asn | Lys | Thr | Glu | Gly | Glu | Lys | Ser | Ser | Glu | |
| | 345 | | | | 350 | | | | | 355 | | | | | | |
| AAA | CCC | AAA | AGA | AAG | AAA | AAG | GGA | GGC | AAA | GGC | GGA | AAA | GGC | AGA | AGA | 384 |
| Lys | Pro | Lys | Arg | Lys | Lys | Lys | Gly | Gly | Lys | Gly | Gly | Lys | Gly | Arg | Arg | |
| 360 | | | | | 365 | | | | | 370 | | | | | 375 | |
| AAC | AGG | AAG | AAG | AAA | AAG | AAT | CCG | TGT | GCC | GCC | AAG | TTT | CAG | AAC | TTC | 432 |
| Asn | Arg | Lys | Lys | Lys | Lys | Asn | Pro | Cys | Ala | Ala | Lys | Phe | Gln | Asn | Phe | |
| | | | | | 380 | | | | | 385 | | | | | 390 | |
| TGC | ATT | CAT | GGT | GAA | TGC | AGA | TAC | ATC | GAG | AAC | CTG | GAG | GTG | GTG | ACC | 480 |
| Cys | Ile | His | Gly | Glu | Cys | Arg | Tyr | Ile | Glu | Asn | Leu | Glu | Val | Val | Thr | |
| | | | 395 | | | | | 400 | | | | | 405 | | | |
| TGC | CAT | TGT | CAT | CAG | GAT | TAC | TTT | GGC | GAA | CGG | TGT | GGA | GAA | AAA | ACC | 528 |
| Cys | His | Cys | His | Gln | Asp | Tyr | Phe | Gly | Glu | Arg | Cys | Gly | Glu | Lys | Thr | |
| | | | 410 | | | | | 415 | | | | | 420 | | | |
| ATG | AAG | ACT | CAG | AAG | AAG | GAT | GAC | AGC | GAC | CTA | TCC | AAG | ATC | GCG | TTA | 576 |
| Met | Lys | Thr | Gln | Lys | Lys | Asp | Asp | Ser | Asp | Leu | Ser | Lys | Ile | Ala | Leu | |
| | 425 | | | | | 430 | | | | | 435 | | | | | |
| GCA | GCC | ATA | ATT | GTC | TTT | GTC | TCC | GCC | GTA | AGC | GTC | GCA | GCT | ATT | GGC | 624 |
| Ala | Ala | Ile | Ile | Val | Phe | Val | Ser | Ala | Val | Ser | Val | Ala | Ala | Ile | Gly | |
| 440 | | | | | 445 | | | | | 450 | | | | | 455 | |
| ATC | ATT | ACC | GCC | GTC | CTG | CTT | CGG | AAA | CGA | TTC | TTC | AGG | GAA | TAT | GAA | 672 |
| Ile | Ile | Thr | Ala | Val | Leu | Leu | Arg | Lys | Arg | Phe | Phe | Arg | Glu | Tyr | Glu | |
| | | | | 460 | | | | | 465 | | | | | 470 | | |
| GAA | GCA | GAG | GAA | AGA | AGG | AGG | CTG | CGG | CAA | GAA | AAC | GGG | ACT | GCA | CAT | 720 |
| Glu | Ala | Glu | Glu | Arg | Arg | Arg | Leu | Arg | Gln | Glu | Asn | Gly | Thr | Ala | His | |
| | | | 475 | | | | | 480 | | | | | 485 | | | |
| GCC | ATA | GCC | TAGCTGATGG | C | | | | | | | | | | | | 740 |
| Ala | Ile | Ala | | | | | | | | | | | | | | |
| | | 490 | | | | | | | | | | | | | | |

(2) INFORMATION FOR SEQ ID NO:4:

(i) SEQUENCE CHARACTERISTICS:
        (A) LENGTH: 243 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | | |
|---|---|---|---|---|---|---|---|---|---|---|---|---|---|---|---|
| Met | Arg | Thr | Pro | Ser | Leu | Ser | Leu | Ala | Leu | Ser | Val | Leu | Ser | Leu | Leu |
| 1 | | | | 5 | | | | | 10 | | | | | 15 | |
| Val | Leu | Gly | Ser | Gly | His | Tyr | Ala | Ala | Gly | Leu | Glu | Leu | Asn | Gly | Thr |
| | | | 20 | | | | | 25 | | | | | 30 | | |
| Ser | Ser | Gly | Lys | Gly | Glu | Pro | Ser | Ser | Gly | Asp | His | Ser | Ala | Gly | Gly |
| | | | 35 | | | | 40 | | | | | 45 | | | |
| Leu | Val | Val | Ser | Glu | Val | Ser | Thr | Ile | Ser | Glu | Met | Pro | Gly | Ser | Ser |
| | 50 | | | | | 55 | | | | | 60 | | | | |
| Glu | Leu | Ser | Thr | Gly | Asp | Tyr | Asp | Tyr | Ser | Glu | Tyr | Asp | Asn | Glu | |
| 65 | | | | | 70 | | | | 75 | | | | | 80 | |
| Pro | Gln | Ile | Ser | Gly | Tyr | Ile | Val | Asp | Asp | Ser | Val | Arg | Val | Glu | Gln |
| | | | | 85 | | | | | 90 | | | | | 95 | |
| Val | Ile | Lys | Pro | Lys | Glu | Asn | Lys | Thr | Glu | Gly | Glu | Lys | Ser | Ser | Glu |
| | | | | 100 | | | | 105 | | | | | 110 | | |
| Lys | Pro | Lys | Arg | Lys | Lys | Lys | Gly | Gly | Lys | Gly | Gly | Lys | Gly | Arg | Arg |
| | | | 115 | | | | | 120 | | | | | 125 | | |
| Asn | Arg | Lys | Lys | Lys | Lys | Asn | Pro | Cys | Ala | Ala | Lys | Phe | Gln | Asn | Phe |
| | | 130 | | | | | 135 | | | | | 140 | | | |
| Cys | Ile | His | Gly | Glu | Cys | Arg | Tyr | Ile | Glu | Asn | Leu | Glu | Val | Val | Thr |

| | | | | | 145 | | | | | 150 | | | | | 155 | | | | | 160 |
|---|---|---|---|---|---|---|---|---|---|---|---|---|---|---|---|---|---|---|---|---|
| Cys | His | Cys | His | Gln | | Asp | Tyr | Phe | Gly | | Glu | Arg | Cys | Gly | | Glu | Lys | Thr | | |
| | | | | 165 | | | | | | 170 | | | | | | 175 | | | | |

| Met | Lys | Thr | Gln | Lys | Lys | Asp | Asp | Ser | Asp | Leu | Ser | Lys | Ile | Ala | Leu |
|---|---|---|---|---|---|---|---|---|---|---|---|---|---|---|---|
| | | | 180 | | | | | 185 | | | | | 190 | | |

| Ala | Ala | Ile | Ile | Val | Phe | Val | Ser | Ala | Val | Ser | Val | Ala | Ala | Ile | Gly |
|---|---|---|---|---|---|---|---|---|---|---|---|---|---|---|---|
| | | | 195 | | | | 200 | | | | | 205 | | | |

| Ile | Ile | Thr | Ala | Val | Leu | Leu | Arg | Lys | Arg | Phe | Phe | Arg | Glu | Tyr | Glu |
|---|---|---|---|---|---|---|---|---|---|---|---|---|---|---|---|
| | 210 | | | | | 215 | | | | | 220 | | | | |

| Glu | Ala | Glu | Glu | Arg | Arg | Arg | Leu | Arg | Gln | Glu | Asn | Gly | Thr | Ala | His |
|---|---|---|---|---|---|---|---|---|---|---|---|---|---|---|---|
| 225 | | | | | 230 | | | | | 235 | | | | | 240 |

Ala Ile Ala ( 2 ) INFORMATION FOR SEQ ID NO:5:

( i ) SEQUENCE CHARACTERISTICS:
        ( A ) LENGTH: 998 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: CDS
        ( B ) LOCATION: 1..744

( x i ) SEQUENCE DESCRIPTION: SEQ ID NO:5:

| ATG | AGA | ACT | CCG | CTG | CTA | CCG | CTG | GCG | CGC | TCA | GTG | CTG | TTG | CTG | CTG | 48 |
|---|---|---|---|---|---|---|---|---|---|---|---|---|---|---|---|---|
| Met | Arg | Thr | Pro | Leu | Leu | Pro | Leu | Ala | Arg | Ser | Val | Leu | Leu | Leu | Leu | |
| 245 | | | | | 250 | | | | | 255 | | | | | | |

| GTC | TTA | GGC | TCA | GGC | CAT | TAT | GCA | GCT | GCT | TTG | GAG | CTC | AAT | GAC | CCC | 96 |
|---|---|---|---|---|---|---|---|---|---|---|---|---|---|---|---|---|
| Val | Leu | Gly | Ser | Gly | His | Tyr | Ala | Ala | Ala | Leu | Glu | Leu | Asn | Asp | Pro | |
| 260 | | | | | 265 | | | | | 270 | | | | | 275 | |

| AGC | TCA | GGG | AAA | GGC | GAA | TCG | CTT | TCT | GGG | GAC | CAC | AGT | GCC | GGT | GGA | 144 |
|---|---|---|---|---|---|---|---|---|---|---|---|---|---|---|---|---|
| Ser | Ser | Gly | Lys | Gly | Glu | Ser | Leu | Ser | Gly | Asp | His | Ser | Ala | Gly | Gly | |
| | | | 280 | | | | | 285 | | | | | 290 | | | |

| CTT | GAG | CTT | TCT | GTG | GGA | AGA | GAG | GTT | TCC | ACC | ATA | AGC | GAA | ATG | CCT | 192 |
|---|---|---|---|---|---|---|---|---|---|---|---|---|---|---|---|---|
| Leu | Glu | Leu | Ser | Val | Gly | Arg | Glu | Val | Ser | Thr | Ile | Ser | Glu | Met | Pro | |
| | | | 295 | | | | | 300 | | | | | 305 | | | |

| TCT | GGC | AGT | GAA | CTC | TCC | ACA | GGG | GAC | TAC | GAC | TAC | TCA | GAG | GAG | TAT | 240 |
|---|---|---|---|---|---|---|---|---|---|---|---|---|---|---|---|---|
| Ser | Gly | Ser | Glu | Leu | Ser | Thr | Gly | Asp | Tyr | Asp | Tyr | Ser | Glu | Glu | Tyr | |
| | | 310 | | | | | 315 | | | | | 320 | | | | |

| GAT | AAT | GAA | CCA | CAA | ATA | TCC | GGC | TAT | ATT | ATA | GAT | GAT | TCA | GTC | AGA | 288 |
|---|---|---|---|---|---|---|---|---|---|---|---|---|---|---|---|---|
| Asp | Asn | Glu | Pro | Gln | Ile | Ser | Gly | Tyr | Ile | Ile | Asp | Asp | Ser | Val | Arg | |
| | 325 | | | | | 330 | | | | | 335 | | | | | |

| GTT | GAA | CAG | GTG | ATT | AAG | CCC | AAG | AAA | AAC | AAG | ACA | GAA | GGA | GAA | AAG | 336 |
|---|---|---|---|---|---|---|---|---|---|---|---|---|---|---|---|---|
| Val | Glu | Gln | Val | Ile | Lys | Pro | Lys | Lys | Asn | Lys | Thr | Glu | Gly | Glu | Lys | |
| 340 | | | | | 345 | | | | | 350 | | | | | 355 | |

| TCT | ACA | GAA | AAA | CCC | AAA | AGG | AAG | AAA | AAG | GGA | GGC | AAA | AAT | GGA | GAA | 384 |
|---|---|---|---|---|---|---|---|---|---|---|---|---|---|---|---|---|
| Ser | Thr | Glu | Lys | Pro | Lys | Arg | Lys | Lys | Lys | Gly | Gly | Lys | Asn | Gly | Glu | |
| | | | | 360 | | | | | 365 | | | | | 370 | | |

| GGC | AGA | AGG | AAT | AAG | AAG | AAA | AAG | AAT | CCA | TGC | ACT | GCC | AAG | TTT | CAG | 432 |
|---|---|---|---|---|---|---|---|---|---|---|---|---|---|---|---|---|
| Gly | Arg | Arg | Asn | Lys | Lys | Lys | Lys | Asn | Pro | Cys | Thr | Ala | Lys | Phe | Gln | |
| | | | 375 | | | | | 380 | | | | | 385 | | | |

| AAC | TTT | TGC | ATT | CAT | GGC | GAA | TGC | AGA | TAC | ATC | GAG | AAC | CTG | GAG | GTG | 480 |
|---|---|---|---|---|---|---|---|---|---|---|---|---|---|---|---|---|
| Asn | Phe | Cys | Ile | His | Gly | Glu | Cys | Arg | Tyr | Ile | Glu | Asn | Leu | Glu | Val | |
| | | 390 | | | | | 395 | | | | | 400 | | | | |

| GTG | ACA | TGC | AAT | TGT | CAT | CAA | GAT | TAC | TTT | GGT | GAA | CGG | TGT | GGA | GAA | 528 |
|---|---|---|---|---|---|---|---|---|---|---|---|---|---|---|---|---|
| Val | Thr | Cys | Asn | Cys | His | Gln | Asp | Tyr | Phe | Gly | Glu | Arg | Cys | Gly | Glu | |
| | 405 | | | | | 410 | | | | | 415 | | | | | |

| | | | | | | | | | | | | | | | | |
|---|---|---|---|---|---|---|---|---|---|---|---|---|---|---|---|---|
| AAA | TCC | ATG | AAG | ACT | CAC | AGC | GAG | GAT | GAC | AAG | GAC | CTA | TCC | AAG | ATT | 576 |
| Lys | Ser | Met | Lys | Thr | His | Ser | Glu | Asp | Asp | Lys | Asp | Leu | Ser | Lys | Ile | |
| 420 | | | | | 425 | | | | 430 | | | | | | 435 | |
| GCA | GTA | GTA | GCT | GTC | ACT | ATC | TTT | GTC | TCT | GCC | ATC | ATC | CTC | GCA | GCT | 624 |
| Ala | Val | Val | Ala | Val | Thr | Ile | Phe | Val | Ser | Ala | Ile | Ile | Leu | Ala | Ala | |
| | | | | 440 | | | | | 445 | | | | | 450 | | |
| ATT | GGC | ATC | GGC | ATC | GTT | ATC | ACA | GTG | CAC | CTT | TGG | AAA | CGA | TAC | TTC | 672 |
| Ile | Gly | Ile | Gly | Ile | Val | Ile | Thr | Val | His | Leu | Trp | Lys | Arg | Tyr | Phe | |
| | | | 455 | | | | | 460 | | | | | 465 | | | |
| AGG | GAA | TAT | GAA | GGA | GAA | ACA | GAA | GAA | AGA | AGG | AGG | CTT | CGA | CAA | GAA | 720 |
| Arg | Glu | Tyr | Glu | Gly | Glu | Thr | Glu | Glu | Arg | Arg | Arg | Leu | Arg | Gln | Glu | |
| | | 470 | | | | 475 | | | | | 480 | | | | | |
| AAT | GGG | ACT | GTG | CAC | GCC | ATT | GCC | TAGCTGAGGA | | CAATGCAGGG | | TAAAAGTTGA | | | | 774 |
| Asn | Gly | Thr | Val | His | Ala | Ile | Ala | | | | | | | | | |
| 485 | | | | | 490 | | | | | | | | | | | |

ATCATTGCCA AGCCACACCG GAAATGACAT TGGTCCTTCT TTCAGAAAAG GAAGTGGAGC 834

TTTCGGATGG TTCCAGATGC CCAGTTGTCA CTTTTTATGA TAGTCTTACT TCTGTACATA 894

AAGAGATGTG TGAAGATAAA ATATTTTTT CATGTTGTAA ATAATTTATT TAATATTTAA 954

GTGTTATTTA TTTTATAGCT CATTAAACTT TTTTTAAACA AAAA 998

( 2 ) INFORMATION FOR SEQ ID NO:6:

( i ) SEQUENCE CHARACTERISTICS:
    ( A ) LENGTH: 248 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Arg | Thr | Pro | Leu | Leu | Pro | Leu | Ala | Arg | Ser | Val | Leu | Leu | Leu | Leu |
| 1 | | | | 5 | | | | 10 | | | | | 15 | | |
| Val | Leu | Gly | Ser | Gly | His | Tyr | Ala | Ala | Ala | Leu | Glu | Leu | Asn | Asp | Pro |
| | | | 20 | | | | | 25 | | | | 30 | | | |
| Ser | Ser | Gly | Lys | Gly | Glu | Ser | Leu | Ser | Gly | Asp | His | Ser | Ala | Gly | Gly |
| | | 35 | | | | | 40 | | | | | 45 | | | |
| Leu | Glu | Leu | Ser | Val | Gly | Arg | Glu | Val | Ser | Thr | Ile | Ser | Glu | Met | Pro |
| | 50 | | | | | 55 | | | | | 60 | | | | |
| Ser | Gly | Ser | Glu | Leu | Ser | Thr | Gly | Asp | Tyr | Asp | Tyr | Ser | Glu | Glu | Tyr |
| 65 | | | | | 70 | | | | 75 | | | | | | 80 |
| Asp | Asn | Glu | Pro | Gln | Ile | Ser | Gly | Tyr | Ile | Ile | Asp | Asp | Ser | Val | Arg |
| | | | | 85 | | | | | 90 | | | | | 95 | |
| Val | Glu | Gln | Val | Ile | Lys | Pro | Lys | Lys | Asn | Lys | Thr | Glu | Gly | Glu | Lys |
| | | | 100 | | | | 105 | | | | | 110 | | | |
| Ser | Thr | Glu | Lys | Pro | Lys | Arg | Lys | Lys | Lys | Gly | Gly | Lys | Asn | Gly | Glu |
| | | 115 | | | | | 120 | | | | | 125 | | | |
| Gly | Arg | Arg | Asn | Lys | Lys | Lys | Lys | Asn | Pro | Cys | Thr | Ala | Lys | Phe | Gln |
| | 130 | | | | | 135 | | | | | 140 | | | | |
| Asn | Phe | Cys | Ile | His | Gly | Glu | Cys | Arg | Tyr | Ile | Glu | Asn | Leu | Glu | Val |
| 145 | | | | | 150 | | | | | 155 | | | | | 160 |
| Val | Thr | Cys | Asn | Cys | His | Gln | Asp | Tyr | Phe | Gly | Glu | Arg | Cys | Gly | Glu |
| | | | | 165 | | | | | 170 | | | | | 175 | |
| Lys | Ser | Met | Lys | Thr | His | Ser | Glu | Asp | Asp | Lys | Asp | Leu | Ser | Lys | Ile |
| | | | 180 | | | | | 185 | | | | | 190 | | |
| Ala | Val | Val | Ala | Val | Thr | Ile | Phe | Val | Ser | Ala | Ile | Ile | Leu | Ala | Ala |
| | | | 195 | | | | | 200 | | | | | 205 | | |
| Ile | Gly | Ile | Gly | Ile | Val | Ile | Thr | Val | His | Leu | Trp | Lys | Arg | Tyr | Phe |

-continued

```
                       210                           215                           220
Arg  Glu  Tyr  Glu  Gly  Glu  Thr  Glu  Arg  Arg  Arg  Leu  Arg  Gln  Glu
225                      230                           235                           240

Asn  Gly  Thr  Val  His  Ala  Ile  Ala
                         245
```

( 2 ) INFORMATION FOR SEQ ID NO:7:

( i ) SEQUENCE CHARACTERISTICS:
        ( A ) LENGTH: 252 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:7:

```
Met  Arg  Ala  Pro  Leu  Leu  Pro  Pro  Ala  Pro  Val  Val  Leu  Ser  Leu  Leu
1                        5                           10                           15

Ile  Leu  Gly  Ser  Gly  His  Tyr  Ala  Ala  Gly  Leu  Asp  Leu  Asn  Asp  Thr
                         20                           25                           30

Tyr  Ser  Gly  Lys  Arg  Glu  Pro  Phe  Ser  Gly  Asp  His  Ser  Ala  Asp  Gly
                     35                           40                           45

Phe  Glu  Val  Thr  Ser  Arg  Ser  Glu  Met  Ser  Ser  Gly  Ser  Glu  Ile  Ser
             50                           55                           60

Pro  Val  Ser  Glu  Met  Pro  Ser  Ser  Glu  Pro  Ser  Ser  Gly  Ala  Asp
65                           70                           75                           80

Tyr  Asp  Tyr  Ser  Glu  Glu  Tyr  Asp  Asn  Glu  Pro  Gln  Ile  Pro  Gly  Tyr
                             85                           90                           95

Ile  Val  Asp  Asp  Ser  Val  Arg  Val  Glu  Gln  Val  Val  Lys  Pro  Pro  Gln
                         100                          105                          110

Asn  Lys  Thr  Glu  Ser  Glu  Asn  Thr  Ser  Asp  Lys  Pro  Lys  Arg  Lys  Lys
                     115                          120                          125

Lys  Gly  Gly  Lys  Asn  Gly  Lys  Asn  Arg  Arg  Asn  Arg  Lys  Lys  Lys  Asn
                 130                          135                          140

Pro  Cys  Asn  Ala  Glu  Phe  Gln  Asn  Phe  Cys  Ile  His  Gly  Glu  Cys  Lys
145                          150                          155                          160

Tyr  Ile  Glu  His  Leu  Glu  Ala  Val  Thr  Cys  Lys  Cys  Gln  Gln  Glu  Tyr
                         165                          170                          175

Phe  Gly  Glu  Arg  Cys  Gly  Glu  Lys  Ser  Met  Lys  Thr  His  Ser  Met  Ile
                     180                          185                          190

Asp  Ser  Ser  Leu  Ser  Lys  Ile  Ala  Leu  Ala  Ala  Ile  Ala  Ala  Phe  Met
                 195                          200                          205

Ser  Ala  Val  Ile  Leu  Thr  Ala  Val  Ala  Val  Ile  Thr  Val  Gln  Leu  Arg
             210                          215                          220

Arg  Gln  Tyr  Val  Arg  Lys  Tyr  Glu  Gly  Glu  Ala  Glu  Glu  Arg  Lys  Lys
225                          230                          235                          240

Leu  Arg  Gln  Glu  Asn  Gly  Asn  Val  His  Ala  Ile  Ala
                         245                          250
```

( 2 ) INFORMATION FOR SEQ ID NO:8:

( i ) SEQUENCE CHARACTERISTICS:
        ( A ) LENGTH: 247 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:8:

| Met | Arg | Ala | Pro | Leu | Leu | Pro | Pro | Ala | Pro | Val | Val | Leu | Ser | Leu | Leu |
|---|---|---|---|---|---|---|---|---|---|---|---|---|---|---|---|
| 1 | | | | 5 | | | | | 10 | | | | | 15 | |

| Ile | Phe | Gly | Ser | Ala | His | Tyr | Thr | Ala | Gly | Leu | Asp | Val | Asn | Asp | Thr |
|---|---|---|---|---|---|---|---|---|---|---|---|---|---|---|---|
| | | | 20 | | | | 25 | | | | | 30 | | | |

| Tyr | Ser | Gly | Lys | Gly | Glu | Pro | Phe | Ser | Gly | Asp | His | Ser | Ala | Asp | Arg |
|---|---|---|---|---|---|---|---|---|---|---|---|---|---|---|---|
| | | | 35 | | | | 40 | | | | | 45 | | | |

| Phe | Glu | Val | Thr | Ser | Arg | Ser | Glu | Ile | Ser | Ser | Ala | Ser | Glu | Thr | Pro |
|---|---|---|---|---|---|---|---|---|---|---|---|---|---|---|---|
| | 50 | | | | 55 | | | | | 60 | | | | | |

| Pro | Gly | Gly | Glu | Leu | Ser | Ser | Val | Ile | Asp | Tyr | Asp | Tyr | Ala | Glu | Glu |
|---|---|---|---|---|---|---|---|---|---|---|---|---|---|---|---|
| 65 | | | | | 70 | | | | | 75 | | | | | 80 |

| Tyr | Asp | Asn | Glu | Pro | Gln | Ile | Ser | Gly | Tyr | Ile | Val | Asp | Asp | Ser | Val |
|---|---|---|---|---|---|---|---|---|---|---|---|---|---|---|---|
| | | | | 85 | | | | | 90 | | | | | 95 | |

| Arg | Val | Glu | Gln | Val | Val | Lys | Pro | Lys | Lys | Asn | Lys | Thr | Glu | Ser | Glu |
|---|---|---|---|---|---|---|---|---|---|---|---|---|---|---|---|
| | | | 100 | | | | 105 | | | | | 110 | | | |

| Lys | Thr | Ser | Asp | Lys | Pro | Lys | Arg | Lys | Lys | Lys | Gly | Gly | Lys | Asn | Gly |
|---|---|---|---|---|---|---|---|---|---|---|---|---|---|---|---|
| | | | 115 | | | | 120 | | | | | 125 | | | |

| Lys | Asn | Arg | Arg | Asn | Arg | Lys | Lys | Asn | Leu | Cys | Asp | Thr | Glu | Phe |
|---|---|---|---|---|---|---|---|---|---|---|---|---|---|---|
| | 130 | | | | | 135 | | | | | 140 | | | |

| Gln | Asn | Phe | Cys | Ile | His | Gly | Lys | Cys | Thr | Phe | Leu | Glu | Gln | Leu | Glu |
|---|---|---|---|---|---|---|---|---|---|---|---|---|---|---|---|
| 145 | | | | | 150 | | | | | 155 | | | | | 160 |

| Thr | Val | Ser | Cys | Gln | Cys | Tyr | Pro | Glu | Tyr | Phe | Gly | Glu | Arg | Cys | Gly |
|---|---|---|---|---|---|---|---|---|---|---|---|---|---|---|---|
| | | | | 165 | | | | | 170 | | | | | 175 | |

| Glu | Lys | Ser | Met | Lys | Thr | Gln | Ser | Met | Val | Asp | Ser | Asp | Leu | Ser | Lys |
|---|---|---|---|---|---|---|---|---|---|---|---|---|---|---|---|
| | | | 180 | | | | | 185 | | | | | 190 | | |

| Ile | Ala | Leu | Ala | Ala | Ile | Ala | Ala | Phe | Val | Ser | Ala | Met | Thr | Phe | Thr |
|---|---|---|---|---|---|---|---|---|---|---|---|---|---|---|---|
| | | 195 | | | | | 200 | | | | | 205 | | | |

| Ala | Ile | Ala | Val | Phe | Ile | Thr | Ile | Leu | Leu | Arg | Arg | Arg | Cys | Leu | Arg |
|---|---|---|---|---|---|---|---|---|---|---|---|---|---|---|---|
| | 210 | | | | | 215 | | | | | 220 | | | | |

| Gly | Tyr | Glu | Gly | Val | Ala | Glu | Glu | Arg | Lys | Lys | Leu | Arg | Gln | Glu | Asn |
|---|---|---|---|---|---|---|---|---|---|---|---|---|---|---|---|
| 225 | | | | | 230 | | | | | 235 | | | | | 240 |

| Gly | Asn | Ala | His | Ala | Val | Ala |
|---|---|---|---|---|---|---|
| | | | | 245 | | |

( 2 ) INFORMATION FOR SEQ ID NO:9:

( i ) SEQUENCE CHARACTERISTICS:
        ( A ) LENGTH: 243 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:9:

| Met | Arg | Thr | Pro | Ser | Leu | Ser | Leu | Ala | Leu | Ser | Val | Leu | Ser | Leu | Leu |
|---|---|---|---|---|---|---|---|---|---|---|---|---|---|---|---|
| 1 | | | | 5 | | | | | 10 | | | | | 15 | |

| Val | Leu | Gly | Ser | Gly | His | Tyr | Ala | Ala | Gly | Leu | Glu | Leu | Asn | Gly | Thr |
|---|---|---|---|---|---|---|---|---|---|---|---|---|---|---|---|
| | | | 20 | | | | 25 | | | | | 30 | | | |

| Ser | Ser | Gly | Lys | Gly | Glu | Pro | Ser | Gly | Asp | His | Ser | Ala | Gly | Gly |
|---|---|---|---|---|---|---|---|---|---|---|---|---|---|---|
| | | | 35 | | | | 40 | | | | | 45 | | | |

| Leu | Val | Val | Ser | Glu | Val | Ser | Thr | Ile | Ser | Glu | Met | Pro | Ser | Gly | Ser |
|---|---|---|---|---|---|---|---|---|---|---|---|---|---|---|---|
| | 50 | | | | | 55 | | | | | 60 | | | | |

| Glu | Leu | Ser | Thr | Gly | Asp | Tyr | Asp | Tyr | Ser | Glu | Glu | Tyr | Asp | Asn | Glu |
|---|---|---|---|---|---|---|---|---|---|---|---|---|---|---|---|
| 65 | | | | | 70 | | | | | 75 | | | | | 80 |

| Pro | Gln | Ile | Ser | Gly | Tyr | Ile | Val | Asp | Asp | Ser | Val | Arg | Val | Glu | Gln |
|---|---|---|---|---|---|---|---|---|---|---|---|---|---|---|---|
| | | | | 85 | | | | | 90 | | | | | 95 | |

```
Val  Ile  Lys  Pro  Lys  Glu  Asn  Lys  Thr  Glu  Gly  Glu  Lys  Ser  Ser  Glu
               100                 105                      110

Lys  Pro  Lys  Arg  Lys  Lys  Gly  Gly  Lys  Gly  Gly  Lys  Gly  Arg  Arg
               115                 120                      125

Asn  Arg  Lys  Lys  Lys  Lys  Asn  Pro  Cys  Ala  Ala  Lys  Phe  Gln  Asn  Phe
          130                      135                 140

Cys  Ile  His  Gly  Glu  Cys  Arg  Tyr  Ile  Glu  Asn  Leu  Glu  Val  Val  Thr
145                      150                      155                           160

Cys  His  Cys  His  Gln  Asp  Tyr  Phe  Gly  Glu  Arg  Cys  Gly  Glu  Lys  Thr
                    165                      170                      175

Met  Lys  Thr  Gln  Lys  Lys  Asp  Asp  Ser  Asp  Leu  Ser  Lys  Ile  Ala  Leu
               180                      185                      190

Ala  Ala  Ile  Ile  Val  Phe  Val  Ser  Ala  Val  Ser  Val  Ala  Ala  Ile  Gly
               195                 200                      205

Ile  Ile  Thr  Ala  Val  Leu  Leu  Arg  Lys  Arg  Phe  Phe  Arg  Glu  Tyr  Glu
          210                      215                 220

Glu  Ala  Glu  Glu  Arg  Arg  Arg  Leu  Arg  Gln  Glu  Asn  Gly  Thr  Ala  His
225                      230                      235                           240

Ala  Ile  Ala
```

( 2 ) INFORMATION FOR SEQ ID NO:10:

( i ) SEQUENCE CHARACTERISTICS:
        ( A ) LENGTH: 248 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:10:

```
Met  Arg  Thr  Pro  Leu  Leu  Pro  Leu  Ala  Arg  Ser  Val  Leu  Leu  Leu  Leu
1                   5                    10                       15

Val  Leu  Gly  Ser  Gly  His  Tyr  Ala  Ala  Ala  Leu  Glu  Leu  Asn  Asp  Pro
               20                       25                       30

Ser  Ser  Gly  Lys  Gly  Glu  Ser  Leu  Ser  Gly  Asp  His  Ser  Ala  Gly  Gly
          35                       40                       45

Leu  Glu  Leu  Ser  Val  Gly  Arg  Glu  Val  Ser  Thr  Ile  Ser  Glu  Met  Pro
50                       55                       60

Ser  Gly  Ser  Glu  Leu  Ser  Thr  Gly  Asp  Tyr  Asp  Tyr  Ser  Glu  Glu  Tyr
65                       70                       75                       80

Asp  Asn  Glu  Pro  Gln  Ile  Ser  Gly  Tyr  Ile  Ile  Asp  Asp  Ser  Val  Arg
               85                       90                       95

Val  Glu  Gln  Val  Ile  Lys  Pro  Lys  Lys  Asn  Lys  Thr  Glu  Gly  Glu  Lys
               100                      105                      110

Ser  Thr  Glu  Lys  Pro  Lys  Arg  Lys  Lys  Lys  Gly  Gly  Lys  Asn  Gly  Glu
               115                      120                      125

Gly  Arg  Arg  Asn  Lys  Lys  Lys  Lys  Asn  Pro  Cys  Thr  Ala  Lys  Phe  Gln
          130                      135                      140

Asn  Phe  Cys  Ile  His  Gly  Glu  Cys  Arg  Tyr  Ile  Glu  Asn  Leu  Glu  Val
145                      150                      155                      160

Val  Thr  Cys  Asn  Cys  His  Gln  Asp  Tyr  Phe  Gly  Glu  Arg  Cys  Gly  Glu
                    165                      170                      175

Lys  Ser  Met  Lys  Thr  His  Ser  Glu  Asp  Asp  Lys  Asp  Leu  Ser  Lys  Ile
               180                      185                      190

Ala  Val  Val  Ala  Val  Thr  Ile  Phe  Val  Ser  Ala  Ile  Ile  Leu  Ala  Ala
```

|     | 195 |     |     |     | 200 |     |     |     | 205 |     |     |     |     |
| --- | --- | --- | --- | --- | --- | --- | --- | --- | --- | --- | --- | --- | --- |
| Ile | Gly | Ile | Gly | Ile | Val | Ile | Thr | Val | His | Leu | Trp | Lys | Arg | Tyr | Phe |
|     |     |     | 210 |     |     |     | 215 |     |     |     | 220 |     |     |     |
| Arg | Glu | Tyr | Glu | Gly | Glu | Thr | Glu | Glu | Arg | Arg | Arg | Leu | Arg | Gln | Glu |
| 225 |     |     |     |     | 230 |     |     |     | 235 |     |     |     |     | 240 |
| Asn | Gly | Thr | Val | His | Ala | Ile | Ala |
|     |     |     |     | 245 |

( 2 ) INFORMATION FOR SEQ ID NO:11:

( i ) SEQUENCE CHARACTERISTICS:
        ( A ) LENGTH: 85 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

| Cys | Asn | Ala | Glu | Phe | Gln | Asn | Phe | Cys | Ile | His | Gly | Glu | Cys | Lys | Tyr |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ile | Glu | His | Leu | Glu | Ala | Val | Thr | Cys | Lys | Cys | Gln | Gln | Glu | Tyr | Phe |
|     |     |     | 20 |     |     |     |     | 25 |     |     |     |     | 30 |     |     |
| Gly | Glu | Arg | Cys | Gly | Glu | Lys | Ser | Met | Lys | Thr | His | Ser | Met | Ile | Asp |
|     |     | 35 |     |     |     |     | 40 |     |     |     |     | 45 |     |     |     |
| Ser | Ser | Leu | Ser | Lys | Ile | Ala | Leu | Ala | Ala | Ile | Ala | Ala | Phe | His | Ser |
|     | 50 |     |     |     |     | 55 |     |     |     |     | 60 |     |     |     |     |
| Ala | Val | Ile | Leu | Thr | Ala | Val | Ala | Val | Ile | Thr | Val | Gln | Leu | Arg | Arg |
| 65 |     |     |     |     | 70 |     |     |     |     | 75 |     |     |     |     | 80 |
| Gln | Tyr | Val | Arg | Lys |
|     |     |     |     | 85 |

( 2 ) INFORMATION FOR SEQ ID NO:12:

( i ) SEQUENCE CHARACTERISTICS:
        ( A ) LENGTH: 87 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

| Cys | Pro | Asp | Ser | His | Thr | Gln | Phe | Cys | Phe | His | Gly | Thr | Cys | Arg | Phe |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Leu | Val | Gln | Glu | Asp | Lys | Pro | Ala | Cys | Val | Cys | His | Ser | Gly | Tyr | Val |
|     |     |     | 20 |     |     |     |     | 25 |     |     |     |     | 30 |     |     |
| Gly | Ala | Arg | Cys | Glu | His | Ala | Asp | Leu | Leu | Ala | Val | Val | Ala | Ala | Ser |
|     |     | 35 |     |     |     |     | 40 |     |     |     |     | 45 |     |     |     |
| Gln | Lys | Lys | Gln | Ala | Ile | Thr | Ala | Leu | Val | Val | Val | Ser | Ile | Val | Ala |
|     | 50 |     |     |     |     | 55 |     |     |     |     | 60 |     |     |     |     |
| Leu | Ala | Val | Leu | Ile | Ile | Thr | Cys | Val | Leu | Ile | His | Cys | Cys | Gln | Val |
| 65 |     |     |     |     | 70 |     |     |     |     | 75 |     |     |     |     | 80 |
| Arg | Lys | His | Cys | Glu | Trp | Cys |
|     |     |     |     | 85 |

( 2 ) INFORMATION FOR SEQ ID NO:13:

( i ) SEQUENCE CHARACTERISTICS:
        ( A ) LENGTH: 88 amino acids
        ( B ) TYPE: amino acid
        ( C ) STRANDEDNESS: single -continued (D) TOPOLOGY: linear (ii) MOLECULE TYPE: peptide (xi) SEQUENCE DESCRIPTION: SEQ ID NO:13:

| Cys | Pro | Leu | Ser | His | Asp | Gly | Tyr | Cys | Leu | His | Asp | Gly | Val | Cys | Met |
|---|---|---|---|---|---|---|---|---|---|---|---|---|---|---|---|
| 1 | | | | 5 | | | | | 10 | | | | | 15 | |

| Tyr | Ile | Glu | Ala | Leu | Asp | Lys | Tyr | Ala | Cys | Asn | Cys | Val | Val | Gly | Tyr |
|---|---|---|---|---|---|---|---|---|---|---|---|---|---|---|---|
| | | | 20 | | | | | 25 | | | | | 30 | | |

| Ile | Gly | Glu | Arg | Cys | Gln | Tyr | Arg | Asp | Leu | Lys | Trp | Trp | Glu | Leu | Arg |
|---|---|---|---|---|---|---|---|---|---|---|---|---|---|---|---|
| | | 35 | | | | | 40 | | | | | 45 | | | |

| His | Ala | Gly | His | Gly | Gln | Gln | Lys | Val | Ile | Val | Val | Ala | Val | Cys |
|---|---|---|---|---|---|---|---|---|---|---|---|---|---|---|
| | 50 | | | | 55 | | | | | 60 | | | | |

| Val | Val | Val | Leu | Val | Met | Leu | Leu | Leu | Leu | Ser | Leu | Trp | Gly | Ala | His |
|---|---|---|---|---|---|---|---|---|---|---|---|---|---|---|---|
| 65 | | | | | 70 | | | | | 75 | | | | | 80 |

| Tyr | Tyr | Arg | Thr | Gln | Lys | Leu | Leu |
|---|---|---|---|---|---|---|---|
| | | | | 85 | | | |

(2) INFORMATION FOR SEQ ID NO:14:

(i) SEQUENCE CHARACTERISTICS:
(A) LENGTH: 87 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:14:

| Cys | Gly | Pro | Glu | Gly | Asp | Gly | Tyr | Cys | Leu | His | Gly | Asp | Cys | Ile | His |
|---|---|---|---|---|---|---|---|---|---|---|---|---|---|---|---|
| 1 | | | | 5 | | | | | 10 | | | | | 15 | |

| Ala | Arg | Asp | Ile | Asp | Gly | Met | Tyr | Cys | Arg | Cys | Ser | His | Gly | Tyr | Thr |
|---|---|---|---|---|---|---|---|---|---|---|---|---|---|---|---|
| | | | 20 | | | | | 25 | | | | | 30 | | |

| Gly | Ile | Arg | Cys | Gln | His | Val | Val | Leu | Val | Asp | Tyr | Gln | Arg | Ser | Glu |
|---|---|---|---|---|---|---|---|---|---|---|---|---|---|---|---|
| | | 35 | | | | | 40 | | | | | 45 | | | |

| Asn | Pro | Asn | Thr | Thr | Thr | Ser | Tyr | Ile | Pro | Ser | Pro | Gly | Ile | Met | Leu |
|---|---|---|---|---|---|---|---|---|---|---|---|---|---|---|---|
| | 50 | | | | 55 | | | | | 60 | | | | | |

| Val | Leu | Val | Gly | Ile | Ile | Ile | Ile | Thr | Cys | Cys | Leu | Leu | Ser | Val | Tyr |
|---|---|---|---|---|---|---|---|---|---|---|---|---|---|---|---|
| 65 | | | | | 70 | | | | | 75 | | | | | 80 |

| Arg | Phe | Thr | Arg | Arg | Thr | Lys |
|---|---|---|---|---|---|---|
| | | | | 85 | | |

(2) INFORMATION FOR SEQ ID NO:15:

(i) SEQUENCE CHARACTERISTICS:
(A) LENGTH: 394 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 80..328

(xi) SEQUENCE DESCRIPTION: SEQ ID NO:15:

```
CTGTTGGTTG GGGTAAGCGC AAAACCAGTT AAATAAGTAA GTAACACAGG AAACAGGATC            60

ACTAAGGAGG TTCAGATCT ATG GTA GTT AAG CCC CCC CAA AAC AAG ACG GAA           112
                    Met Val Val Lys Pro Pro Gln Asn Lys Thr Glu
                        250                 255

AGT GAA AAT ACT TCA GAT AAA CCC AAA AGA AAG AAA AAG GGA GGC AAA            160
Ser Glu Asn Thr Ser Asp Lys Pro Lys Arg Lys Lys Lys Gly Gly Lys
```

```
                260                           265                           270                           275
AAT  GGA  AAA  AAT  AGA  AGA  AAC  AGA  AAG  AAG  AAA  AAT  CCA  TGT  AAT  GCA                      208
Asn  Gly  Lys  Asn  Arg  Arg  Asn  Arg  Lys  Lys  Lys  Asn  Pro  Cys  Asn  Ala
               280                           285                           290

GAA  TTT  CAA  AAT  TTC  TGC  ATT  CAC  GGA  GAA  TGC  AAA  TAT  ATA  GAG  CAC                      256
Glu  Phe  Gln  Asn  Phe  Cys  Ile  His  Gly  Glu  Cys  Lys  Tyr  Ile  Glu  His
               295                           300                           305

CTG  GAA  GCA  GTA  ACA  TGC  AAA  TGT  CAG  CAA  GAA  TAT  TTC  GGT  GAA  CGG                      304
Leu  Glu  Ala  Val  Thr  Cys  Lys  Cys  Gln  Gln  Glu  Tyr  Phe  Gly  Glu  Arg
          310                           315                           320

TGT  GGG  GAA  AAG  TCC  ATG  AAA  ACT  TAATCTAGAG TCGATCCGTG ACTAATTGGG                            358
Cys  Gly  Glu  Lys  Ser  Met  Lys  Thr
     325                           330

GACCCTAGAG GTCCCCTTTT TTATTTTAAC CGCCCT                                                              394
```

( 2 ) INFORMATION FOR SEQ ID NO:16:

( i ) SEQUENCE CHARACTERISTICS:
        ( A ) LENGTH: 83 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met  Val  Val  Lys  Pro  Pro  Gln  Asn  Lys  Thr  Glu  Ser  Glu  Asn  Thr  Ser
 1                    5                        10                        15

Asp  Lys  Pro  Lys  Arg  Lys  Lys  Lys  Gly  Gly  Lys  Asn  Gly  Lys  Asn  Arg
                20                        25                        30

Arg  Asn  Arg  Lys  Lys  Lys  Asn  Pro  Cys  Asn  Ala  Glu  Phe  Gln  Asn  Phe
           35                        40                        45

Cys  Ile  His  Gly  Glu  Cys  Lys  Tyr  Ile  Glu  His  Leu  Glu  Ala  Val  Thr
      50                        55                        60

Cys  Lys  Cys  Gln  Gln  Glu  Tyr  Phe  Gly  Glu  Arg  Cys  Gly  Glu  Lys  Ser
 65                       70                        75                        80

Met  Lys  Thr
```

( 2 ) INFORMATION FOR SEQ ID NO:17:

( i ) SEQUENCE CHARACTERISTICS:
        ( A ) LENGTH: 394 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 80..328

( x i ) SEQUENCE DESCRIPTION: SEQ ID NO:17:

```
CTGTTGGTTG GGGTAAGCGC AAAACCAGTT AAATAAGTAA GTAACACAGG AAACAGGATC                                    60

ACTAAGGAGG TTCAGATCT  ATG  GTA  GTT  AAG  CCC  CCC  CAA  AAC  AAG  ACG  GAA                         112
                     Met  Val  Val  Lys  Pro  Pro  Gln  Asn  Lys  Thr  Glu
                      85                                 90

AGT  GAA  AAT  ACT  TCA  GAT  AAA  CCC  AAA  AGA  AAG  AAA  AAG  GGA  GGC  AAA                     160
Ser  Glu  Asn  Thr  Ser  Asp  Lys  Pro  Lys  Arg  Lys  Lys  Lys  Gly  Gly  Lys
 95                      100                           105                           110

AAT  GGA  AAA  AAT  AGA  AGA  AAC  AGA  AAG  AAG  AAA  AAT  CCA  TGT  AAT  GCA                     208
Asn  Gly  Lys  Asn  Arg  Arg  Asn  Arg  Lys  Lys  Lys  Asn  Pro  Cys  Asn  Ala
               115                           120                           125
```

```
GAA  TTT  CAA  AAT  TTC  TGC  ATT  CAC  GGA  GAA  TGC  AAA  TAT  ATA  GAG  CAC        256
Glu  Phe  Gln  Asn  Phe  Cys  Ile  His  Gly  Glu  Cys  Lys  Tyr  Ile  Glu  His
               130                      135                     140

CTG  GAA  GCA  GTA  ACA  TGC  AAA  TGT  CAG  CAA  GAA  TAT  TTC  GGT  GAA  CGG        304
Leu  Glu  Ala  Val  Thr  Cys  Lys  Cys  Gln  Gln  Glu  Tyr  Phe  Gly  Glu  Arg
          145                      150                     155

TGT  GGG  GAA  AAG  GAC  CTC  CTG  GCC  TAATCTAGAG  TCGATCCGTG  ACTAATTGGG           358
Cys  Gly  Glu  Lys  Asp  Leu  Leu  Ala
     160                      165

GACCCTAGAG  GTCCCCTTTT  TTATTTTAAC  CGCCCT                                           394
```

( 2 ) INFORMATION FOR SEQ ID NO:18:

( i ) SEQUENCE CHARACTERISTICS:
        ( A ) LENGTH: 83 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Val  Val  Lys  Pro  Pro  Gln  Asn  Lys  Thr  Glu  Ser  Glu  Asn  Thr  Ser
 1                   5                        10                         15

Asp  Lys  Pro  Lys  Arg  Lys  Lys  Lys  Gly  Gly  Lys  Asn  Gly  Lys  Asn  Arg
               20                       25                      30

Arg  Asn  Arg  Lys  Lys  Lys  Asn  Pro  Cys  Asn  Ala  Glu  Phe  Gln  Asn  Phe
          35                       40                      45

Cys  Ile  His  Gly  Glu  Cys  Lys  Tyr  Ile  Glu  His  Leu  Glu  Ala  Val  Thr
     50                       55                      60

Cys  Lys  Cys  Gln  Gln  Glu  Tyr  Phe  Gly  Glu  Arg  Cys  Gly  Glu  Lys  Asp
65                       70                      75                       80

Leu  Leu  Ala
```

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Ser  Val  Arg  Val  Glu  Gln
 1                   5
```

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:20:

```
Asp  Thr  Tyr  Ser  Gly  Lys  Arg  Glu  Pro  Phe  Ser  Gly  Asp  His  Ser  Ala
 1                   5                        10                         15

Asp  Gly  Phe  Glu
               20
```

( 2 ) INFORMATION FOR SEQ ID NO:21:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:21:

Ser Ser Ser Glu Pro Ser Ser Gly Ala Asp Tyr Asp Tyr Ser Glu Glu
1               5                   10                  15

Tyr Asp Asn Glu
            20

( 2 ) INFORMATION FOR SEQ ID NO:22:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:22:

Val Asp Pro Pro Gln Asn Lys Thr Glu Ser Glu Asn Thr Ser Asp Lys
1               5                   10                  15

Pro Lys Arg Lys Lys Lys Gly
                20

( 2 ) INFORMATION FOR SEQ ID NO:23:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:23:

Asn Pro Cys Asn Ala Glu Phe Gln Asn Phe Cys Ile His Gly Glu Cys
1               5                   10                  15

Lys Tyr Ile Glu His Leu Glu Ala Val Thr Cys Lys Cys Gln Gln Glu
                20                  25                  30

Tyr Phe Gly Glu Arg Cys Gly Glu Lys
                35              40

( 2 ) INFORMATION FOR SEQ ID NO:24:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:24:

Lys Arg Lys Lys Lys
1               5

( 2 ) INFORMATION FOR SEQ ID NO:25:

( i ) SEQUENCE CHARACTERISTICS:
    ( A ) LENGTH: 8 amino acids
    ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:25:

Phe Gln Asn Phe Cys Ile His Gly
1               5

(2) INFORMATION FOR SEQ ID NO:26:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:26:

Pro Lys Arg Lys Lys Lys Gly
1               5

(2) INFORMATION FOR SEQ ID NO:27:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:27:

Lys Pro Lys Arg Lys Lys Lys Gly Gly Lys
1               5                   10

(2) INFORMATION FOR SEQ ID NO:28:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:28:

Asp Leu Leu Ala
1

(2) INFORMATION FOR SEQ ID NO:29:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:29:

Ser Met Lys Thr
1

(2) INFORMATION FOR SEQ ID NO:30:

(i) SEQUENCE CHARACTERISTICS:
(A) LENGTH: 78 amino acids
(B) TYPE: amino acid (C) STRANDEDNESS: single
(D) TOPOLOGY: unknown (i i) MOLECULE TYPE: protein (x i) SEQUENCE DESCRIPTION: SEQ ID NO:30:

| Val | Val | Lys | Pro | Lys | Lys | Asn | Lys | Thr | Glu | Ser | Glu | Lys | Thr | Ser | Asp |
|---|---|---|---|---|---|---|---|---|---|---|---|---|---|---|---|
| 1 | | | | 5 | | | | | 10 | | | | | 15 | |

| Lys | Pro | Lys | Arg | Lys | Lys | Lys | Gly | Gly | Lys | Asn | Gly | Lys | Asn | Arg | Arg |
|---|---|---|---|---|---|---|---|---|---|---|---|---|---|---|---|
| | | | 20 | | | | | 25 | | | | | 30 | | |

| Asn | Arg | Lys | Lys | Lys | Asn | Leu | Cys | Asp | Thr | Glu | Phe | Gln | Asn | Phe | Cys |
|---|---|---|---|---|---|---|---|---|---|---|---|---|---|---|---|
| | | 35 | | | | | 40 | | | | | 45 | | | |

| Ile | His | Gly | Lys | Cys | Thr | Phe | Leu | Glu | Gln | Leu | Glu | Thr | Val | Ser | Cys |
|---|---|---|---|---|---|---|---|---|---|---|---|---|---|---|---|
| | 50 | | | | | 55 | | | | | 60 | | | | |

| Gln | Cys | Tyr | Pro | Glu | Tyr | Phe | Gly | Glu | Arg | Cys | Gly | Glu | Lys |
|---|---|---|---|---|---|---|---|---|---|---|---|---|---|
| 65 | | | | | 70 | | | | | 75 | | | |

(2) INFORMATION FOR SEQ ID NO:31:

(i) SEQUENCE CHARACTERISTICS:
(A) LENGTH: 79 amino acids
(B) TYPE: amino acid
(C) STRANDEDNESS: single
(D) TOPOLOGY: unknown (i i) MOLECULE TYPE: protein (x i) SEQUENCE DESCRIPTION: SEQ ID NO:31:

| Val | Ile | Lys | Pro | Lys | Glu | Asn | Lys | Thr | Glu | Gly | Glu | Lys | Ser | Ser | Glu |
|---|---|---|---|---|---|---|---|---|---|---|---|---|---|---|---|
| 1 | | | | 5 | | | | | 10 | | | | | 15 | |

| Lys | Pro | Lys | Arg | Lys | Lys | Lys | Gly | Gly | Lys | Gly | Gly | Lys | Gly | Arg | Arg |
|---|---|---|---|---|---|---|---|---|---|---|---|---|---|---|---|
| | | | 20 | | | | | 25 | | | | | 30 | | |

| Asn | Arg | Lys | Lys | Lys | Lys | Asn | Pro | Cys | Ala | Ala | Lys | Phe | Gln | Asn | Phe |
|---|---|---|---|---|---|---|---|---|---|---|---|---|---|---|---|
| | | 35 | | | | | 40 | | | | | 45 | | | |

| Cys | Ile | His | Gly | Glu | Cys | Arg | Tyr | Ile | Glu | Asn | Leu | Glu | Val | Val | Thr |
|---|---|---|---|---|---|---|---|---|---|---|---|---|---|---|---|
| | 50 | | | | | 55 | | | | | 60 | | | | |

| Cys | His | Cys | His | Gln | Asp | Tyr | Phe | Gly | Glu | Arg | Cys | Gly | Glu | Lys |
|---|---|---|---|---|---|---|---|---|---|---|---|---|---|
| 65 | | | | | 70 | | | | | 75 | | | | |

(2) INFORMATION FOR SEQ ID NO:32:

(i) SEQUENCE CHARACTERISTICS:
(A) LENGTH: 78 amino acids
(B) TYPE: amino acid
(C) STRANDEDNESS: single
(D) TOPOLOGY: unknown (i i) MOLECULE TYPE: protein (x i) SEQUENCE DESCRIPTION: SEQ ID NO:32:

| Val | Ile | Lys | Pro | Lys | Lys | Asn | Lys | Thr | Glu | Gly | Glu | Lys | Ser | Thr | Glu |
|---|---|---|---|---|---|---|---|---|---|---|---|---|---|---|---|
| 1 | | | | 5 | | | | | 10 | | | | | 15 | |

| Lys | Pro | Lys | Arg | Lys | Lys | Lys | Gly | Gly | Lys | Asn | Gly | Glu | Gly | Arg | Arg |
|---|---|---|---|---|---|---|---|---|---|---|---|---|---|---|---|
| | | | 20 | | | | | 25 | | | | | 30 | | |

| Asn | Lys | Lys | Lys | Lys | Asn | Pro | Cys | Thr | Ala | Lys | Phe | Gln | Asn | Phe | Cys |
|---|---|---|---|---|---|---|---|---|---|---|---|---|---|---|---|
| | | 35 | | | | | 40 | | | | | 45 | | | |

| Ile | His | Gly | Glu | Cys | Arg | Tyr | Ile | Glu | Asn | Leu | Glu | Val | Val | Thr | Cys |
|---|---|---|---|---|---|---|---|---|---|---|---|---|---|---|---|
| | 50 | | | | | 55 | | | | | 60 | | | | |

| Asn | Cys | His | Gln | Asp | Tyr | Phe | Gly | Glu | Arg | Cys | Gly | Glu | Lys |
|---|---|---|---|---|---|---|---|---|---|---|---|---|---|
| 65 | | | | | 70 | | | | | 75 | | | | |

(2) INFORMATION FOR SEQ ID NO:33:

( i ) SEQUENCE CHARACTERISTICS:
    ( A ) LENGTH: 79 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
    ( A ) NAME/KEY: Modified-site
    ( B ) LOCATION: 78..79
    ( D ) OTHER INFORMATION: /note= "Where Xaa = X4 = carboxy
        terminal = Ser-Met-Lys-Thr or Asp-Leu-Leu..."

( x i ) SEQUENCE DESCRIPTION: SEQ ID NO:33:

```
Val Val Lys Pro Pro Gln Asn Lys Thr Glu Ser Glu Asn Thr Ser Asp
1               5                   10                  15

Lys Pro Lys Arg Lys Lys Lys Gly Gly Lys Asn Gly Lys Asn Arg Arg
                20                  25                  30

Asn Arg Lys Lys Lys Asn Pro Cys Asn Ala Glu Phe Gln Asn Phe Cys
            35                  40                  45

Ile His Gly Glu Cys Lys Tyr Ile Glu His Leu Glu Ala Val Thr Cys
        50                  55                  60

Lys Cys Gln Gln Glu Tyr Phe Gly Glu Arg Cys Gly Glu Lys Xaa
65                  70                  75
```

( 2 ) INFORMATION FOR SEQ ID NO:34:

( i ) SEQUENCE CHARACTERISTICS:
    ( A ) LENGTH: 158 amino acids
    ( B ) TYPE: amino acid
    ( C ) STRANDEDNESS: single
    ( D ) TOPOLOGY: unknown ( i i ) MOLECULE TYPE: protein ( x i ) SEQUENCE DESCRIPTION: SEQ ID NO:34:

```
Leu Asp Leu Asn Asp Thr Tyr Ser Gly Lys Arg Glu Pro Phe Ser Gly
1               5                   10                  15

Asp His Ser Ala Asp Gly Phe Glu Val Thr Ser Arg Ser Glu Met Ser
                20                  25                  30

Ser Gly Ser Glu Ile Ser Pro Val Ser Glu Met Pro Ser Ser Ser Glu
            35                  40                  45

Pro Ser Ser Gly Ala Asp Tyr Asp Tyr Ser Glu Glu Tyr Asp Asn Glu
        50                  55                  60

Pro Gln Ile Pro Gly Tyr Ile Val Asp Asp Ser Val Arg Val Glu Gln
65                  70                  75                  80

Val Val Lys Pro Pro Gln Asn Lys Thr Glu Ser Glu Asn Thr Ser Asp
                85                  90                  95

Lys Pro Lys Arg Lys Lys Lys Gly Gly Lys Asn Gly Lys Asn Arg Arg
                100                 105                 110

Asn Arg Lys Lys Lys Asn Pro Cys Asn Ala Glu Phe Gln Asn Phe Cys
            115                 120                 125

Ile His Gly Glu Cys Lys Tyr Ile Glu His Leu Glu Ala Val Thr Cys
        130                 135                 140

Lys Cys Gln Gln Glu Tyr Phe Gly Glu Arg Cys Gly Glu Lys
145                 150                 155
```

( 2 ) INFORMATION FOR SEQ ID NO:35:

( i ) SEQUENCE CHARACTERISTICS:
    ( A ) LENGTH: 226 amino acids (B) TYPE: amino acid
(C) STRANDEDNESS: single
(D) TOPOLOGY: unknown (ii) MOLECULE TYPE: protein (xi) SEQUENCE DESCRIPTION: SEQ ID NO:35:

```
Leu  Asp  Leu  Asn  Asp  Thr  Tyr  Ser  Gly  Lys  Arg  Glu  Pro  Phe  Ser  Gly
 1                   5                        10                       15
Asp  His  Ser  Ala  Asp  Gly  Phe  Glu  Val  Thr  Ser  Arg  Ser  Glu  Met  Ser
                20                       25                       30
Ser  Gly  Ser  Glu  Ile  Ser  Pro  Val  Ser  Glu  Met  Pro  Ser  Ser  Ser  Glu
           35                        40                       45
Pro  Ser  Ser  Gly  Ala  Asp  Tyr  Asp  Tyr  Ser  Glu  Glu  Tyr  Asp  Asn  Glu
      50                       55                       60
Pro  Gln  Ile  Pro  Gly  Tyr  Ile  Val  Asp  Asp  Ser  Val  Arg  Val  Glu  Gln
 65                       70                       75                       80
Val  Val  Lys  Pro  Pro  Gln  Asn  Lys  Thr  Glu  Ser  Glu  Asn  Thr  Ser  Asp
                85                       90                       95
Lys  Pro  Lys  Arg  Lys  Lys  Lys  Gly  Gly  Lys  Asn  Gly  Lys  Asn  Arg  Arg
               100                      105                      110
Asn  Arg  Lys  Lys  Lys  Asn  Pro  Cys  Asn  Ala  Glu  Phe  Gln  Asn  Phe  Cys
          115                      120                      125
Ile  His  Gly  Glu  Cys  Lys  Tyr  Ile  Glu  His  Leu  Glu  Ala  Val  Thr  Cys
          130                      135                      140
Lys  Cys  Gln  Gln  Glu  Tyr  Phe  Gly  Glu  Arg  Cys  Gly  Glu  Lys  Ser  Met
145                      150                      155                      160
Lys  Thr  His  Ser  Met  Ile  Asp  Ser  Ser  Leu  Ser  Lys  Ile  Ala  Leu  Ala
                     165                      170                      175
Ala  Ile  Ala  Ala  Phe  Met  Ser  Ala  Val  Ile  Leu  Thr  Ala  Val  Ala  Val
               180                      185                      190
Ile  Thr  Val  Gln  Leu  Arg  Arg  Gln  Tyr  Val  Arg  Lys  Tyr  Glu  Gly  Glu
          195                      200                      205
Ala  Glu  Glu  Arg  Lys  Lys  Leu  Arg  Gln  Glu  Asn  Gly  Asn  Val  His  Ala
     210                      215                      220
Ile  Ala
225
```

(2) INFORMATION FOR SEQ ID NO:36:

(i) SEQUENCE CHARACTERISTICS:
(A) LENGTH: 152 amino acids
(B) TYPE: amino acid
(C) STRANDEDNESS: single
(D) TOPOLOGY: unknown (ii) MOLECULE TYPE: protein (xi) SEQUENCE DESCRIPTION: SEQ ID NO:36:

```
Ser  Val  Arg  Val  Glu  Gln  Val  Val  Lys  Pro  Pro  Gln  Asn  Lys  Thr  Glu
 1                   5                        10                       15
Ser  Glu  Asn  Thr  Ser  Asp  Lys  Pro  Lys  Arg  Lys  Lys  Lys  Gly  Gly  Lys
                20                       25                       30
Asn  Gly  Lys  Asn  Arg  Arg  Asn  Arg  Lys  Lys  Lys  Asn  Pro  Cys  Asn  Ala
           35                       40                       45
Glu  Phe  Gln  Asn  Phe  Cys  Ile  His  Gly  Glu  Cys  Lys  Tyr  Ile  Glu  His
      50                       55                       60
Leu  Glu  Ala  Val  Thr  Cys  Lys  Cys  Gln  Gln  Glu  Tyr  Phe  Gly  Glu  Arg
 65                       70                       75                       80
```

-continued

| Cys | Gly | Glu | Lys | Ser 85 | Met | Lys | Thr | His | Ser 90 | Met | Ile | Asp | Ser | Ser 95 | Leu |
| Ser | Lys | Ile | Ala 100 | Leu | Ala | Ala | Ile | Ala 105 | Ala | Phe | Met | Ser | Ala 110 | Val | Ile |
| Leu | Thr | Ala 115 | Val | Ala | Val | Ile | Thr 120 | Val | Gln | Leu | Arg | Arg 125 | Gln | Tyr | Val |
| Arg | Lys 130 | Tyr | Glu | Gly | Glu | Ala 135 | Glu | Glu | Arg | Lys | Lys 140 | Leu | Arg | Gln | Glu |
| Asn 145 | Gly | Asn | Val | His | Ala 150 | Ile | Ala | | | | | | | | |

( 2 ) INFORMATION FOR SEQ ID NO:37:

( i ) SEQUENCE CHARACTERISTICS:
( A ) LENGTH: 146 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:37:

| Val 1 | Val | Lys | Pro | Pro 5 | Gln | Asn | Lys | Thr | Glu 10 | Ser | Glu | Asn | Thr | Ser 15 | Asp |
| Lys | Pro | Lys | Arg 20 | Lys | Lys | Lys | Gly | Gly 25 | Lys | Asn | Gly | Lys | Asn 30 | Arg | Arg |
| Asn | Arg | Lys 35 | Lys | Lys | Asn | Pro | Cys 40 | Asn | Ala | Glu | Phe | Gln 45 | Asn | Phe | Cys |
| Ile | His 50 | Gly | Glu | Cys | Lys | Tyr 55 | Ile | Glu | His | Leu | Glu 60 | Ala | Val | Thr | Cys |
| Lys 65 | Cys | Gln | Gln | Glu | Tyr 70 | Phe | Gly | Glu | Arg | Cys 75 | Gly | Glu | Lys | Ser | Met 80 |
| Lys | Thr | His | Ser | Met 85 | Ile | Asp | Ser | Ser | Leu 90 | Ser | Lys | Ile | Ala | Leu 95 | Ala |
| Ala | Ile | Ala | Ala 100 | Phe | Met | Ser | Ala | Val 105 | Ile | Leu | Thr | Ala | Val 110 | Ala | Val |
| Ile | Thr | Val 115 | Gln | Leu | Arg | Arg | Gln 120 | Tyr | Val | Arg | Lys | Tyr 125 | Glu | Gly | Glu |
| Ala | Glu 130 | Glu | Arg | Lys | Lys | Leu 135 | Arg | Gln | Glu | Asn | Gly 140 | Asn | Val | His | Ala |
| Ile 145 | Ala | | | | | | | | | | | | | | |

FANPHIREGULINS: A FAMILY OF HEPARIN-BINDING EPITHELIAL CELL GROWTH FACTORS

The present application is a continuation-in-part of copending application Ser. No. 297,816 filed Jan. 17, 1989, U.S. Pat. No. 5,115,096 which is a continuation-in-part of application Ser. No. 181,884 filed Apr. 15, 1988, abandoned, which is a continuation-in-part of application Ser. No. 148,327 filed Jan. 25, 1988, abandoned, each of which is incorporated by reference herein in its entirety.

1. INTRODUCTION

The present invention is directed to a family of heparin-binding epithelial cell growth factors termed amphiregulins (AR). In particular, it relates to the isolation of AR genes from different animal species, expression of the genes, identification of various forms of biologically active AR products, purification of the AR products, antibodies specific for AR, and uses of AR. AR is abundantly expressed in several normal human epithelial cells and in a high percentage of human colon carcinomas. In addition, AR stimulates the growth of a variety of epithelial cell lines in cultures. Therefore, AR may have a wide range of applications including, but not limited to, promoting the growth of epithelial cells. On the other hand, AR may also be used as a tumor marker for cancer diagnosis, and and as a target for therapies designed to control tumor cell growth.

2. BACKGROUND OF THE INVENTION

Cellular growth and differentiation appear to be initiated, promoted, maintained, and regulated by a multiplicity of stimulatory, inhibitory, and synergistic factors and hormones. The alteration and/or breakdown of the cellular homeostasis mechanism seems to be a fundamental cause of growth related diseases, including neoplasia. Growth modulatory factors are implicated in a wide variety of pathological and physiological processes including signal transduction, cell communication, growth and development, embryogenesis, immune response, hematopoiesis, cell survival and differentiation, inflammation, tissue repair and remodeling, atheroscleorosis and cancer. Justifiably, there is a great deal of interest in isolating, characterizing, and defining the functional mechanisms of growth modulatory factors because of their potential use in the diagnosis, prognosis, and treatment of cancer. Moreover, acquiring knowledge of these factors will aid in the understanding of the basic mechanisms behind normal growth control and the loss thereof in cancer cells.

Epidermal growth factor (EGF), transforming growth factor-α (TGFα), platelet-derived growth factor (PDGF), fibroblast growth factor (FGF), nerve growth factor (NGF), transforming growth factor-β (TGFβ), insulin growth factor I and II (IGF I, IGF II), hematopoietic growth factors such as erythropoietin, colony stimulating factors (CSF 1 and 2), interleukins (IL-1 to 6), interferons (IFN α, β, γ), tumor necrosis factor α and β (TNF α, β) leukoregulin, oncostatin M, and other less defined factors are growth and differentiation modulatory proteins produced by a variety of cell types either under normal physiological conditions or in response to exogenous stimuli. Most of these factors appear to act in autocrine and paracrine fashions. (For reviews see: Goustin, et al., 1986, Cancer Res. 46: 1015–1029; Rozengurt, 1986, Science 234: 161–66; Pardee, 1987, Cancer Res. 47: 1488–1491; Sachs, 1986, Sci. Amer. 254: 40–47; Marshall, 1987, Cell 50: 5–6; Melcher and Anderson, 1987, Cell 30: 715–720; Clemens and McNurlan, 1985, Biochem. J. 226: 345–360; Nathan, 1987, J. Clin. Invest. 79: 319–326; Sporn and Roberts, 1986, J. Clin. Invest. 78: 329–332; Old, 1987, Nature, 326: 330–331; Beutler and Cerami, 1987, New Eng. J. Med. 316: 379–385; Weinstein, J. Cell. Biochem., 33: 213–224; Zarling, et al., 1987, Proc. Natl. Acad. Sci. U.S.A. 83: 9739–9744; Sporn and Todaro, 1985, N. Eng. J. Med. 303: 878–880; Sporn and Roberts, 1985, Nature 313:, 745–747).

3. SUMMARY OF THE INVENTION

The present invention relates to the amphiregulin gene family, the various biologically active forms of polypeptides coded therefor, antibodies specific for the polypeptides, a method for producing and purifying the polypeptides, methods for using the polypeptides as epithelial cell growth factors, as well as methods for detecting and removing amphiregulin gene products for diagnosis and therapy of certain disease conditions including, but not limited to, cancer.

The invention is based, in part, on Applicants' discovery that the human nucleotide sequence encoding the bifunctional glycoprotein, amphiregulin (AR), can be used to isolate homologous nucleotide sequences from three other mammalian species, including bovine, mouse, and rat. In particular, all 4 AR genes share two stretches of complete identity in amino acid sequence, and one of such regions contains the heparin binding site. In addition, the exon organization of all 4 AR genes is identical.

Like other EGF-receptor binding proteins, all four AR peptides conserve the spacing of six cysteine residues in addition to other amino acid residues believed to be important for receptor binding or mitogenic activity. Unlike the other EGF-receptor binding proteins the four AR peptides lack a leucine residue on the carboxyl-terminal side of the sixth cystine residue. Addition of a leucine into a recombinant AR molecule markedly alters its affinity for the EGFR, whereas removal of this residue from EGF or TGF-α dramatically impairs their EGFR-binding capacity.

Eukaryotic expression of the complete AR coding sequences reveals a large transmembrane precursor protein in all 4 species. Further, several forms of soluble AR polypeptides and two additional membrane bound polypeptides are identified, which are generated by differential proteolytic processing. One soluble form of the product corresponds to the previously discovered 18–25 kD glycoprotein from TPA-treated MCF-7 cells, while the other soluble product is a larger 35–40 kD protein referred to as gp35 which contains an amino-terminal pro-region. Expression products of all 4 genes are biological active in stimulating EGF-receptor tyrosine phosphorylation, and in inducing proliferation of both human and mouse cells cultured in vitro suggesting that AR polypeptides are active across species barriers.

The two major secreted forms of AR display unique characteristics in binding to heparin and in having a net basic charge. A three-step procedure is devised based on these two AR properties for the large scale purification of AR from concentrated culture supernatants of eukaryotic cell lines expressing the AR coding sequence. Both the 18 kD and gp35 molecules can be purified to apparent homogeneity utilizing this procedure with retention of biological activities. Amino-terminal sequence determination of the two purified products revealed their precise start sites. The gp35 contains the smaller 18 kD polypeptide plus an additional amino-terminal pro-region which possesses potential glycosylation sites, glycosaminoglycan attachment sites, and tyrosine sulfate consensus motifs.

The biological activity of AR can be inhibited by heparin and various sulfated molecules. Therefore, it is possible that soluble, membrane-associated, or extracellular matrix-associated glycosaminoglycans can interact and regulate AR activities.

Prokaryotic expression of AR was accomplished by solubilization and refolding of recombinant AR from bacterial inclusion bodies. Efficient refolding of recombinant AR required conditions of high pH (11.0) and the inclusion of more than 3 amino acid residues following the sixth cysteine of AR. The "lead" bacterially produced AR protein (AR-SMKT) contains seven residues after the final cysteine, which are derived from the human AR precursor sequence. The unglycosylated expression products can be purified using cation exchange and heparin affinity columns, and are shown to be biologically active. The addition of a leucine residue to the carboxyl-terminal region end greatly increases AR binding affinity to the EGF receptor.

The expression products of the AR gene are shown to be stable in a number of formulations. Initial studies demonstrate variable release of AR from two carriers with a high recovery of biological activity. These studies confirm the feasibility of delivering AR in vivo for topical, parenteral, and oral applications.

Figure 11:
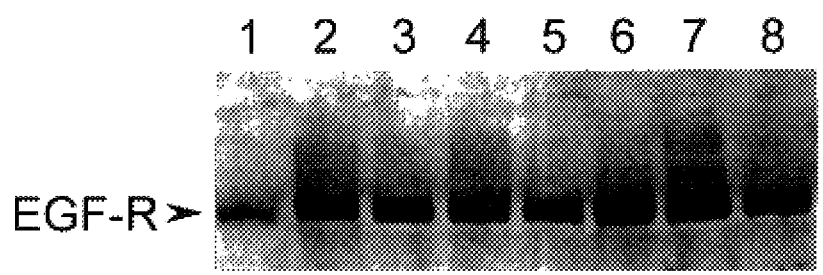

A panel of AR-specific monoclonal antibodies has been generated, some of which are capable of specifically neutralizing AR binding to the EGF-receptor. Antibodies have also been obtained which can differentiate AR from various species and can distinguish between the major soluble forms of AR.

AR stimulates the growth of a variety of normal epithelial cells, suggesting that it may be useful in accelerating normal epithelial proliferation including, but not limited to, colonic lesions. Additionally, AR may be a general regulator of epithelial cell growth, and is thereby capable of stimulating a wide range of epithelial stem cell populations. The removal of AR, by an antibody, heparin, peptide fragments small molecules, or soluble receptors may be of therapeutic value in the treatment of a variety of hyperproliferative disorders, including cancer. A high proportion of colorectal carcinoma cells express AR, indicating a potential role of AR in stimulating autocrine tumor growth. Therefore, AR may be useful as a tumor marker for clinical diagnosis.

The invention is described by way of examples in which AR genes from different species are cloned, their nucleotide sequences determined, their gene products expressed and purified, and the biochemical and biological properties of the gene products are fully characterized. A wide variety of uses for the various AR polypeptides are encompassed by the invention described herein.

4. BRIEF DESCRIPTION OF THE DRAWINGS

FIGS. 1A–1C. Nucleotide and deduced amino-acid sequence of: (A) cDNA clone pBoAR, encoding bovine amphiregulin (SEQ ID NO:1 AND SEQ ID NO:2), (B) cDNA clone pRatAR, encoding rat amphiregulin, (SEQ ID NOS:3 AND) 4) (C) cDNA clone pMAR, encoding mouse amphiregulin (SEQ ID NOS:5 AND 6).

FIG. 2. Alignment of the amino acid sequences of human (SEQ ID NO:8), bovine, rat (SEQ ID NOS:9), and mouse (SEQ ID NOS:10) amphiregulin. Asterisks represent residues conserved in all 4 species, dot represents conservation in 3 of the 4 species.

FIG. 3. Alignment of human, bovine, and mouse amphiregulin depicting location of exon-intron junctions.

FIG. 4. Schematic of multiple transmembrane and secreted forms of amphiregulin. (A) Transmembrane precursor following removal of signal sequence, (B) 26 kD transmembrane form following cleavage between precursor residues 100–107, (C) putative transmembrane fragment remaining after cleavage near juxtamembrane region (amino acids 184–198), (D) 18 kD form of soluble AR, (E) gp35, high molecular weight form of AR. Arrows mark predicted sites of proteolytic cleavage, unfilled circles represent potential sites of 0-linked glycosylation or glycosaminoglycanattachment sites.

FIG. 5. Schematic diagram of cARGE expression construct containing the human AR genomic coding sequence in the cDM8 vector.

FIG. 6. Location and sequence of peptide fragments in the human AR precursor used for (SEQ ID NOS:20, 21, 22 and 23) generating AR-specific immunoreagents.

FIG. 7A–7B. Immunoblot of recombinant AR from CHO cells. Supernatents from CHO/ARGE-2a cell supernatants (lane 1) or membrane preparations (lane 2) were separated on 10% SDS-PAGE and immunoblotted with anti-$AR_{108-130}$ (A) or anti-$AR_{71-90}$ (B) rabbit sera. $^{125}$I-Protein A was used as a second antibody and blots were exposed on a phosphorimager (Molecular Dynamics). Supernatants were dialyzed against, 1N acetic acid, and concentrated 10-fold prior to running 250 $\mu$l equivalent of original supernatants per lane. Molecular weight markers are shown on the left, arrowheads mark primary AR bands at 40–45 kD, 26 kD, and 18 kD.

FIG. 8A–8F. Immunogold localization of amphiregulin on MCF-7 breast carcinoma cells. MCF-7 cells were treated with TPA for 24 hrs, fixed, and AR was localized by indirect immunogold with silver enhancement for light microscopy using Mab 6R1C. Note the enrichment of AR on ruffled membranes at the cell margin (arrowheads a, b, c) and that the staining pattern often appears fibrillar (arrows a, b). Expression of membrane bound AR is polarized since specific regions of the membranes show enriched staining (arrowheads a, b, c) while adjacent areas are stained significantly less (open arrows a, c). Detergent extraction results in a loss of membrane staining, with cytoplasmic AR localized to a perinuclear, vesicular (arrow) compartment. Immunogold electron microscopy localized AR specifically to microspikes (arrows e, f), which were particularly abundant at points of cell contact (open arrow, e), and over the nucleus (f). Areas of smooth membrane were essentially unstained (arrowheads e, f).

FIG. 9. Amino acid alignment of the EGF-like motif and flanking transmembrane domain from three human (SEQ ID NOS: 11, 12 AND 13) proteins and one viral protein (SEQ ID NO:14) known to bind the EGF receptor. Alignment and numbering begins at the first cysteine of these motifs, and the most highly conserved residues are boxed. The putative transmembrane domains are underlined, and arrowheads mark the proteolytic cleavage sites where the mature growth factors are released from their membrane-bound precursors. Exon-intron boundaries are displayed as facing arrows situated above the interrupted amino acids. Vaccinia virus growth factor (VGF) contains no introns. Cleavage of the human AR precursor can also occur following position 42, 43, or 44 (see text).

FIG. 10A–10B. COS cells (mock transfected) (A) and COS/ARP (transfected with AR precursor expression plasmid) (B) 3 days after transfection. Note that cells expressing AR show the extensive aggregation and cytoplasmic extensions compared to the intact monolayer in mock transfected cells.

FIG. 11. EGF receptor tyrosine phosphorylation assay. Cells were stimulated for 10 min with the following recombinant molecules lane 1, media control; lane 2, human AR; lane 3, bovine AR; lane 4, rat AR; lane 5, mouse AR; lane 6, gp35; lane 7, EGF; lane 8, 293/ARP cells. The 175 kD tyrosine phosphorylated EGF-R was visualized by Western analysis with an antiphosphotyrosine antibody.

Figure 12:
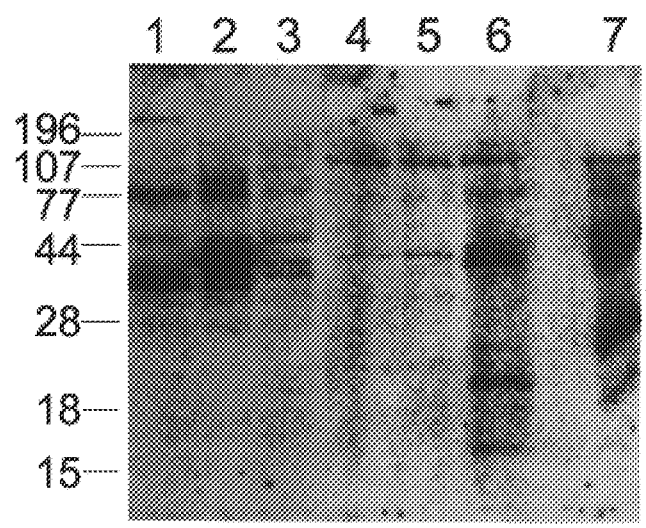

FIG. 12. Western analysis of membrane-associated forms of AR from several species. Membrane preparations from cells expressing recombinant mouse AR (lanes 1, 4), rat AR (lanes 2, 5), bovine AR (lanes 3, 6), or human AR (lane 7) were separated on by 10% SDS-PAGE and immunoblotted with anti-$AR_{108-130}$ (lanes 4–7) or anti-$AR_{71-90}$ (lanes 1–2).

Figure 13:
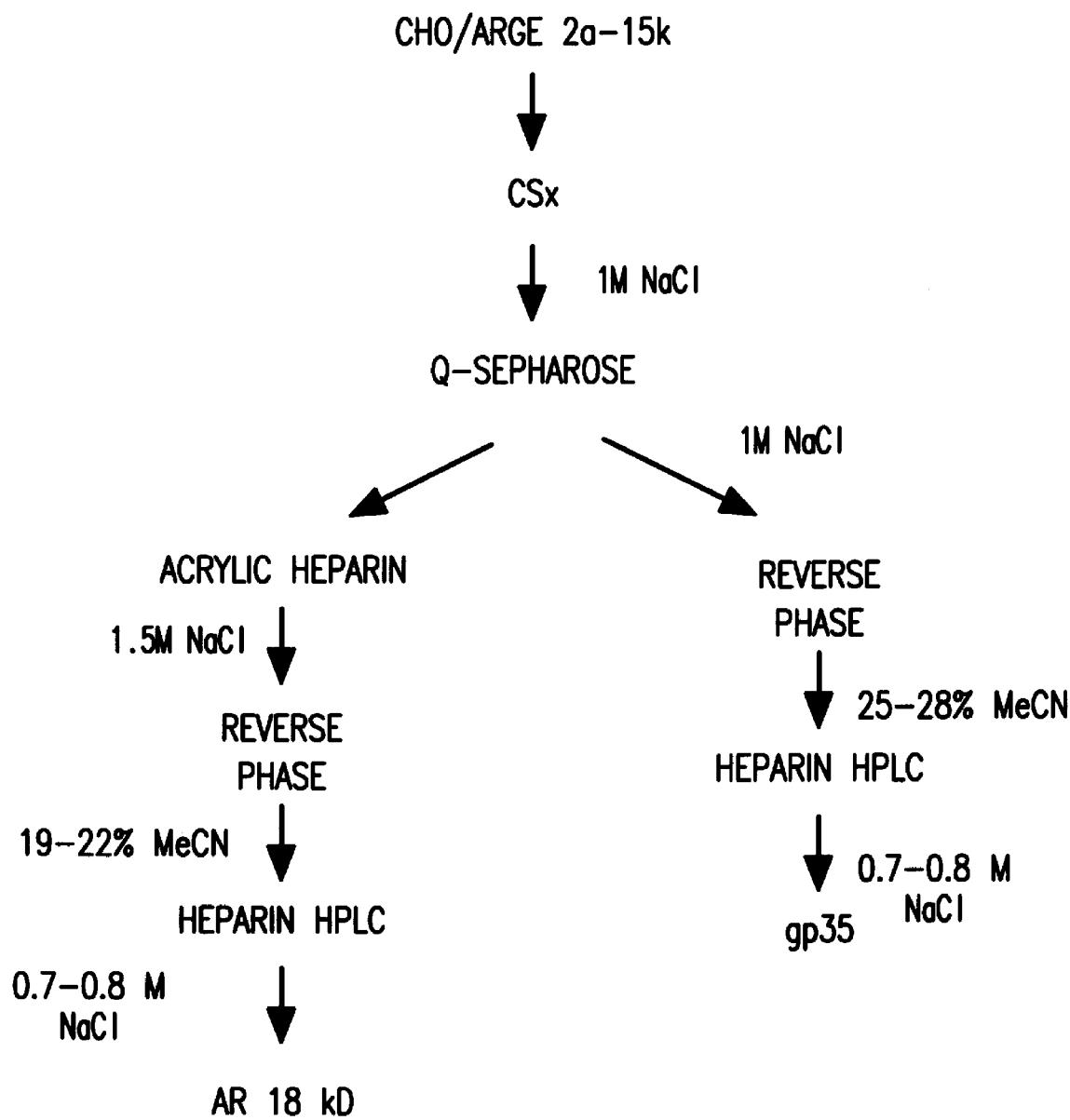

FIG. 13. Purificaton scheme for AR 18 kD and gp35 from recombinant CHO cells.

Figure 14:
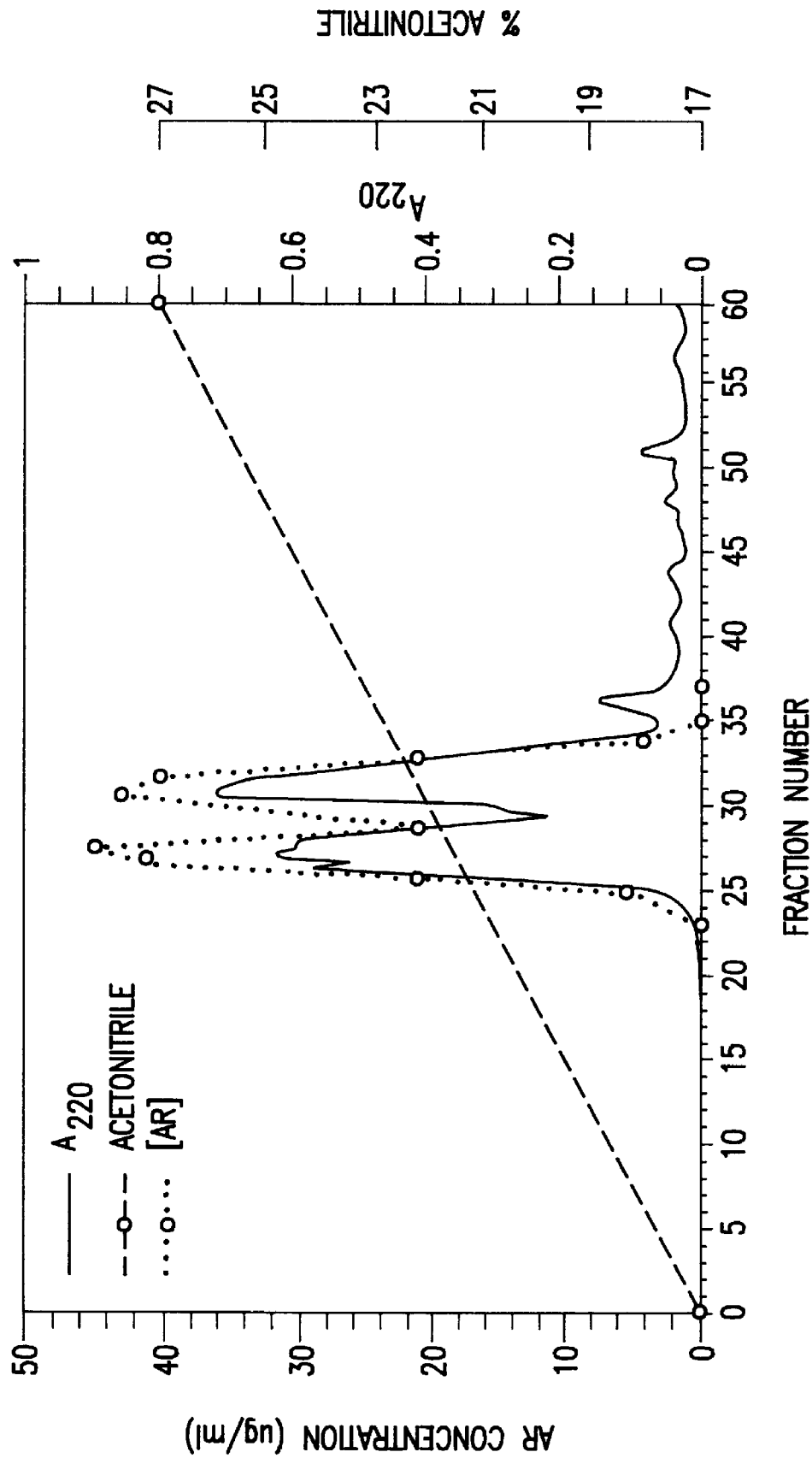

FIG. 14. Preparative reversed-phase HPLC of 18 kD form of AR.

Figure 15:
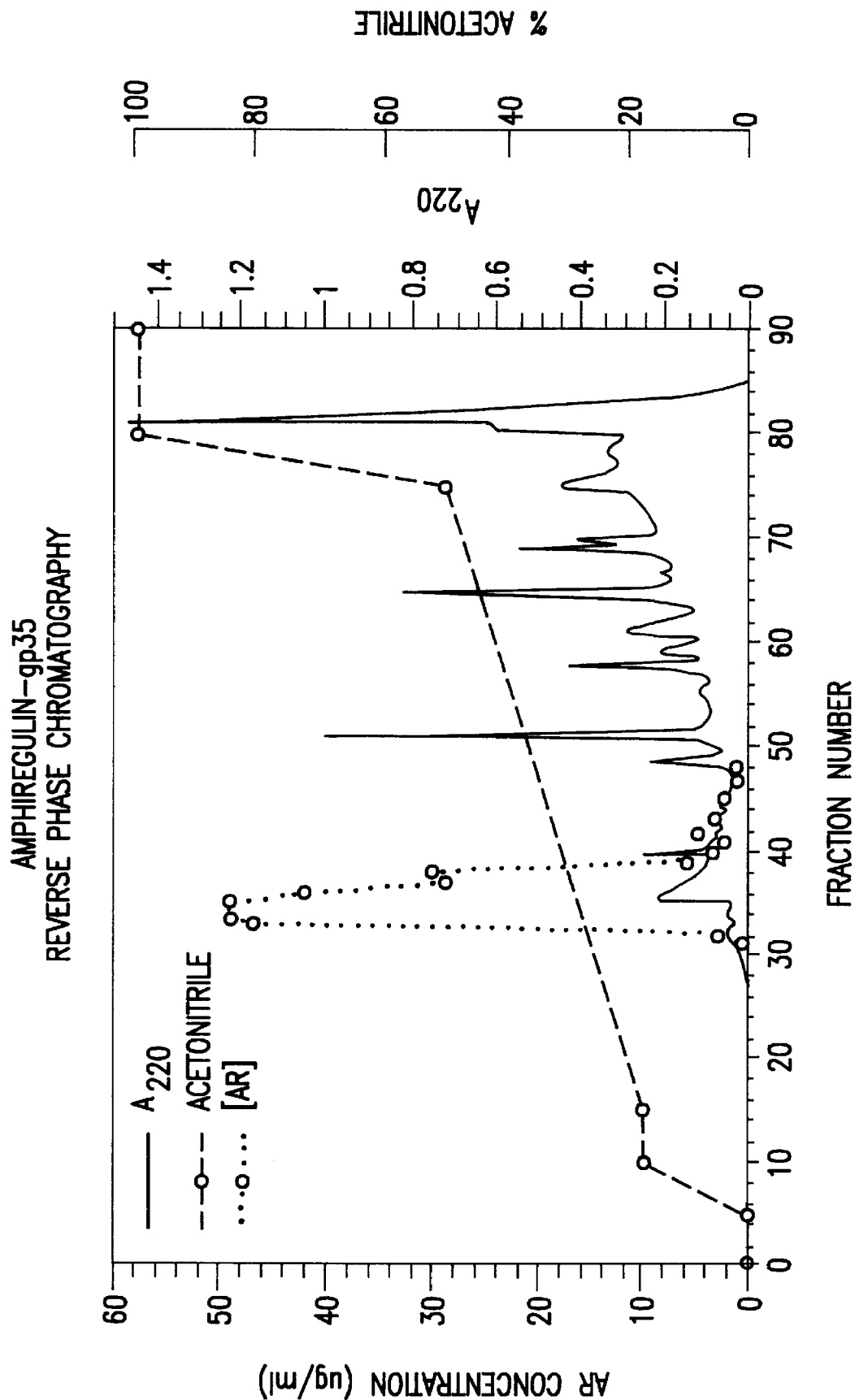

FIG. 15. Preparative reversed-phase HPLC of gp35.

Figure 16:
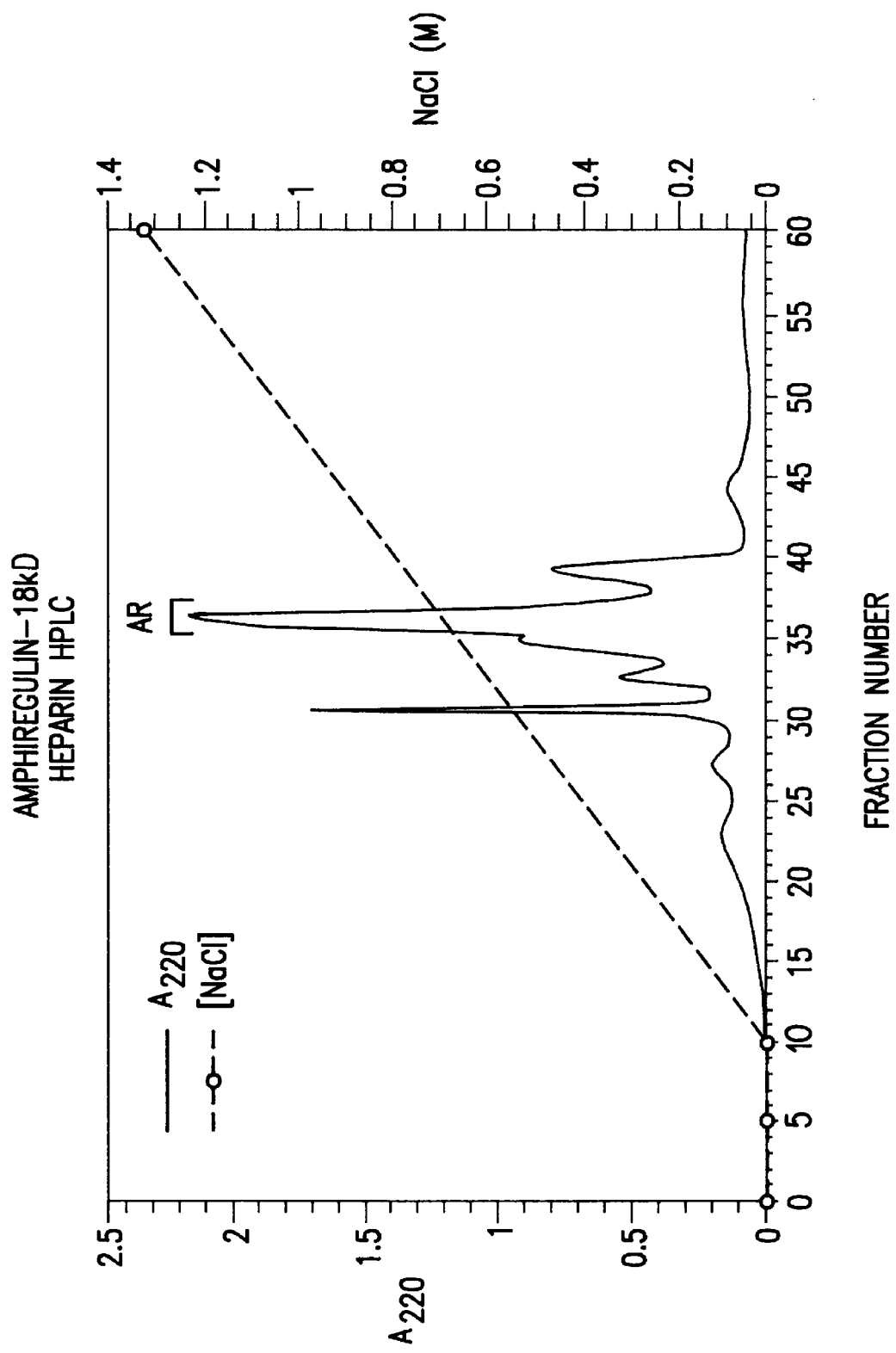

FIG. 16. Heparin HPLC of AR 18 kD-containing fractions from a reversed-phase run derived from cell factory supernatants.

Figure 17:
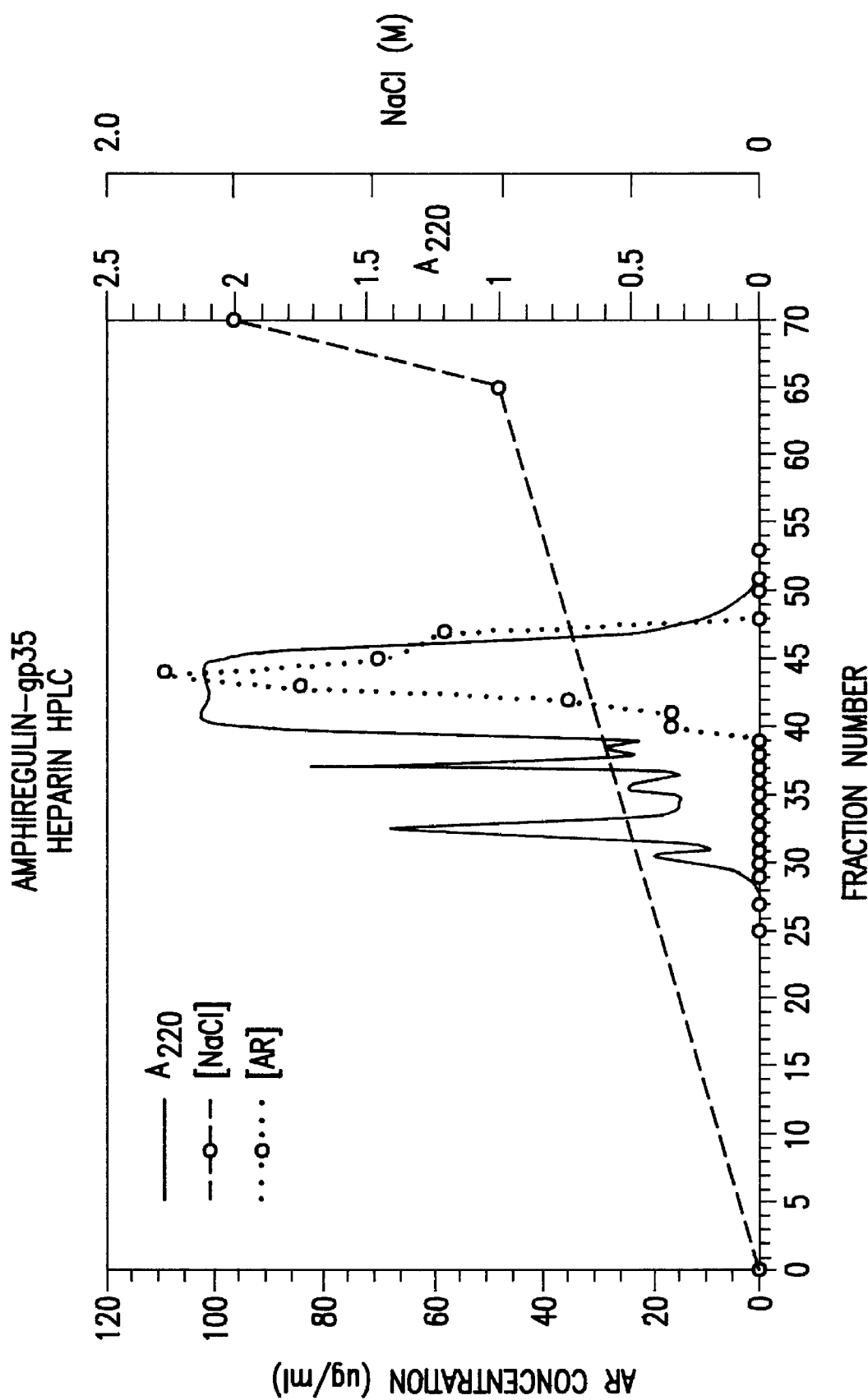

FIG. 17. Heparin HPLC of gp35-containing fractions from previous reversed-phase run.

Figure 18:
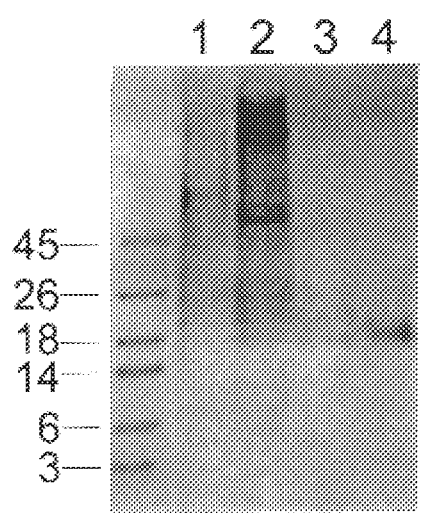

FIG. 18. SDS-PAGE analysis of AR 18 kD purified protein. Aliquots from each stage of the AR purification were analyzed on a 10% SDS-PAGE gel and stained with Commassie blue. Molecular weight markers are on the left. Lane 1, CSx eluate; lane 2, acrylic heparin eluate; lane 3, reversed-phase pool; lane 4, heparin HPLC pool.

Figure 19:
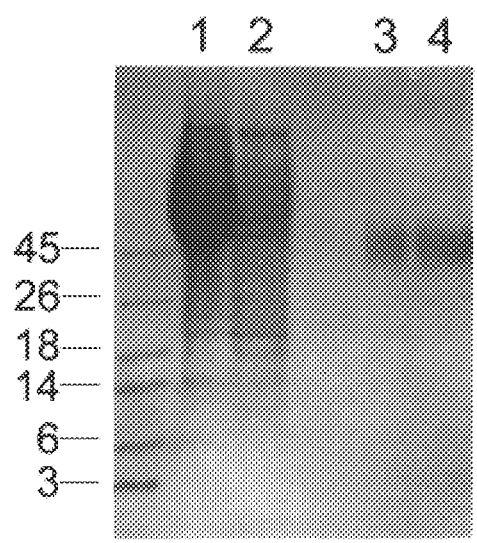

FIG. 19. SDS-PAGE analysis of gp35 purified protein. Aliquots from each stage of the gp35 purification were analyzed on a 10% SDS-PAGE gel and stained with Commassie blue. Molecular weight markers are on the left. Lane 1, Start supernatant; lane 2, CSx eluate; lane 3, reversed-phase pool; lane 4, heparin HPLC pool.

Figure 20A:
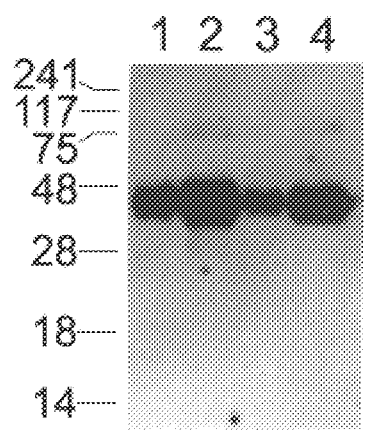
Figure 20B:
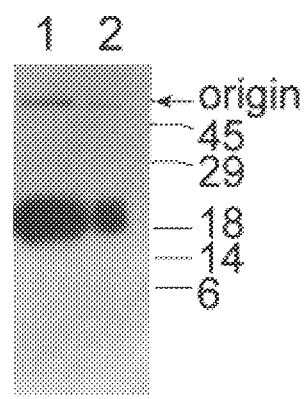

FIGS. 20A–20B. SDS-PAGE of biotinylated proteins. (A) gp35 biotinylated on free amines (lanes 1, 2) or on carbohydrate groups (lanes 3, 4). (B) AR 18 kD biotinylated on free amines (lanes 1, 2). Two aliquots of each sample were analyzed by 10% or 15% SDS-PAGE.

Figure 21A:
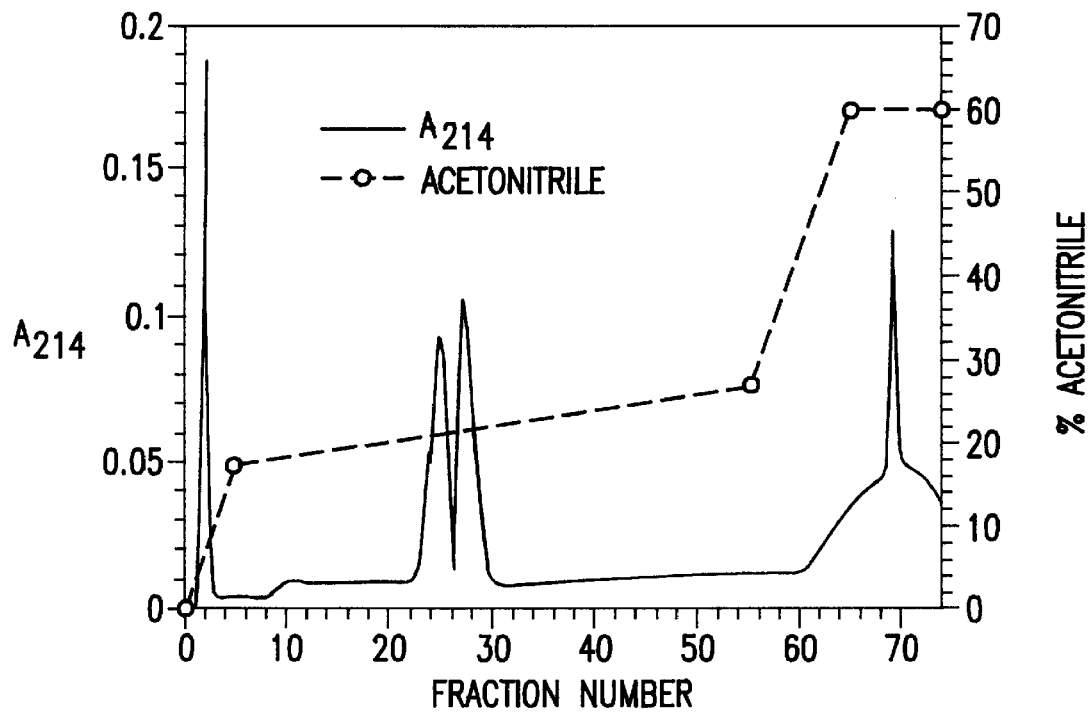
Figure 21B:
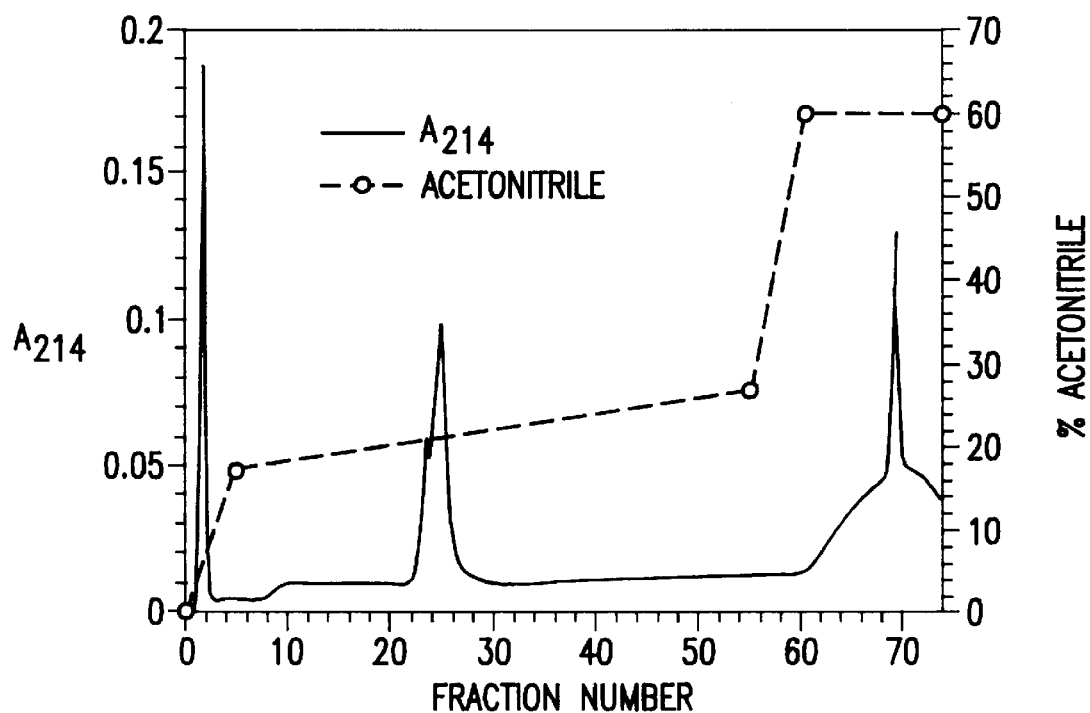
Figure 21C:
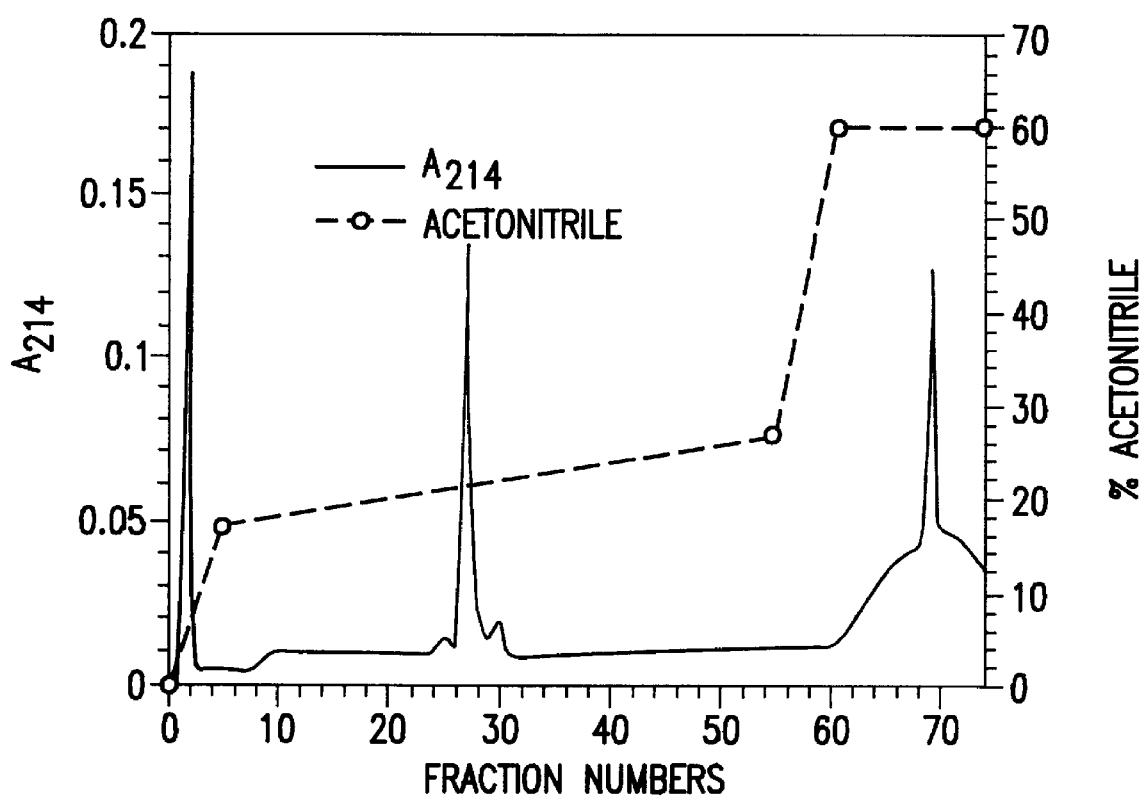

FIGS. 21A–21C. Analytical reversed-phase HPLC of (A) pooled fractions of AR 18 kD, (B) early eluting fractions 25–30, (C) late eluting fractions 31–36.

Figure 22:
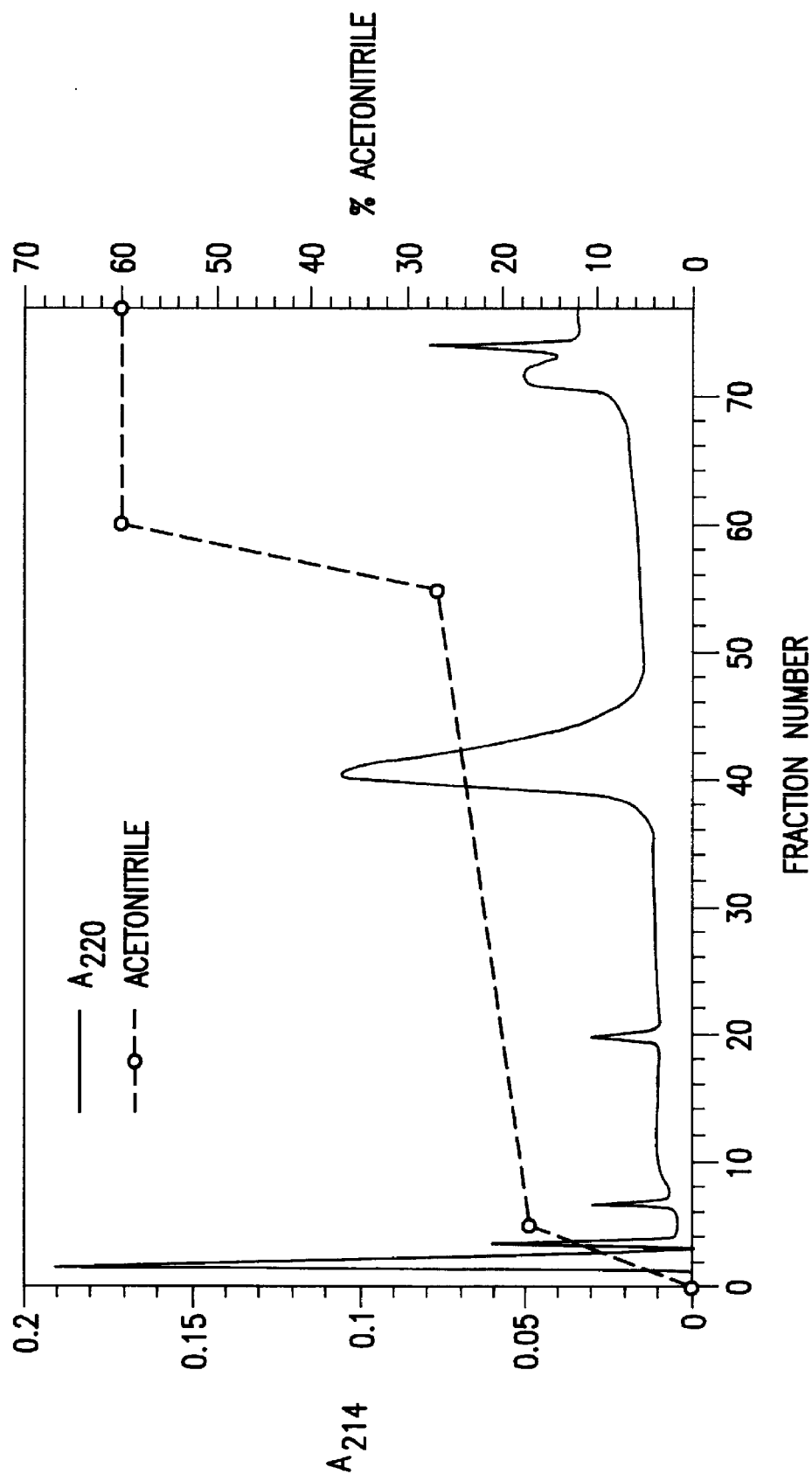

FIG. 22. Analytical reversed-phase HPLC of gp35 preparation.

Figure 23:
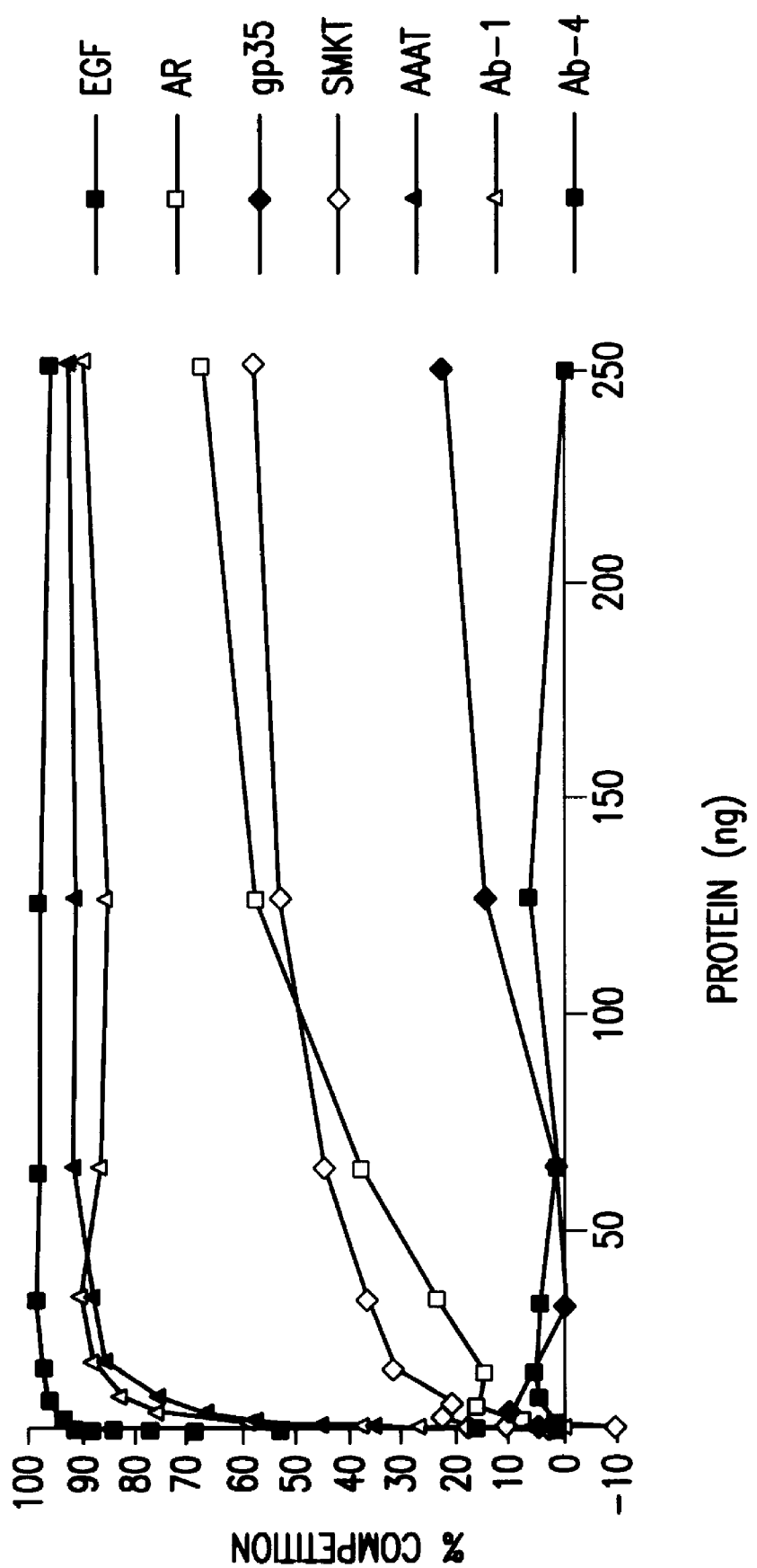

FIG. 23. Competition of $^{125}$I-EGF binding to fixed NRHER5 plasma membranes by human EGF, Ab-1 (an EGF-R blocking antibody), Ab-4 (an EGF-R non-blocking antibody), and the following recombinant proteins: human AR 18 kD, gp35, bacterially produced AR-SMKT, bacterially produced AAAT.

Figure 24:
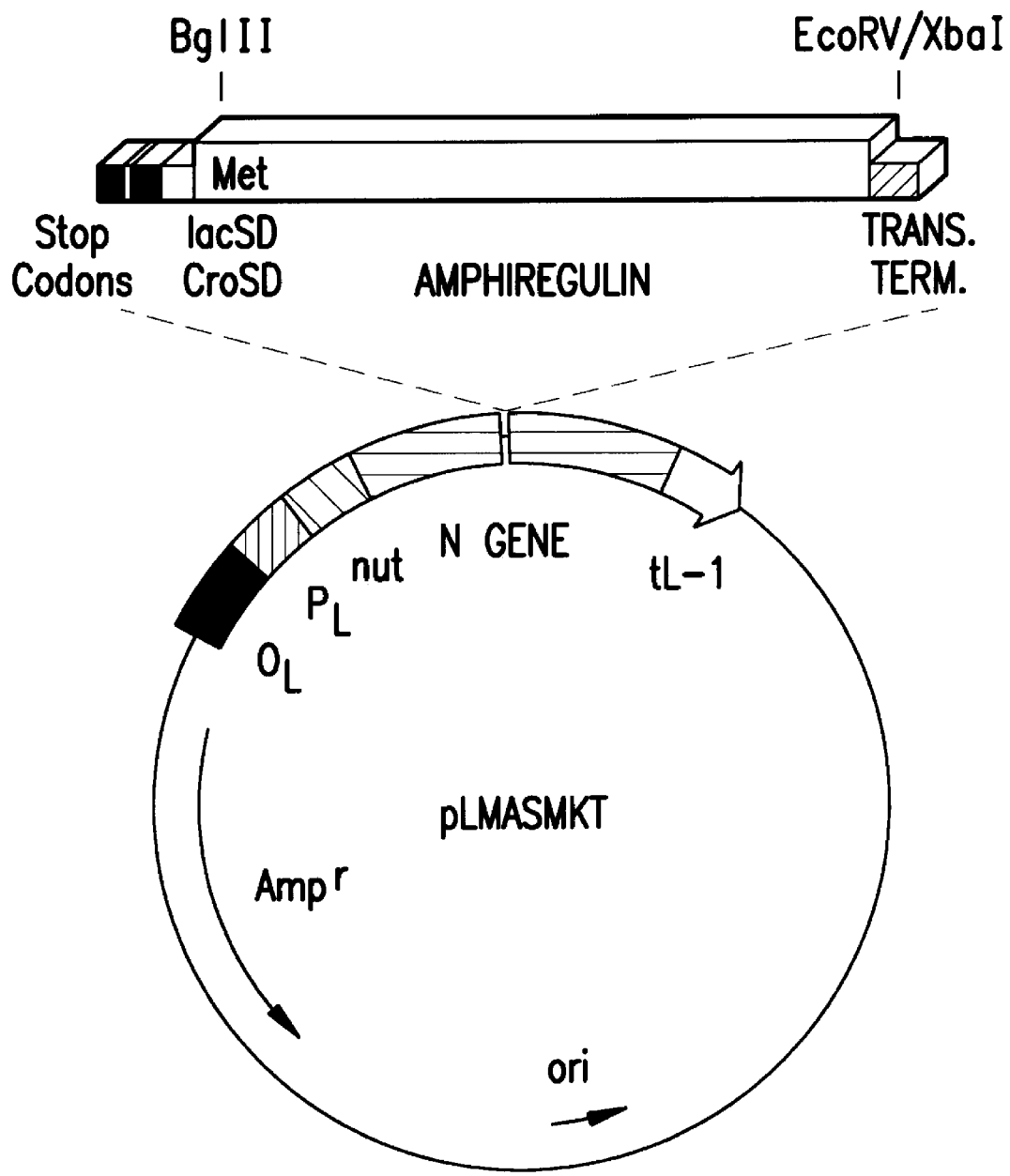

FIG. 24. Schematic map of pLMASMKT bacterial expression construct

FIGS. 25A–25B. Nucleotide sequence of the coding sequence and regulatory elements of (A) pLMASMKT (SEQ ID NOS:15 AND 16) and (B) pLMAAAT (SEQ ID NOS:17 AND 18) expression plasmids.

Figure 26:
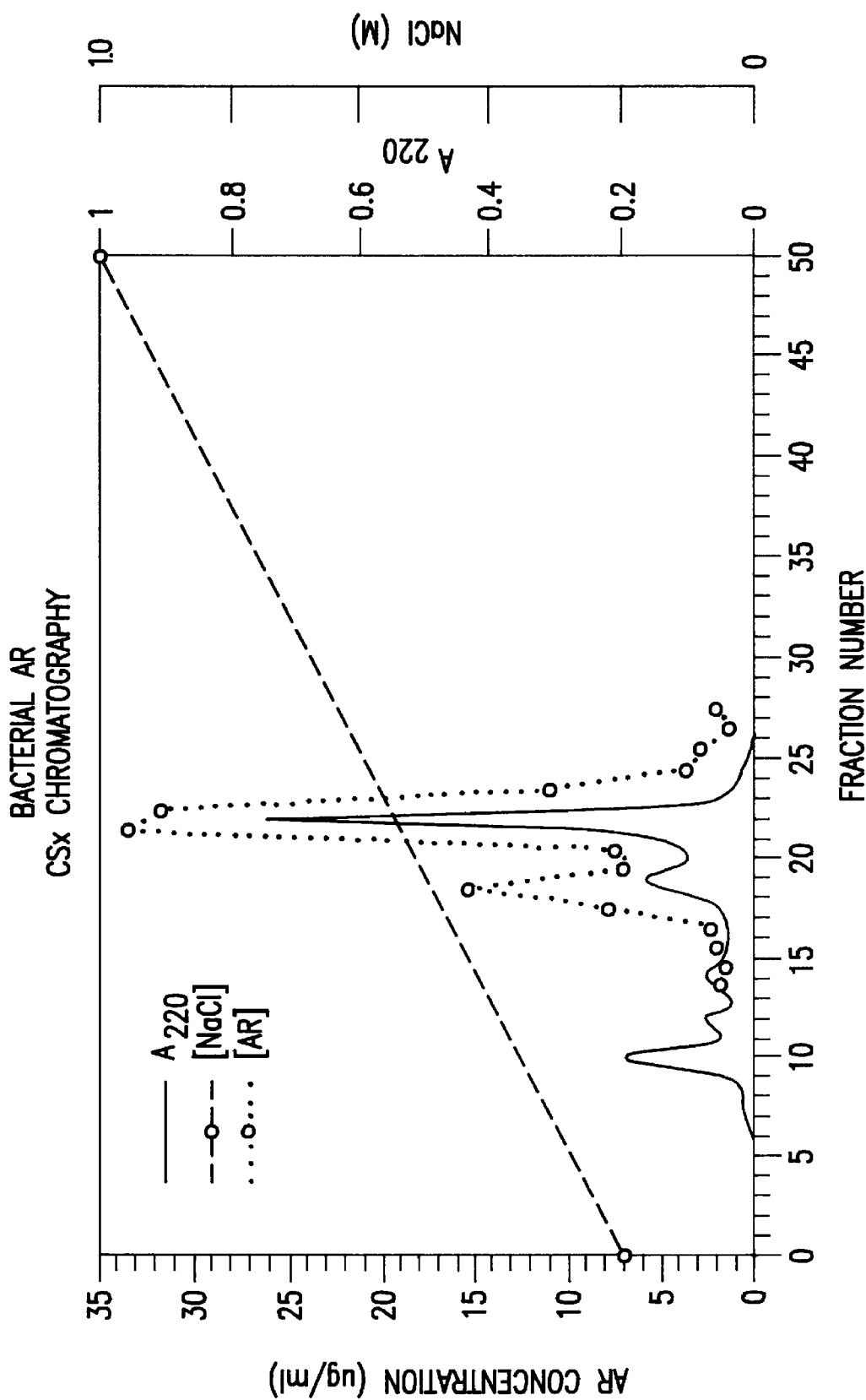

FIG. 26. Preparative CSx chromatography of refolded bacterially produced AR-SMKT.

Figure 27:
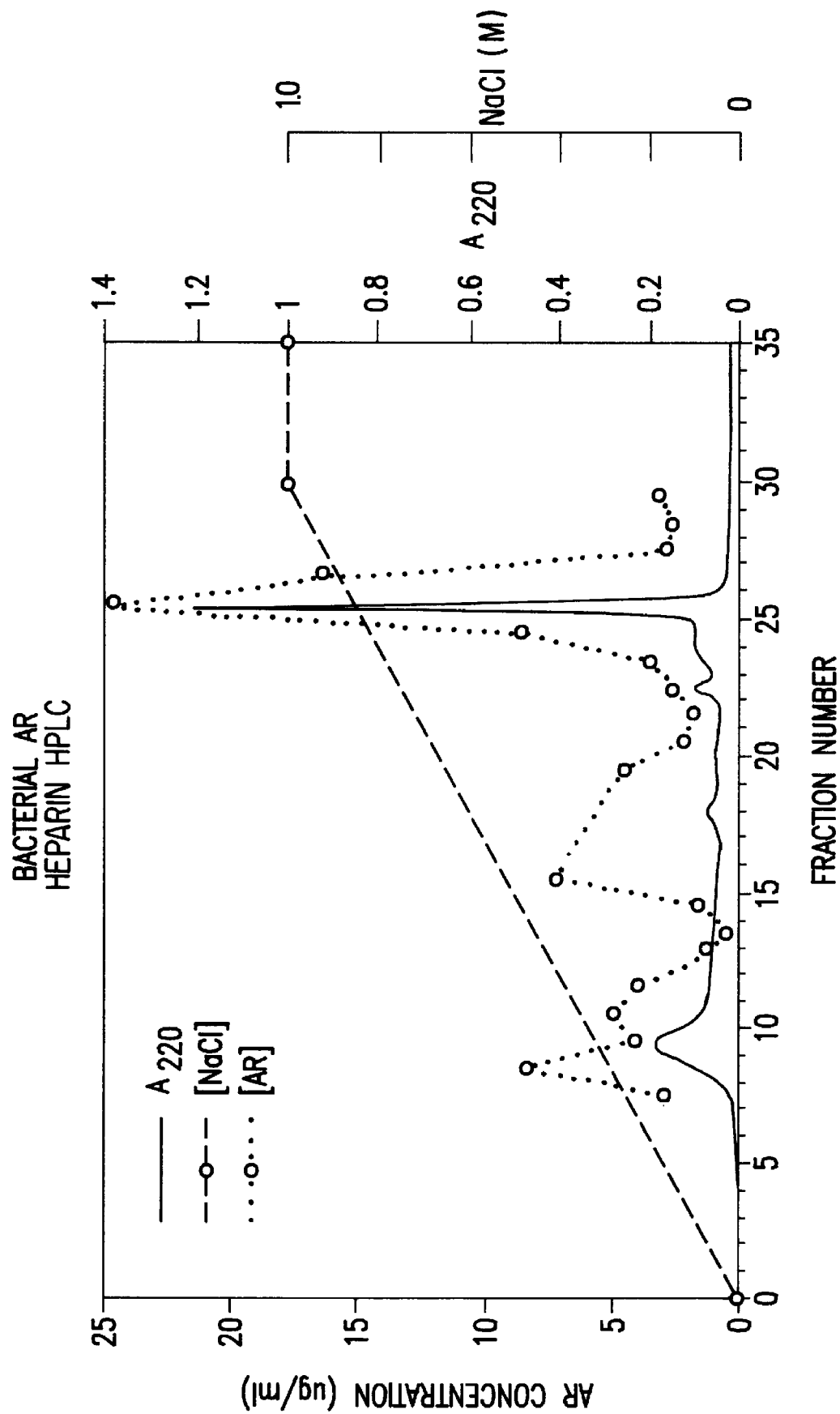

FIG. 27. Heparin HPLC of AR pool from previous run.

Figure 28:
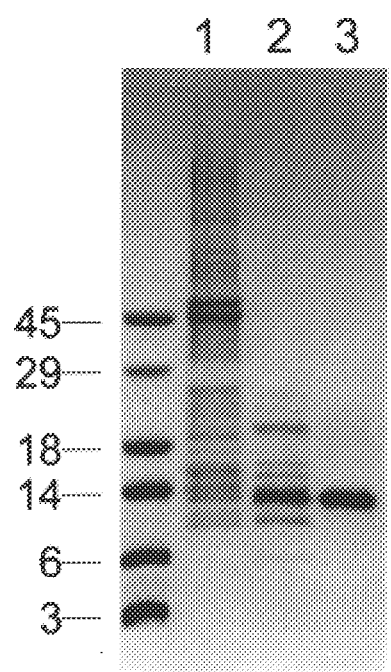

FIG. 28. SDS-PAGE analysis of bacterially produced AR-SMKT. Aliquots from each stage of the AR-SMKT purification were analyzed on a 15% SDS-PAGE gel and stained with Commassie blue. Molecular weight markers are on the left. Lane 1, solubilized inclusion body preparation; lane 2, CSx peak; lane 3, heparin HPLC peak.

Figure 29:
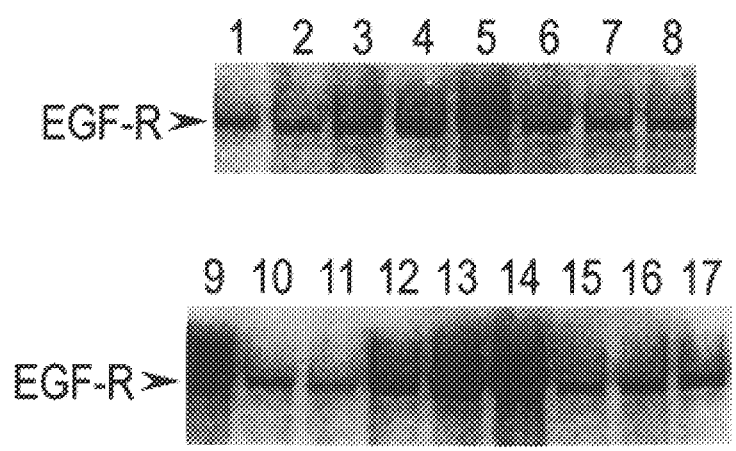

FIG. 29. EGF receptor tyrosine phosphorylation assay. Cells were stimulated for 10 min at room temperature with the following: lane 1 & 10, untreated; lane 2 & 11, 30 ug/ml heparin sulfate; lanes 3–5, 20, 50, 100 ng/ml AR-SMKT; lanes 6–8, same as lanes 3–5 except in presence of 30 ug/ml heparin; lane 9, 50 ng/ml EGF plus 30 ug/ml heparin; lanes 12–14, 20, 50, 100 ng/ml AAAT; lanes 15–17, same as lanes 12–14 except in presence of 30 ug/ml heparin sulfate. The 175 kD tyrosine phosphorylated EGF-R was visualized by Western analysis with an antiphosphotyrosine antibody.

Figure 30:
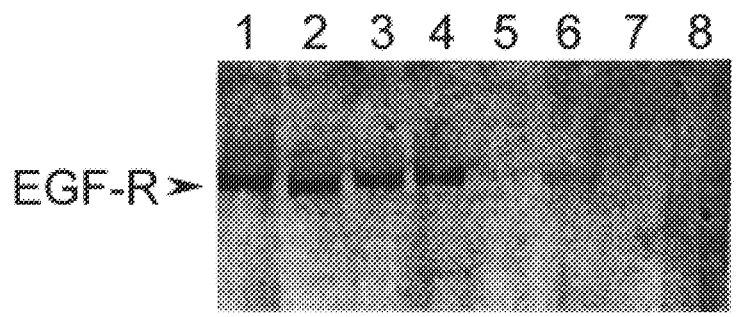

FIG. 30. AR neutralizing antibodies in EGF receptor tyrosine phosphorylation assay. Uncloned supernatants from each hybridoma were incubated with 100 ng/ml AR for 5 min prior to stimulation of NRHER5 cells for 10 min. Monoclonal antibodies 4.12, 10.14, 4.5, and 4.20 (lanes 1–4, respectively) failed to block EGF-R tyrosine phosphorylation, whereas MAb 4.14, 12.33, 16.21, and 19.23 (lanes 5–8, respectively) completely abrogated signalling. The 175 kD tyrosine phosphorylated EGF-R was visualized by Western analysis with an antiphosphotyrosine antibody.

Figure 31:
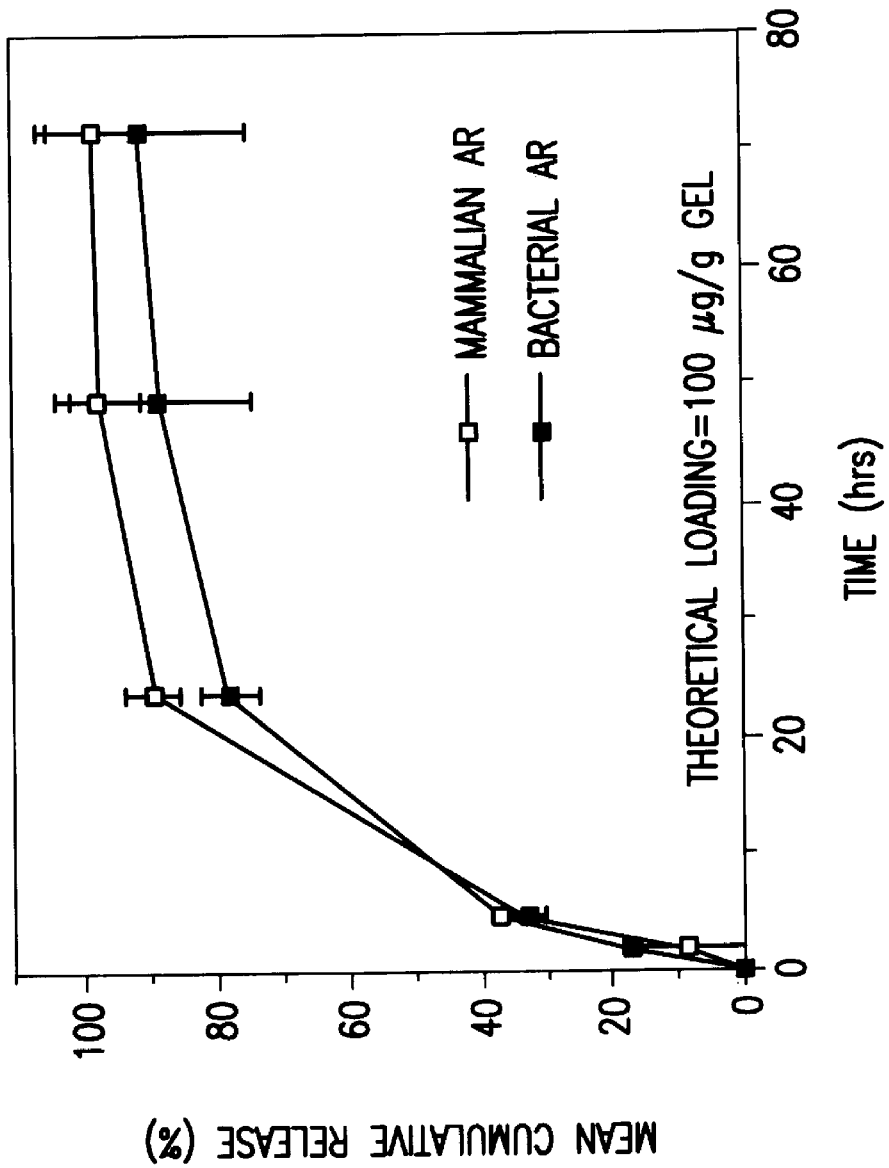

FIG. 31. Time course of the release of AR-18 kD and AR-SMKT from Pluronic gel.

Figure 32:
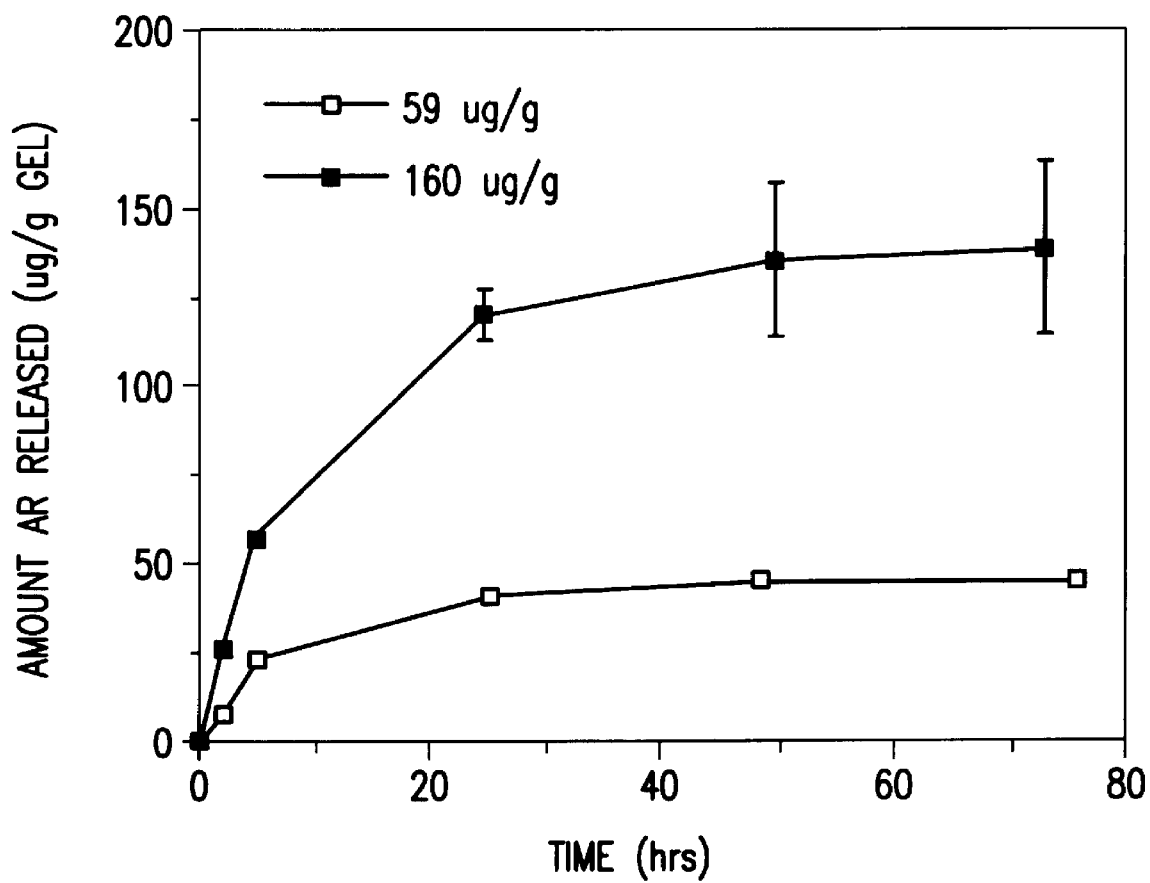

FIG. 32. Time course of the release of AR-SMKT from Pluronic gel at two doses.

Figure 33:
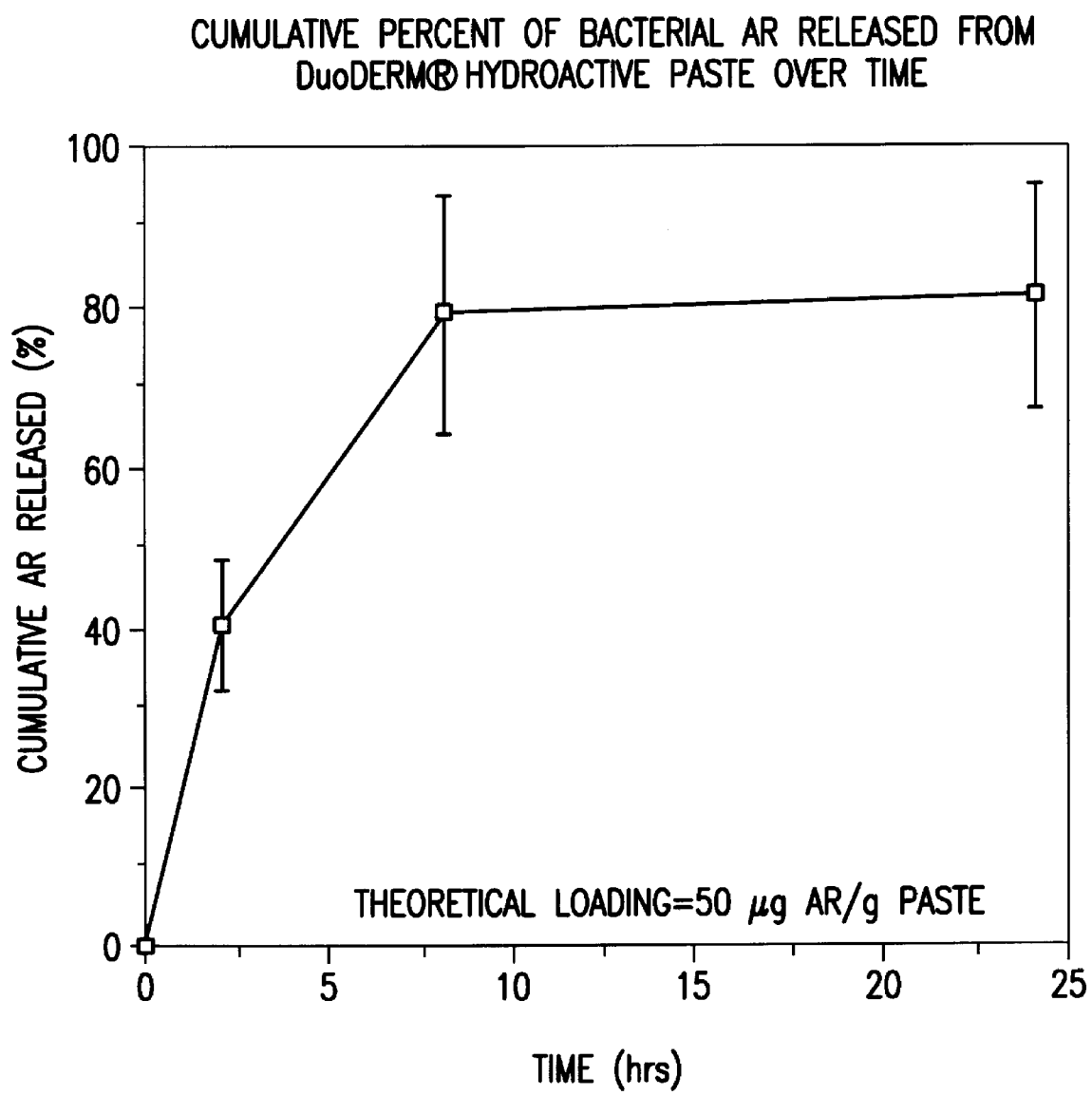

FIG. 33. Time course of the release of AR-SMKT from duoDERM hydroactive paste.

5. DETAILED DESCRIPTION OF THE INVENTION

5.1. THE AMPHIREGULIN GENE FAMILY

Amphiregulin (AR) was originally identified, characterized, and molecularly cloned from TPA-treated human cell line MCF-7. This invention encompasses other members of the AR family including AR-related genes and gene products from cells of various species. The methods described herein may be applied to the isolation and expression of all genes of the AR family.

5.1.1. ISOLATION AND CLONING OF GENES OF THE AMPHIREGULIN FAMILY

In the practice of the invention, the nucleotide coding sequence for AR, or its functional equivalent can be used to generate recombinant molecules which will direct the expression of an AR-like gene product of any species. The nucleotide coding sequence for AR may be obtained from cell sources that produce AR-like activity. For example, the human breast carcinoma cell line MCF-7 was originally used as the source of the human AR nucleotide coding sequence. The coding sequence may be obtained by cDNA cloning of RNA isolated and purified from such cellular sources or by genomic cloning from any cells containing an AR-like gene. Either cDNA or genomic libraries of clones may be prepared from the DNA fragments generated using techniques known in the art, including but not limited to the use of restriction enzymes. In a specific embodiment, by way of example, bovine, murine and rat AR genes were isolated from genomic libraries or by identification of conserved domains for design of degenerate oligonucleotides which were used as primers in cloning strategies based on PCR.

The fragments which contain AR-like sequences may be identified in a number of ways known in the art. For example, a portion of the AR amino acid sequence can be used to deduce the DNA sequence, which can then be chemically synthesized, radioactively labeled, and used as a hybridization probe. Alternatively, oligonucletide probes designed from highly conserved regions of the human, bovine, murine and rat AR genes may be used to isolate other members of the AR gene family from any species. In particular, probes containing sequences of the heparin-binding site and sequences surrounding the second cysteine of AR may be used for the practice of the invention.

Other methods which can be used to isolate the genes of the AR family include, but are not limited to chemically synthesizing the gene sequence itself from a known sequence which may, for example, be derived from the amino acid sequence of AR. Alternatively, in vitro translation of selected mRNA followed by functional or immunological assays of the translation products can be used. The identified and isolated gene can then be inserted into an appropriate cloning vector. A large number of vector-host systems known in the art may be used. Possible vectors include, but are not limited to, plasmids or modified viruses, where the vector system is compatible with the host cell. Such vectors include, but are not limited to, bacteriophages such as lambda derivatives, or plasmids such as pBR322 or pUC plasmid derivatives. Recombinant molecules can be introduced into host cells via transformation, transfection, infection, electroporation, etc.

In a particular embodiment an AR gene was isolated from a bovine genomic DNA library by using probes corresponding to 5' and 3' ends of human AR cDNA. The subsequent sequencing of the bovine AR gene revealed regions of homology between human AR and bovine AR genes and conservation of intron-exon organization. Degenerate oligo-nucleotides encompassing conserved sequences contained in a single exon from the human bovine AR gene, were successfully used to clone the mouse and rat AR genes, with the help of PCR amplification. Reverse transcriptase-PCR techniques can also be used with opposing degenerate oligonucleotide primers, particularly if a potential rich source of AR transcripts can be predicted based on the expression profile of the AR gene. For example, proliferating epithelial cells or certain tissue such as testis, ovary, or placenta would be a potential source of AR mRNA from diverse species. By varying the sequences of the probes and stringency in the hybridization procedure, other members of the AR gene family in any species may be isolated using the methods described herein.

Furthermore, the nucleotide sequence of the AR cDNA can be used to deduce AR primary amino acid sequence. Due to the inherent degeneracy of nucleotide coding sequences, other DNA sequences which encode substantially the same or a functionally equivalent amino acid sequence may be used in the practice of the methods of the invention. Such alterations of the AR nucleotides sequence include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

5.1.2. CONSTRUCTION OF EXPRESSION VECTORS CONTAINING THE AMPHIREGULIN CODING SEQUENCE

In order to express a biologically active, AR, an expression vector/host system should be chosen which provides not only for high levels of transcription and translation but for the correct processing of the gene product. This is especially important when employing the entire coding sequence of the AR precursor in the expression contructs since different forms of AR are derived from the precursor product via cellular processing events. For example, a mammalian host cell system may be chosen for its ability to correctly process and secrete AR into the extracellular environment. Alternatively, truncated forms of the AR precursor may be capable of producing active recombinant protein, thereby avoiding rate- or quantity- limiting steps in the processing of the AR precursor. In addition, the unglycosylated bacterial expression products can be produced in an active form.

Two forms of mature AR were originally identified from TPA-induced MCF-7 cells. Both forms are first synthesized as a 252 amino acid transmembrane precursor with release of the 78 and 84 aa soluble factors by alternate protelytic processing events. Further, additional forms of soluble and membrane bound AR have been identified when the AR genes are expressed in certain mammalian host cells. Naturally-occurring AR is glycosylated and may undergo tyrosine-sulfation, further underscoring the importance of selecting an expression system which is capable of executing these post-translational modifications, if desired in the final product.

A variety of animal/host expression vector systems (i.e., vectors which contain the necessary elements for directing the replication, transcription and translation of the AR coding sequence in an appropriate host cell) may be utilized equally well by the skilled artisan. These include, but are not limited to, virus expression vector/mammalian host cell systems (e.g., cytomegalovirus, vaccinia virus, EBV, retroviral vectors, adenovirus, and the like); insect virus expression vector/insect cell systems (e.g., baculovirus); or non-viral promoter expression systems derived from the genomes of mammalian cells (e.g., the mouse metallothionine promoter).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionine promoter) or from viruses that grow in these cells, (e.g. vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire AR gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided, such as in the production of AR in bacterial expression systems. Furthermore, the initiation codon must be in phase with the reading frame of the AR coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the AR gene and appropriate transcriptional/translational control signals. These methods may include in vitro recombinant DNA techniques, synthetic techniques and in vivo recombinations (genetic recombination).

For example, in cases where an adenovirus is used as an expression vector, the AR coding sequence may be ligated to an adenovirus transcription/translation control complex, e.g., the late promoter and tripartite leader sequence. This chimeric gene may then be inserted in the adenovirus genome by In vitro or in vivo recombination. Insertion in a non-essential region of the viral genome (e.g., region E1 or E3) will result in a recombinant virus that is viable and capable of expressing AR in infected hosts. Similarly, the vaccinia 7.5K promoter may be used.

An alternative expression system which could be used to express AR is an insect system. In one such system, *Autographa californica* nuclear polyhedrosis virus (AcNPV) is used as a vector to express foreign genes. The virus grows in *Spodoptera frugiperda* cells. The AR coding sequence may be cloned into non-essential regions (for example the polyhedrin gene) of the virus and placed under control of an AcNPV promoter (for example the polyhedrin promoter). Successful insertion of the AR coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed.

Retroviral vectors prepared in amphotropic packaging cell lines permit high efficiency expression in numerous cell types. This method allows one to assess cell-type specific processing, regulation or function of the inserted protein coding sequence.

In addition, a host cell strain may be chosen which modulates the expression of the inserted sequences, or modifies and processes the gene product in the specific fashion desired. Expression from certain promoters can be elevated in the presence of certain inducers, (e.g. zinc and cadmium ions for metallothionein promoters, temperature or naladixic acid for pPL-lambda bacterial promoter). Therefore, expression of the genetically engineered AR may be controlled. This is important if the protein product of the cloned foreign gene is lethal to host cells.

Furthermore, modifications (e.g. glycosylation) and processing (e.g., cleavage) of protein products are important for the function of the protein. Different host cells have characteristic and specific mechanisms for the post-translational processing and modificatin of proteins. Appropriate cell lines or host systems can be chosen to ensure the correct modification and processing of the foreign protein expressed.

Expression in bacterial systems can be accomplished by inclusion of a secretory leader sequence to direct export to the periplasmic space. Mutant strains can be selected or generated that have enhanced ability to export soluble, folded proteins. Alternatively, the protein can be made as an inclusion body directly or fused to another peptide (N-gene, β-galactose). The inclusion bodies must then be isolated, solubilized and the protein refolded and purified.

Expression vectors which may be used according to the present invention include, but are not limited to, the following:

Plasmid αCDM8 (Invitrogen)

Plasmid pSV2Neo (Southern et al., 1982 J. Mol. Applied Genetics) 1,327–341;

Plasmid pSV2dhfr (Subramani et al., 1981, Mol. Cell Biol. 1,854–864);

Plasmid pH3M (Aruffo et al., 1987, Proc. Natl. Acad. Sci. U.S.A., 84, 336514 3369);

Plasmid pH3M/bOncM;

Plasmid pMcNeo polA;

Plasmid pcARGE;

Plasmid pcARP;

Plasmid pEEEARSMKT;

Plasmid EE14;

Plasmid EEARP;

Plasmid ptACAPHILE;

Plasmid pP$_L$-lambda;

Plasmid pPLMASMKT;

Plasmid pPLMAAAT;

Plasmid pZEM;

Plasmid pLOSNL;

Plasmid pLARSNL.

5.1.3. IDENTIFICATION OF TRANSFECTANTS OR TRANSFORMANTS EXPRESSING THE AMPHIREGULIN GENE PRODUCT

The host cells which contain the recombinant AR coding sequence and which express the biologically active product may be identified by at least four general approaches: (a) DNA-DNA, DNA-RNA or RNA-antisense RNA hybridization; (b) the presence or absence of "marker" gene functions; (c) assessing the level of transcription as measured by the expression of AR mRNA transcripts in the host cell; and (d) detection of the gene product as measured by immunoassay and, ultimately, by its biological activity.

In the first approach, the presence of the AR coding sequence inserted in the expression vector can be detected by DNA-DNA hybridization using probes comprising nucleotide sequences that are homologous to the human, bovine, murine, or rat AR coding sequences.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the AR coding sequence is inserted within a marker gene sequence of the vector, recombinants containing the AR coding sequence can be identified by the absence of the marker gene function. Alternatively, a marker gene can be placed in tandem with the AR sequence under the control of the same or different promoter used to control the expression of the AR coding sequence. Expression of the marker in response to induction or selection indicates expression of the AR coding sequence.

In the third approach, transcriptional activity for the AR coding region can be assessed by hybridization assays. For example, polyadenylated RNA can be isolated and analyzed by Northern blot using a probe homologous to the AR coding sequence or particular portions thereof. Alternatively, total nucleic acids of the host cell may be extracted and assayed for hybridization to such probes on fixed membranes in solution, or through use of PCR-based techniques.

In the fourth approach, the expression of the protein product can be assessed immunologically, for example by Western blots, immunoassays such as radioimmunoprecipitation, enzyme-linked immunoassays and the like. A panel of AR-specific monoclonal antibodies are described herein, infra, all of which may be used for this purpose. The ultimate test of the success of the expression system, however, involves the detection of the biologically active AR gene product. Where the host cell secretes the gene product the cell free media obtained from the cultured transfectant host cell may be assayed for AR activity. Where the gene product is not secreted, cell lysates may be assayed for such activity. In either case, biological assays such as the cell growth inhibition cell growth stimulation, and EGF-receptor tyrosine phosphorylation assays described herein or the like may be used.

5.2. STRUCTURE OF AMPHIREGULIN

Amino acid sequencing of AR purified from TPA-treated MCF-7 conditioned medium revealed two nearly identical forms of AR. One form, the larger of the two, comprises roughly 16% of the preparation. The other form, a truncated AR, comprises the remainder and majority of the preparation, and differs from its longer counterpart only in that it lacks the amino-terminal hexapeptide, SerValArgVal-GluGln (SEQ ID NO:19). The two forms are otherwise perfectly homologous at the amino acid level. These forms of AR are heavily glycosylated and migrate as a broad band between 18–25 kD on SDS-PAGE analysis. N-glycanase treatment resolves this band into a single 14 kD species.

Expression of the complete coding sequence of AR in mammalian cell lines leads to the identification of a large transmembrane precursor protein. This protein gives rise to two major, soluble AR polypeptides of 18 kD and 35–40 kD (gp35). The larger gp35 contains the 18 kD polypeptide plus an amino-terminal pro-region. High molecular weight forms of AR containing a homologous amino terminal pro-region are also detectable as products derived from the precursors of mouse, rat and bovine AR.

AR is structurally related to the EGF-super family with the conservation of 6 cysteine residues involved in 3 disulfide bonds which define the secondary structure of the mature forms of these growth factors. However, outside of this six cysteine motif, AR has significant differences from other members of this family of growth factors. The amino terminal region of AR is composed of predominately basic residues including a region which confers a heparin-binding capacity to AR. This region of AR is highly conserved across species. Recently a new member of the EGF-super family, HB-EGF, was identified that has some structural similarity to AR in this region and is also a heparin-binding molecule.

The carboxyl-terminal region of AR differs from other members of this family due to the absence of a leucine residue shown to be important for binding to the EGF-receptor and transduction of their mitogenic signal. The four AR sequences do not contain a carboxyl-terminal leucine, but their expression products are still capable of interacting with the EGF-receptor. Therefore, despite similarities with the EGF-family proteins, AR related proteins exhibit distinct characteristics, most notably, their ability to bind heparin.

The AR amino acid sequences deduced from human, bovine, murine, and rat AR genes as well as functional equivalents are within the scope of the invention. For example, the AR product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

5.3. PROPERTIES OF AMPHIREGULIN

AR was identified as a single chain glycoprotein with a median molecular weight of about 22,500 daltons which exhibits bifunctional growth modulatory activities on a variety of cells in culture. Structurally, AR is related to the EGF family of growth factors and, in addition, may share functional similarities with other members of this family as indicated by the ability of AR to effectively compete with EGF for receptor binding.

The present invention discloses additional soluble and membrane forms of AR proteins that result from alternative processing of the transmembrane precursor AR glycoprotein (45 kD). Proteolytic cleavage of the 45 kD protein after amino acid 100,106 or 184 yields integral membrane proteins of about 27 kD or 8 kD and soluble forms of AR of 35–40 kD or 18 kD. The larger of the soluble AR polypeptides, referred to as gp35, contains the complete hydroprphilic heparin binding and cysterine rich region found in the smaller soluble 18 kD AR proteins in addition to an N-terminal extension of 80 amino acids.

AR protein is similar to the EGF-R binding family of proteins in that it also binds to EGF-R. Both soluble forms of AR are capable of interacting with EGF-R, with the larger gp35 protein having a reduced affinity for EGF-R when compared to the smaller 18 kD soluble protein. The integral membrane forms of AR may bind to EGF-Receptors expressed on adjacent cells, thereby exerting their effect through cell to cell contacts. The membrane forms of AR may function during growth and development as a means of concentrating AR activity to localized areas of cell to cell contacts.

5.3.1. AR REGULATION BY HEPARIN

Heparin exerts a growth inhibitory effect on some cell types, including keratinocytes, mammary epithelial cells, and vascular smooth muscle cells. In keratinocytes and mammary epithelial cells, this effect appears to be the result of blocking the autonomous AR production. The EGF-R tyrosine phosphorylation assays suggest this effect occurs at the level of receptor binding and activation. By a mechanism analagous to that exerted by heparin, other small molecules may also block AR binding and cell growth modulatory effects. Heparin is closely related to heparin sulfate, a natural regulator of cell growth. Heparin sulfate can exist as free glycosaminoglycan (GAG) chains, or can be covalently linked to the protein core of certain proteoglycans which are prominent components of the cell surface and of the extracellular matrix. These sulfated GAGs appear to have diverse roles in cell adhesion, matrix organization, and growth regulation. Conceivably, some of these functions may in part be due to an interaction with AR, and these effects could be modulated by administration of natural or synthetic small molecules that have the ability to block AR binding to cell surface receptors. Like AR, the binding and growth stimulatory activity of AAAT is also heparin-sensitive, suggesting that other heparin-binding EGF-like molecules, might be sensitive to regulation by small molecules such as sulfated GAGs.

Heparin is known to inhibit vascular smooth muscle cell (SMC) proliferation both in vitro and in vivo. Like other members of the EGF family, AR is a potent stimulator of SMC growth. Although AR expression has not been detected from SMCs or endothelial cells, recent studies show AR expression to be upregulated on activation of human macrophages. These observations suggest AR may play a role in proliferative lesions of the vessel wall, including atherosclerosis, vascular graft failure, or restenosis after angioplastly. Modulation of AR-mediated SMC proliferation may be of benefit in these pathologic processes.

5.3.2. AR EXPRESSION IN HUMAN COLORECTAL CARCINOMAS

Colorectal cancer accounts for approximately 14% of all types of cancer in the U.S.A. During the progression from normal colon epithelium to invasive and metastatic carcinoma, a select number of protooncogenes are activated such as K-ras, p53, DCC (deleted in colorectal cancer), and MCC (mutated in colorectal cancer). In fact, malignant progression is associated with the cumulative mutations of several genes. In addition to these changes, many primary colon tumors and established cell lines produce growth regulators that effect cell proliferation including: TGF-$\alpha$, TGF-$\beta$, insulin-like growth factor I (IGF-I), IGF-II and platelet-derived growth factor (PDGF). Autocrine mechanisms have been proposed for growth control in colorectal carcinoma since the receptors for these ligands also are expressed in many of the same transformed cells.

The association of AR expression with neoplastic progression in the colon was tested. In a panel of approximately 30 patients with primary human colorectal carcinoma, AR mRNA was expressed in 15% of the normal colonic mucosa, 50% of primary colorectal carcinomas, and 79% of these tumors that had metastasized to the liver. Protein expression also concurred with the amount of mRNA as judged by immunostaining. These findings suggest AR may be a useful marker for malignant versus normal colonic epithelium, and that AR may provide a selective growth advantage for colorectal carcinomas. Disruption of this autocrine loop may be of therapeutic utility. In addition, targeting of AR-toxin conjugates, or AR-neutralizing MAbs, to autocrine-stimulated tumors such as these may help to contain these malignancies.

These studies suggest AR expression is upregulated late in the development of colorectal carcinomas, and that it may promote the growth of these transformed colonic epithelial cells through an autocrine mechanism. Similarly, AR may be capable of stimulating the growth of normal colon epithelia and could be of therapeutic importance in regenerating epithelium in the gastrointestinal tract, such as following radiation treatment or chemotherapy, healing of gastrointestinal ulcers, or recovery from gastroenteritis and other infectious, autoimmune, or toxic insults to the digestive system.

5.3.3. AR AS A NATURAL EPITHELIAL CELL GROWTH FACTOR

AR is an autocrine growth factor for several types of normal human epithelial cells in culture. Human keratinocytes, mammary epithelial cells, and colorectal-derived cells have been shown to proliferate in response to autocrine produced AR (Cook, P. W. et al, Mol Cell Biol., 1991, 2547–2557). Like EGF and TGF-$\alpha$, AR can stimulate the growth of multiple types of epithelial cells. However, the finding that many of these cells are autocrine regulated by AR suggests that it may be an important natural regulator of epithelial cell growth. In addition, AR is less potent than other EGF-family members in stimulation of the growth of normal human fibroblasts. Conceivably, the autocrine nature of its effects on epithelial cells, its heparin-regulated activity, its attenuated binding to the EGF-R, and its diminished stimulation of fibroblast proliferation may be of significance in various in vivo settings, such as wound healing. AR may be of use in healing of compromised ulcers (stasis, decubitous, diabetic, infectious), for stimulation of corneal healing, protection or repair of ulcers in the oral and gastrointestinal tracts, proliferation of retinal neuroepithelium, stimulation of bronchial epithelium, hair follicle growth, growth of the epithelial lining of the reproductive tract and ovaries, growth of urinary tract epithelium, neuronal support and survival secondary to glial cell stimulation, or in other pathologies of impaired epithelial cell growth. As a common and natural stimulator of epithelial cell growth, AR may also play a role in stimulation and propagation of certain reposits of epithelial stem cells, such as those in the intestine, cornea, retina, liver, pancreas, and respiratory tract.

Specific blocking of AR-mediated growth stimulation may be useful in disorders involving epithelial hyperproliferation, including; dermal hyperproliferative diseases such as psoriasis and eczema, proliferative breast disease, proliferative disorders of the gastrointestinal tract such as gastrimomas, polyps, or carcinoma, proliferative glomerulopathies, and atherosclerosis. Currently both small molecules (heparin) and neutralizing AR MAbs are available to block AR-mediated cell growth. Conceivably, receptor antagonists could also be identified from natural sources, or generated by recombinant techniques.

5.4. AMPHIREGULIN-RELATED DERIVATIVES, ANALOGUES. AND PEPTIDES

The production and use of derivatives, analogues, and peptides related to AR are also envisioned and are within the scope of the invention. Such derivatives, analogues, and peptides which exhibit growth modulatory activity may find applications in the diagnosis, prognosis, and treatment of a wide variety of neoplasias. Such derivatives, analogues, or peptides may have enhanced or diminished biological activities in comparison to native AR and/or may expand or limit the range of cell susceptibility for AR growth inhibitory activity, and still be within the scope of the invention. Similarly, the production and use of derivatives, analogues, and peptides related to AR which exhibit enhanced or diminished growth stimulatory activity and/or which expand or limit the range of cells responsive to AR's growth regulatory activity may find useful applications including, but not limited to, the treatment of hyper- or hypo-proliferation of epithelial cells.

AR-related derivatives, analogues, and peptides of the invention may be produced by a variety of means known in the art. Procedures and manipulations at the genetic and protein levels are within the scope of the invention.

At the protein level, numerous chemical modifications could be used to produce AR-like derivatives, analogs, or peptides by techniques known in the art, including but not limited to specific chemical cleavage by endopeptidases (eq. cyanogen bromides, trypsin, chymotrypsin, V8 protease, and the like) or exopeptidases, heparinases, acetylation, formylation, PEGalation oxidation, etc.

5.5. ANTI-AMPHIREGULIN ANTIBODY PRODUCTION

Also within the scope of the invention is the production of polyclonal and monoclonal antibodies which recognize Amphiregulin, or related proteins.

Various procedures known in the art may be used for the production of polyclonal antibodies to epitopes of AR. For the production of antibodies, various host animals can be immunized by injection with the AR protein, or a synthetic AR peptide, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peotides, oil emulsions, keyhole lympet hemocyanins, dinitrophenol, and potentially useful human adjuvants such as BCG (bacille Calmette-Guerin) and *Corynebacterium parvum.*

A monoclonal antibody to an epitope of AR can be prepared by using any technique which provides for the production of antibody molecules by continuous cell lines in culture. These include but are not limited to the hybridoma technique originally described by Kohler and Milstein (1975, Nature 256, 495–497), and the more recent human B-cell hybridoma technique (Kosbor et al., 1983, Immunology Today 4:72) and EBV-hybridoma technique (Cole et al., 1985, Monoclonal Antibodies and Cancer Therapy, Alan R. Liss, Inc., pp. 77–96).

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generaged by reducing the disulfide bridges of the F(ab')$_2$ fragment, and the two Fab or Fab fragments which can be generated by treating the antibody molecule with papain and a reducing agent.

Antibodies to AR may find use in the qualitative and quantitative detection of mature AR and its precursor and subcomponent forms, in the affinity purification of AR proteins, and in the elucidation of AR biosynthesis, metabolism and function. Antibodies to AR may also be useful as diagnostic and therapeutic agents.

In a specific embodiment, by way of example, thirty AR-reactive AR specific monoclonal antibodies were generated. Certain of the antibodies neutralize AR biological activities and others cross-react with AR from 4 different species, or to other members of the EGF-superfamily.

5.6. USES OF AMPHIREGULIN

The bifunctional nature of AR provides for a wide variety of uses in vitro and in vivo. Any composition which includes AR, or fragments and derivatives thereof which exhibit growth inhibitory and/or growth stimulatory activity, either alone or in conjunction with other biologically active growth factors, inhibitors, or immunomodulatory agents, may be employed in the practice and method of the invention.

The localization of the AR gene to a region involved in lymphocyte differentiation suggests AR may play a role in hematopoeitic cell development, activation or immunosuppression. This function is also supported by the homology between the AR3'-untranslated region and similar regions from other cytokines.

The subject compounds may be used in the modulation of angiogenesis, bone resorption, immune response, and synaptic and neuro effector functions. AR may also be used in the modulation of the arachidonic acid cascade. Enzymatic oxidation of arachidonic acid leads to a multitude of important products such as prostaglandins, thromboxanes, prostacyclins, and leukotrienes. Such products are extremely potent, ubiquitous agents with numerous physiological effects including, for example, muscle contraction, platelet aggregation, leukocyte migration, and gastric secretion. AR, AR-related molecules, and compositions thereof may be especially useful in the treatment of wounds and in the diagnosis and treatment of cancer.

6. EXAMPLE: ISOLATION OF AMPHIREGULIN cDNAs FROM VARIOUS SPECIES

6.1. MATERIALS AND METHODS

6.1.1. ELISA

Mouse monoclonal antibody (Mab) AR1 was raised against a peptide (amino acids 144–184) spanning the EGF-like domain of mature AR, and was used as uncloned hybridoma culture supernatant 6R1C2.8 or as purified antibody 6R1C2.4. Samples containing 0.5 pg–1.0 ng amphiregulin were bound to the bottom of a Falcon 96-well tissue culture plate in 0.1 ml 2×SSC+1% BSA and incubated at 37° C., for 1 hr, or 4° C., overnight. Excess liquid was removed, and 0.2 ml diluting buffer (0.25% BSA, 0.05% Tween 20 in PBS) was added per well, and the wells were incubated at 25° C. for 30 min. Excess liquid was removed, 0.05 ml mouse hybridoma supernatant 6R1C2.8 was added per well, and the wells were incubated at 25° C. for 1 hr. The wells were washed three times with PBS; then 0.1 ml of affinity purified F(ab')$_2$ goat anti-mouse IgG+IgM conjugated with horseradish peroxidase (Pel-Freez, 1:1000 in diluting buffer) was added per well, and the wells were incubated at 37° C. for 30 min. The wells were washed four times with PBS; then 0.1 ml of chromagen reagent (1 mg of 3',3'4',5'-tetramethylbenzidine per ml in dimethyl sulfoxide) diluted 1:100 in buffered substrate (0.01% hydrogen peroxide in 0.1M sodium acetate [pH 6.0]) was added per well, and the wells were incubated at room temperature until blue color appeared (10 to 60 min). The reaction was stopped by adding 0.1 ml 1N H$_2$SO$_4$ per well, and the A$_{450}$ was determined on a microplate reader.

6.1.2. EGF-RECEPTOR TYROSINE PHOSPHORYLATION ASSAY

NRHER5 cells were clonally isolated from NR6 cells infected with a retrovirus stock carrying the human EGF receptor, and were found to have about or approximately $10^6$ human EGF receptors per cell. Cells were cultured in DMEM supplemented with 10% fetal bovine serum. $10^5$ cells were plated in a Falcon 6-well tissue culture plate, and grown at 37° C. for 18–24 hr. The monolayers were then incubated at room temperature with 1 ml serum free DMEM containing 10–300 ng of ligand. Ten minutes later the cells were washed with PBS and solubilized on ice with 0.5 ml PBSTDS containing phosphatase inhibitors (10 mM NaHPO$_4$, 7.25, 150 mM NaCl, 1% Triton X-100, 0.5% deoxycholate, 0.1% SDS, 0.2% sodum azide, 1 mM NaF, 1 mM EGTA, 4 mM sodium orthovanadate, 1% aprotinin, 5 ug/ml leupeptin). Cell debris was removed by centrifugation (12000×g, 15 min, 4° C.) and the cleared supernatant reacted with 1 ug of mouse monoclonal antibody R1 to the human EGF-R (Amersham). Following a 1 hr incubation at 4° C., 30 ml of a 1:1 slurry of protein A-sepharose (Pharmacia) was added and the incubation continued and additional 30 min. The beads were washed 3 times in PBSTDS and the complexes resolved by electrophoresis on reducing 7% SDS-polyacrylamide gels. The proteins were transferred to nitrocellulose and blocked with 5% BSA in Tris-buffered saline containing 0.5% Tween 20. An antibody to phosphotyrosine (PY20, ICN) was incubated in the same blocking buffer, washed with PBS, and then the immune complexes detected with $^{125}$I-goat anti-mouse Ig F(ab')$_2$. Blots were washed with PBS and exposed on a phosphorimager (Molecular Dynamics). Tyrosinespecific phosphorylation was quantitated compared to the unstimulated control.

6.1.3. IMMUNOGOLD STAINING

MCF-7 (HTB22) cells (1×10$^4$/16 mm well) were cultured for 16 hrs on glass slides prior to 24 hr treatment with TPA (100 ng/ml). Cells were fixed in freshly prepared 4% paraformaldehyde/PBS for 30 min and washed extensively. In some experiments the cells were permeablized by treatment with 0.25% Triton X-100 in 2% paraformaldehyde for 10 min and then fixed as above. The cells were then treated with blocking solution (0.8% BSA/5% normal goat serum (NGS)/1% gelatin diluted in PBS) for 1 hr, decanted, and incubated for 2.5 hrs with either a 1:1 dilution of Mab AR1 supernatant or 10 mg/ml P1.17 control mouse Mab in diluent (0.8% BSA/1% NGS/1% gelatin in PBS). Cells were washed in PBS (3×10 min) and exposed for 2–3 hrs to goat anti-mouse IgG colloid gold. For light and electron microscopy, the anti-mouse IgG was conjugated to 1 nm and 15 nm gold (Janssen, Piscataway N.J.) respectively and used at dilutions of 1:50 and 1:5 respectively. Cells were washed extensively in PBS, postfixed in 2% glutaraldehyde/PBS for 20 min and washed again. For light microscopy the size of the gold probe was increased by silver enhancement (12 min) using the Intense M kit (Janssen, Piscataway N.J.). The slides were then washed in water for 16 hr, dehydrated with graded ethanols and air dried. The cells were not coverslipped, but were observed using water immersion with a Zeiss microscope fitted with Nomarski optics. Samples for electron microscopy were treated in 1% 0SO$_4$ for 30 min, following the postfixation in glutaraldehyde. They were then dehydrated to 70% ethanol and stained with 3% uranyl acetate in 70% ethanol for 30 min. The samples were dehydrated with graded ethanol washes and embedded in methacrylate resin. Thin sections were collected on Formvar-coated grids and double stained with uranyl acetate and lead citrate. Specimens were examined with an electron microscope (model 100 B; JEOL USA, Peabody, Mass.) at an accelerating voltage of 60 kV.

6.2. RESULTS

6.2.1. ISOLATION OF AMPHIREGULIN cDNAS FROM VARIOUS SPECIES

A bovine genomic DNA library (Stratagene, La Jolla, Calif.) was probed under reduced stringency with the human pAR9 cDNA clone. Five clones were isolated, digested with EcoRI and hybridized on a Southern blot to probes from the 5'- (670 bp EcoRI-BsmI fragment corresponding to exons 1–3) and 3'- (480 bp BsmI-EcoRI fragment corresponding to exons 3–6) ends of the AR cDNA. All clones contained both a 5.2 and a 0.95 kb EcoRI fragment that hybridized to the 3' AR probe, and a single 2.5–7 kb EcoRI fragment that hybridized to the 5' AR probe. These EcoRI fragments were subcloned, and mapped for EcoRV, HindIII, PstI, PvuII, SstI, and XbaI. Fragments of 500 bp or less that hybridized to pAR9 were subcloned, sequenced, and open reading frames aligned with the human AR sequence. Oligonucleotide primers bounding both ends of the bovine AR open reading frame were synthesized and used for reverse transcriptase-PCR with bovine testis RNA as a template. The bovine testis cDNA sequence confirmed the predicted sequence derived from the genomic clones (FIG. 1A).

Alignment of the human and bovine AR cDNAs identified several stretches of complete amino acid conservation (FIG. 2). Particularly striking was the strict conservation of the sequence spanning the predicted heparin-binding site in the hydrophilic domain of AR (human AR amino acids 123–144) and a 9 amino acid sequence encompassing the second cysteine of AR (human AR amino acids 149–157). Two pools of degenerate oligonucleotides were synthesized to these regions based on the peptide sequences KRKKK and PheGlnAsnPheCysIleHisGly (SEQ ID NO:25) from the human AR cDNA (the pools contained 24 and 256 degenerate oligonucleotides in the sense and antisense orientation respectively). In addition, a nondegenerate oligonucleotide was synthesized corresponding to the sense strand of the human AR sequence encoding amino acids ProLysArgLysLysLysGly (SEQ ID NO:26). These sequences are all encoded by a single exon (exon 3) in human and bovine DNA (FIG. 3), and are separated by 57–60 nucleotides. These oligonucleotides were used as primers in a 40 cycle PCR amplification with mouse (NS-1 myeloma cells), rat (normal rat kidney) or human (MCF-7 breast carcinoma) DNA as a template. The PCR products were subcloned and numerous inserts of approximately 100 bp were sequenced. Sequences were translated in the orientation corresponding to the primers, and alligned with the human and bovine AR sequence. Several clones were identified from mouse and rat DNA that were unique, but highly related to the human and bovine AR sequence. In addition multiple clones corresponding to human AR were isolated from the MCF-7 genomic DNA. The complete mouse and rat AR cDNAs were obtained from mouse and rat tissue RNA using a PCR protocol to isolate the 5' and 3' ends of messages that have a known central sequence. In particular, a PCR strategy with exact mouse or rat AR primers oriented in the 3' and 5' directions in combination with primers that anneal to the natural poly(A) tail, or a synthetic poly(A) track added onto the 5' extended cDNA was employed (Plowman et al., 1990 Proc. Natl. Acad. Sci. U.S.A. 87:490–520 08). These probes were also used to obtain the mouse AR gene from a mouse T-cell genomic library (Stratagene, La Jolla, Calif.). Several PCR-generated clones, and all exons of the mouse AR gene were sequenced on both strands using T7 polymerase with oligonucleotide primers (Tabor and Richardson 1987, Proc. Natl. Acad. Sci. U.S.A. 84: 4767–71). The nucleotide sequences of the bovine, rat, and mouse AR and the amino acid translations, are shown in FIG. 1A–C.

An alignment of the sequences of the mouse (248 aa), rat (243 aa), bovine (248 aa), and human (252 aa) AR cDNA are shown in FIG. 2. The predicted AR precursors from mouse, rat, and bovine sources show 68–77% homology with the human protein and all are predicted to be first synthesized as transmembrane precursors. These four sequences show strict conservation of the 6 cysteines presumed to form 3 disulfide loops, as well as the His-Gly$_{156-157}$, Tyr$_{176}$, Gly$_{178}$, and Arg$_{180}$ (positions based on the human AR precursor sequence), which are present in all molecules known to bind the EGF-R (EGF, TGF-α, HB-EGF, and pox virus homologs of EGF including VGF, MGF, and SFGF). AR from these four species all conserve the predicted heparin-binding domain (SEQ ID NO:27), in addition to a potential glycosylation site at Asn$_{113}$. All four species of AR lack a leucine residue, five residues C-terminal to Cys$_{181}$, that is present in all other EGF-R binding proteins. In addition, AR shows strong conservation at the amino acid level across species in regions of the pro-domain, the hydrophilic domain, and in regions of the cytoplasmic domain. Conceivably these regions play important roles in the biology or processing of this growth factor.

The exon organization is also precisely conserved between the human, bovine, and mouse AR genes, with introns inserted at homologous locations within all three species (see FIG. 3).

A recent publication (Kimura et al., 1990 Nature 348: 257–260) referred to a factor isolated from rat schwannoma cells that was called schwannoma-derived growth factor. This sequence is identical to that of rat amphiregulin.

6.2.2. ALTERNATIVELY PROCESSED FORMS OF AR DERIVED FROM A COMMON PRECURSOR

Analysis of the human, bovine, mouse, and rat AR cDNA clones suggested that AR is synthesized as a moderately conserved 217–276 amino acid transmembrane glycoprotein precursor (proAR), following removal of the approximately 26 aa signal sequence. Sequence analysis of human AR purified from MCF-7 cells reveals the 18–25 kD glycoprotein contains a peptide core of 84 or 78 amino acid residues that are released from the extracellular domain of proAR by cleavage at Asp-Ser or Gln-Val dipeptides at the N-terminus and Lys-Ser dipeptide at the C-terminus. Furthermore, failure to cleave at one or all of these sites could produce alternate secreted or transmembrane forms of AR. These additional forms of AR could maintain activities similar to the smaller soluble forms of AR, or they could have unique receptor-binding and functional properties.

Through the use of recombinant expression and antisera directed against specific domains of proAR, we have identified several stable AR processing intermediates, all of which are derived from the common 252 amino acid precursor. Removal of the 19–26 amino acid signal sequence would leave a 225–233 amino acid transmembrane glycoprotein (approximately 45 kD, FIG. 4A) while cleavage after residue 100 (between Asp-Ser), 106 (between Gln-Val) or 184 (between Lys-Ser) of the precursor would leave 142, 137, or 68 amino acid integral membrane glycoproteins (approximately 26 kD and 8 kD, FIG. 4B and D, respectively). In addition to the 78 and 84 amino acid soluble forms of AR (FIG. 4D), a high molecular weight secreted form of approximately 158–165 amino acids is predicted following removal of the signal sequence and carboxy-terminal cleavage after residue 184 (between Lys-Ser), in the absence of processing between residues 100–106 (FIG. 4E). This 35–40 kD glycoprotein is referred to as gp35 and contains the complete hydrophilic, heparin-binding and cysteinerich domains of the 84 amino acid soluble AR in addition to an N-terminal extension of 74 amino acids. These additional N-terminal residues contain multiple sites for N- and O-linked glycosylation and the multiple tyrosine sulfatation consensus motifs.

6.2.3. CHARACTERIZATION OF SOLUBLE AND MEMBRANE-ASSOCIATED FORMS OF RECOMBINANT AMPHIREGULIN

High levels of recombinant human AR were expressed in Chinese hamster ovary (CHO) cells by dihydrofolate reductase-induced gene amplification. The AR expression plasmid, cARGE was generated by insertion of a 10 kb SmaI-EcoRV genomic fragment, containing the complete coding region of human AR, into the expression plasmid pCDM8 (Invitrogen, San Diego, Calif., see FIG. 5). This construct drives expression of AR from the CMV immediate-early promoter. cARGE was cotransfected with pSV2DHFR (containing the murine dhfr cDNA driven by the SV40 early promoter) into dhfr-deficient CHO cells and propagated in selective media. Several AR ELISA-positive clones were selected for amplification with increasing levels of methotrexate over a 5 month period. One clone, ARGE 2a-15k was chosen for further study.

Recombinant human AR was also expressed in CHO cells using glutamine-syndrome induced gene amplification. The expression plasmid pEEARSMKT was generated as follows: 1) a cDNA fragment containing the complete amino-terminal coding region of human AR with a stop codon inserted after residue 188 was generated using PCR techniques 2) this fragment was inserted into pEE14 (Cell Tech) glutamine synthetase expression vector which uses the CMV immediate-early promoter 3) the construct way transfected into CHO-KI cells and selected using 25 μM methionine-sulfoxamine (MSX) in glutamine-free GMEM-S. Selected clones were then amplified with increasing MSX concentrations. The pEEARSMKT contains the first 188 residues of the AR precursor including the signal sequence, pro-region, and cysteine-rich domain, but truncates off the transmembrane and cytoplasmic domains. We have demonstrated that the AR-pro-region is required for secretion of active AR by transient expression in COS cells of numerous mutant and chimeric AR expression constructs. However, these studies clearly demonstrate that the AR transmembrane domain is not necessary and in fact limits the amount of secreted soluble, active AR recoverable from the culture media. In fact, expression of both the 18 kD and gp35 forms of AR are increased upon removal of the transmembrane sequence. Presumably the carboxyl-terminal cleavage of the transmembrane precursor is a rate-limiting step and this is the first example where a member of the EGF-family has been efficiently expressed in mammalian cells in a partially pre-processed form. Conceivably this strategy for generating efficient expression of soluble growth factors could be applied to other molecules that are first synthesized as transmembrane precursors.

Conditioned media from the AR-transfected CHO cells contained bioactive AR as judged by EGF-R tyrosine phosphorylation in NRHER5 cells; by growth inhibitory assays in MDA-468 (HTB132) and A-431 (CRL1555) cells; growth stimulatory assays in Balb/MK mouse keratinocytes, and AKR-2B cells. These assays and the AR-specific ELISA detect secretion of approximately 3 mg AR/100 mm dish/day.

Figure 6:
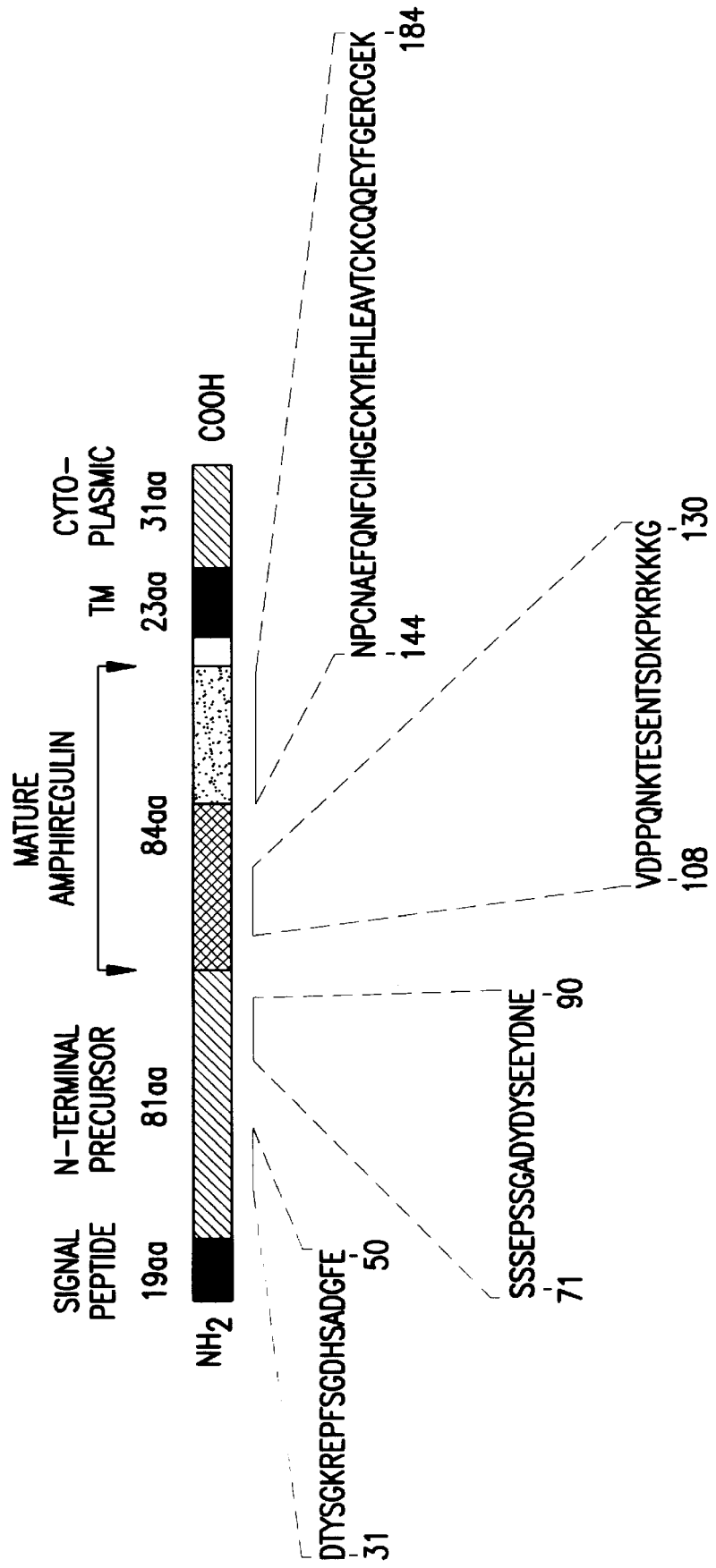
Figures 7A, 7B:
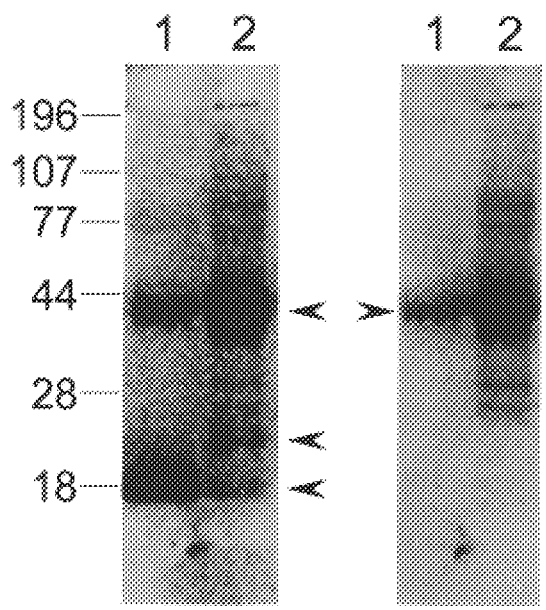

Antibodies directed toward sequences within the AR precursor were generated in rabbits using synthetic peptides as immunogens. The peptide sequences and their relative locations in the AR precursor are shown in FIG. 6. Anti- $AR_{108-130}$ is directed against the hydrophilic/heparin-binding domain of AR and Anti-$AR_{71-90}$ is specific for the N-terminal pro-region. The supernatant and membrane preparations from the CHO clone ARGE 2a-15k were run on reducing 12% SDS-PAGE gels and analyzed by immunoblotting with these AR-specific antipeptide rabbit antisera (FIG. 7). Anti-$AR_{108-130}$ recognizes two soluble forms of 35–40 kD and 18 kD, with approximately 70% of the total AR-specific protein being the smaller 18 kD glycoprotein (FIG. 7, lane 1A). On membrane preparations, this antisera recognized three major forms, a predominant 40–45 kD species, and two fainter bands at 26 kD and 18 kD (FIG. 7, lane 2A). Anti-$AR_{71-90}$ only bound to the 35–40 kD form of AR from the soluble fraction (FIG. 7, lane 1B) and the 40–45 kD integral membrane form of AR (FIG. 7, lane 2B). The bands in the soluble fractions correspond to the forms of AR depicted in FIG. 4E and 4D, while the three species in the membrane fraction (FIG. 7, lane 2A) represent AR forms A, B, and D in FIG. 4.

The immunoblot analysis confirms the various alternatively cleaved products that are predicted from the precursor sequence. AR is first synthesized as a 45 kD integral membrane protein. Differential processing in two regions of the extracellular domain releases the 35–40 kD and 18 kD soluble forms of AR, and leaves the 26 kd and a predicted 8 kD membrane associated protein (see FIG. 4).

Figure 8A:
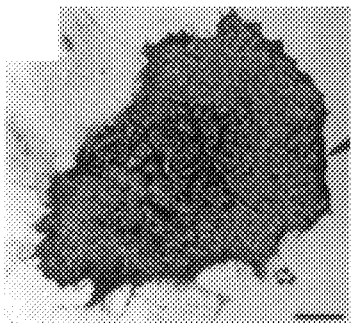
Figure 8B:
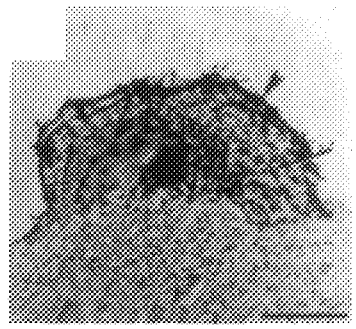
Figure 8C:
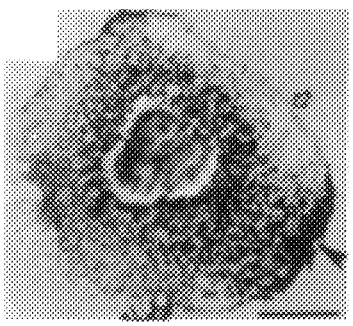
Figure 8D:
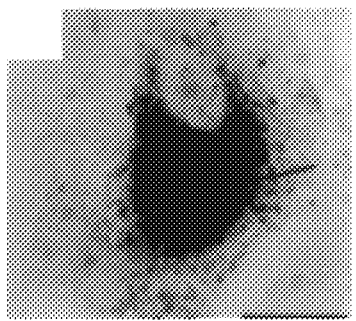

Further verification of the cell surface expression of AR was investigated in adherent MCF-7 cells by immunostaining with an AR-specific monoclonal antibody. In culture, TPA stimulated MCF-7 cells grow in small islands with extensive cell-cell contacts. Cells at the periphery of these islands showed preferential staining with an AR Mab (FIG. 8). The gold label had a fibrillar pattern with enrichment at the cell margin, and often showed intense staining on the edge that was not in direct contact with other cells (FIG. 8A, B, C). Within single cells, the distribution of AR expression was polarized with increased staining on one side of the cell while adjacent membranes were unstained. AR expression was also enhanced at the proliferating edge of cells migrating to fill in a "wound" created by scratching a confluent cell monolayer growing on a glass coverslip. Further experiments were performed to exclude the possibility that the antibody is recognizing receptor bound ligand instead of the integral membrane bound precusor of AR. Treatment of cells with either acid or suramin are known to dissociate ligand-receptor complexes of EGF (Carpenter and Cohen, 1976) and basic FGF (Lee et al., 1989) with their specific cell surface receptors. Subconfluent MCF-7 cells were pretreated either with 50 mM acetic acid (pH 2.8) or 1 mM suramin and then labeled as above. The extent and pattern of staining was unchanged. However, pretreatment of cells with detergent (Triton X-100) resulted in intense perinuclear staining of cells throughout the colony (FIG. 8D).

Figure 8E:
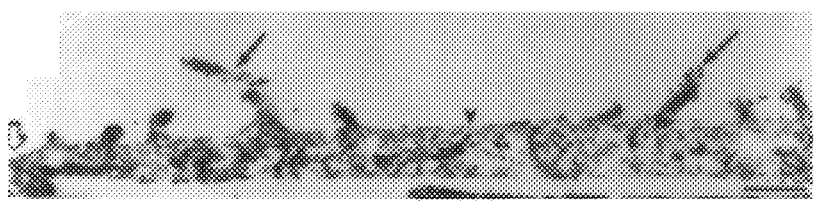
Figure 8F:
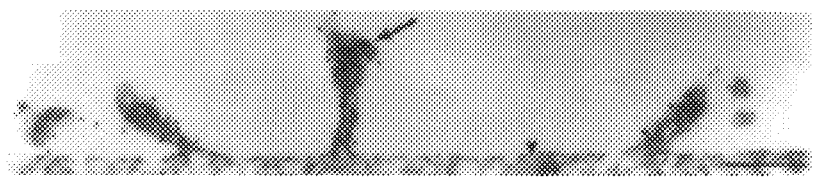

Light microscopy therefore reveals a fibrillar and polarized staining pattern of membrane bound AR at the proliferating edge of the cell islands. To investigate this in more detail, MCF-7 cells were examined by electron microscopy, using a similar immunogold protocol. By this technique, AR was localized almost exclusively to microspikes (FIG. 8E, F, arrows) while underlying smooth membranes were virtually free from label (FIG. 8E, F, arrowheads). The density of microspikes increased at areas of cell-cell contact (FIG. 8E, open arrow) and showed heavy labeling with the AR Mab, particularly at the tips of these membrane protrusions. Microspikes represent a specific microdomain on the cell surface and have been associated with cell-substratum attachment sites, with cell motility, and with points of cell-cell contact (Albrecht-Buehler, 1976). The appearance of these surface protrusions often precedes the formation of membrane ruffles, one of the earliest observed morphologic changes in cells responsive to EGF, TGF-α, or PDGF (Myrdal et al., 1986).

Several members of the EGF family are synthesized as larger precursors with potential transmembrane domains. The membrane spanning domain is located in a similar position, relative to the mature growth factor, in the precursors for EGF, TGF-α, VGF, and AR (FIG. 9). This configuration is associated with secretion of an active EGF receptor binding protein and suggests that the integral membrane form may be necessary for efficient folding of the disulfide bonds. However, our studies with expression of AR constructs that lack the transmembrane and cytoplasmic domains, suggest folding and secretion is in part mediated by the pro-region and the transmembrane domain which may be a means of limiting secretion of soluble growth factor. In addition, recent evidence suggests that these transmembrane precursors may be biologically active even in the absence of processing. Mature EGF (53 amino acids) and TGF-α (50 amino acids) were first discovered as secreted proteins, but uncleaved, high molecular weight forms have also been reported (Bringman et al., 1987). Membrane-bound TGF-α has been detected by immunofluorescence in tumor cells expressing endogenous TGF-α, and integral membrane forms of TGF-α are biologically active and capable of interacting with receptors on adjacent cells (wong et al., 1989; Brachmann et al., 1989).

Identification of various forms of membrane-associated AR, and their localization to the ruffled membranes at the leading edge of the cell colony may be of functional significance in processes such as cell migration or attachment. Possibly the interaction between two membrane bound molecules functions as a type of intercellular communication, thereby triggering a different set of biological effects or a more localized response than seen with secreted growth factors. Anchored expression of AR could serve as an alternative way of delivering its growth regulatory effects. Conceivably this could be acheived through expression of the uncleaved AR precursor in cells, in viral membranes such as vaccinia virus, as liposomes, or as aggregated immunoglobulin fusion constructs. Expression of AR in the human embryonic kidney cell line 293 produces no detectable AR in the active supernatant, but abundant expression of membrane-associated AR. In addition, 293/ARP cells expressing only the membrane bound form of AR can efficiently stimulate EGF-R tyrosine phosphorylation, suggesting this form of AR is also capable of signalling through the EGF-R (FIG. 11, lane 8).

6.2.4. RECOMBINANT EXPRESSION OF MOUSE, RAT, BOVINE AND HUMAN AR

To determine if AR from various species can interact with the EGF-R, the complete coding sequences from cDNA or genomic clones were inserted into the pCDM8 (Invitrogen) expression vector. Specifically the complete coding sequence from human, bovine, and rat cDNA and from human and mouse genomic fragments were inserted into the pCDM8. The expression plasmids were grown in competent MC1061/P3 bacteria, and introduced into COS-1 cells using the DEAE-dextran method (Seed and Aruffo, 1988, Proc. Natl. Acad. Sci. U.S.A. 84: 3365–69). Forty-eight hours after transfection, the cells were washed with serum free DMEM, and serum free supernatants collected for 24 hours. The supernatants were either applied directly to the human AR ELISA, EGF-R tyrosine phosphorylation assay, NRK assay, or A431 growth inhibitory assays. Alternatively, the supernatants were dialyzed against 0.1N acetic acid, dried, and analyzed by 12% SDS-PAGE and immunoblotting with antipeptide rabbit antisera directed against peptides derived from the human AR sequence.

Figure 10A:
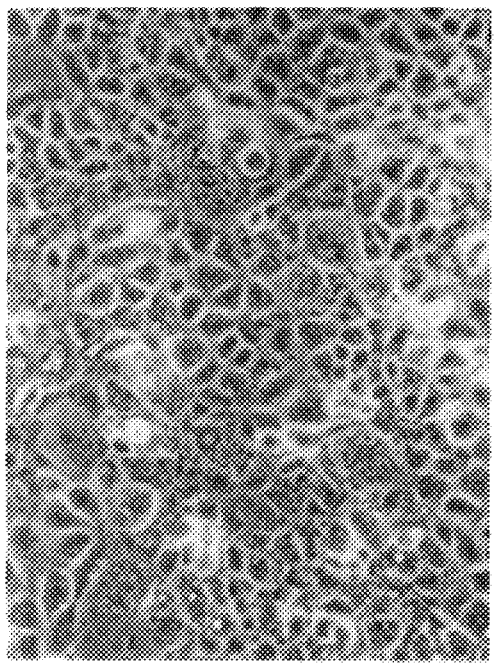
Figure 10B:
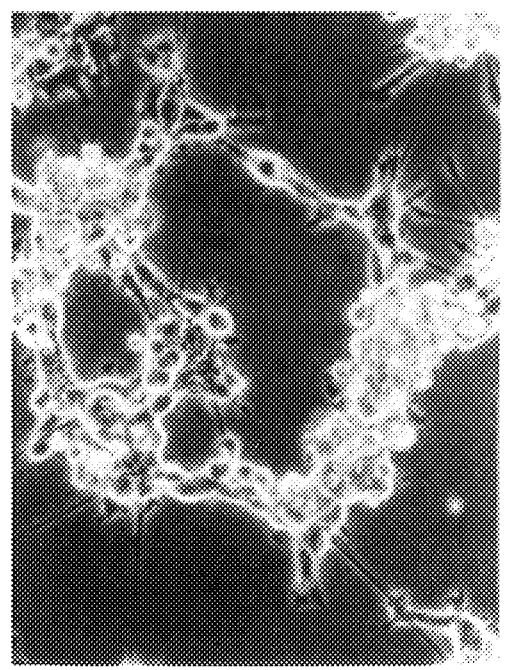

COS cells transfected with these AR constructs were morphologically distinct from controls transfected with the pCDM8 vector alone (FIG. 10). The AR expressing cells formed patches of large cell aggregates, whereas the control cells grew as a confluent monolayer. The cells on the periphery of these aggregates made contact with adjacent cell clumps through long dendritic processes. This transformed morphology may be the result of an auotcrine interaction between AR and the simian EGF-R. It is unclear why cells became detached and grew as aggregates: possibly it was the result of membrane-anchored AR binding to receptors on adjacent cells.

Recombinant AR from mouse, rat, bovine, and human sources were all capable of stimulating tyrosine autophosphorylation of the human EGF-R in NRHER5 cell monolayers (see FIG. 11). In addition, AR from all 4 species stimulate mouse AKR-2B cell proliferation. These findings demonstrate that although rodent, bovine, and human AR show significant differences in their primary amino acid sequence, all four can interact with both the human murine and simian EGF-R. Two additional bioassays for AR activity showed no species specific differences. Specifically, none of the recombinant forms of AR showed synergy with TGF-β in the NRK soft agar assay, suggesting that this unique feature of AR is conserved across species. Second, recombinant AR from all 4 species showed similar inhibition of the A431 tumor cells.

Human, bovine, rat, and mouse AR were tested in an ELISA that uses mouse monoclonal antibody 6R1C generated against a partially refolded peptide from the cysteine-rich domain of human AR. Due to sequence divergence and epitope specificity, this ELISA recognized only human and bovine AR, and not the mouse or rat AR. Immunoblot analysis of recombinant AR from these 4 species revealed that anti-$AR_{71-90}$ (specific for the N-terminal pro-region of AR) reacted with high molecular weight membrane-associated forms from all 4 species (FIG. 12, lanes 1–3, and FIG. 7, lane 2B for human AR), although immunoreactivity to bovine AR (FIG. 12, lane 3) was noticably weaker than to mouse or rat AR (FIG. 12, lanes 1, 2). In contrast Anti-$AR_{108-130}$ sera (directed against the hydrophilic/heparin-binding domain of AR) showed strong reactivity to the membrane-associated forms of bovine and human AR (FIG. 12, lanes 6, 7), but failed to react with AR from rat and mouse (FIG. 12, lanes 4, 5). Therefor, recombinant AR from each of these 4 species appears to be first synthesized as a membrane-associated precursor and subsequent proteolytic cleavage results in the release of the soluble factors.

In summary, these studies suggest that several aspects of AR are well conserved across species: the DNA and amino acid sequence, the exon organization, the transmembrane orientation, processing of the precurosor protein, specific binding to the mouse and human EGF-R resulting in autophosphorylation of the receptor on tyrosine residues, and the growth regulatory activities of AR.

Together, these findings define some of the structural features that distinguish AR from other members of the EGF family.

7. EXAMPLE

PURIFICATION AND CHARACTERIZATION OF AR PRODUCTS EXPRESSED BY EUKARYOTIC CELLS

7.1. MATERIALS AND METHODS

7.1.1. CONSTRUCTION AND EXPRESSION OF CHIMERIC AR-RELATED MOLECULES

The complete coding sequence for the amphiregulin precursor was inserted into a pCDM8 (Invitrogen) based mammalian expression vector. The resulting plasmid (cARP) contains an SV40 origin of replication for expression in COS cells. The complete coding sequence of HB-EGF was isolated by PCR techniques from human placental RNA, and ligated into the same vector, generating cHBEGF. Oligonucleotide primers were designed spanning a natural SstI site in the second cysteine loop of HB-EGF (the location of a conserved leucine between AR and HB-EGF) and extending either 5' or 3' into the sequences of AR or HB-EGF. These primers were used in a PCR protocol on cARP and cHBEGF templates to generated fragments encoding the 5' or 3' portions of each of these genes. The fragments were isolated and ligated to generate cHHA, containing the 5' portion of HB-EGF to the SstI site and the 3' portion of AR beginning at leucine-165, and CAAH, containing the 5' portion of AR to leucine-165 and the 3' portion of HB-EGF.

The expression plasmids were grown in competent MC1061/P3 bacteria, and introduced into COS-1 cells using the DEAE-dextran method. Forty-eight hours after transfection, the cells were washed with DMEM, and 5 ml serum-free supernatants were collected for 24 hours. Supernatants were assayed directly by ELISA or EGF-R tyrosine phosphorylation or aliquots were dialyzed against 0.1N acetic acid, dried, and 1 ml equivalents run on 10% or 15% SDS-polyacrylamide gels.

7.1.2. BIOTIN-LABELING

To assess the purity of the AR 18 kD and gp35 preparations, and as reagents for binding studies, we have biotinylated these ligands. Both forms can be biotin-label on the free amines (lysines) using NHSLC-Biotin (Pierce), or on carbohydrate groups using Biotin-LC-Hydrazide (Pierce). Lysine-labeling was performed on 10 pg AR or gp35 in 100 µl 100 mM sodium bicarbonate, pH 9.6, using 1:20 molar ratio of ligand to biotin. The reaction was incubated for 2 hr at 4° C., then dialyzed against PBS/0.01% sodium azide. Carbohydrate labelling was performed by adding 50 ml of 30 mM $NaIO_4$ to 10 µg ligand in 100 µl labeling solution (100 mM NaOAc, pH 5.5/0.02% sodium azide) and incubating for 30 min at room temperature in the dark. The reaction was stopped by addition of 50 µl 80 mM $Na_2SO_3$, 5 min, RT. 5 mM Biotin-LC-Hydrazide (in labeling solution) was added at a 1:50 molar ratio of ligand to biotin and incubated for 1 hr at room temperature. The reaction was stopped with 250 µl solubilizing solution (100 mM NaOAc, pH 5.5, 1% SDS, 0.02% sodium azide, 2 mM mercaptoethanol), and unincorporated biotin removed by dialysis against PBS/0.01% sodium azide. Approximately 1 ng biotin-labeled ligand was analyzed by 12% SDS-PAGE, transferred to nitrocellulose, blocked in 5% blotto, and incubated with 1:1000 dilution of streptavidin-biotin-horse radish peroxidase. Following several washes with PBS/1% Tween, the biotin-streptavidin complexes were detected using the enhanced chemiluminescence reagents (Amersham).

7.1.3. ELECTROSPRAY IONIZATION MASS SPECTROMETRY

For determination of the molecular weight of the intact protein, the sample (5–10 pmole) was analyzed by a Finnigan-MAT TSQ 700 triple sector quadrupole mass spectrometer equipped with an electrospray ionization (ESI) source and interfaced to a HPLC. A linear gradient of increasing acetonitrile concentration in 0.1% TFA was used for elution of the protein from the reversed-phase column. 2-Methoxyethanol was used as the sheath liquid and nitrogen as the sheath gas. The sample was introduced into the source through a 100 mm diameter stainless steel capillary at a rate of 1 ml/min. Nitrogen gas was heated to 100° C. for the drying gas. A potential difference of 3–4 kV between the needle and counter electrode was applied for ionization. The averaged multiply charged spectrum was collected over the scan range of 50–2000 amu, and molecular weight assigned using the Finnigan-MAT software.

7.1.4. MICROSEQUENCE ANALYSES

Peptides were spotted on polyvinylidene-difluoride (PVDF) membranes (Millipore) and subjected to automated Edman degradation on a gas-phase sequencer built at the City of Hope and equipped with a continuous flow reactor (CFR). The phenylthiohydantoin (PTH) amino acid derivatives were identified by online reversed-phase HPLC.

7.1.5. REDUCTION AND ALKYLATION

The samples were lyophilized to dryness and resuspended in 0.25M Tris buffer at pH 8.5 containing 1 mM EDTA and 6 M guanidine-HCl. Reduction of disulfides was accomplished by addition of 2-beta mercaptoethanol (final concentration of 71 mM) and incubation under argon for 2 hrs. Following reduction, 4-vinylpyridine (370 mM final concentration) was added and the samples again incubated under argon for 2 hrs. The products were purified from the reagents by gel permeation chromatography.

7.1.6. AMINO ACID ANALYSIS

Amino acid composition analyses were performed on a 0.5 μg aliquot using a Beckman system 6300 amino acid analyzer. A vapor phase acid hydrolysis was performed for 12 or 24 hrs using 6M constant boiling HCl containing 0.02% β2-mercaptoethanol. For oxidation of cysteine, a solution of performic acid was prepared by adding 10 ml of 30% $H_2O_2$ to 90 ml of formic acid. This solution was allowed to stand for 2 hrs and then cooled to 0° C. The solution was added to the lyophilized protein and allowed to react for 15 min. Following oxidation, the protein was hydrolyzed and analyzed as described above.

7.1.7. ENZYMATIC DEGLYCOSYLATION

Deglycosylation was accomplished using N-glycosidase F (Boehringer Mannheim) following reduction and alkylation of the proteins. The samples were incubated with 50 units/ml of enzyme for 48 hrs at 37° C. in a 100 mM sodium phosphate buffer at pH 7.5 containing 10 mM EDTA for deglycosylation.

7.2. RESULTS

7.2.1. PRODUCTION AND PURIFICATION OF AMPHIREGULIN (18 kD AND gp35) IN MAMMALIAN CELLS

The dhfr amplified CHO cell line, ARGE 2a-15k expresses high levels of recombinant human AR. These cells were adapted to cell factories and for growth in hollow-fiber bioreactors. A purification scheme was developed for isolation of homogeneous preparations of the 18 kD and 35–40 kD (gp35) forms of recombinant AR. The purification takes advantage of two physical features of AR; heparin binding capacity, and net basic charge. AR binds tightly to both cation exchange and heparin affinity columns permitting a highly selective enrichment through batch elution at early stages of the purification, followed by gradient elution. The high molecular weight form of AR (gp35) binds to these columns with slightly lower affinity than 18 kD AR, and effectively adsorbs to the Q Sepharose anion exchange column. These features can be used to provide a selective enrichment for gp35 away from the 18 kD form of AR (see FIG. 13).

The purification can be followed using the AR ELISA which was found to detect both the 18 kD and 35 kD forms. AR 18 kD and gp35 can be distinguished by immunoblotting with Anti-AR71-90 which recognizes gp35 and not AR 18 kD. Confirmation of active AR is achieved by use of the EGF-R tyrosine phosphorylation assay.

7.2.2. COLLECTION OF CONDITIONED MEDIA FROM TRANSFECTED CHO CELLS

The CHO/ARGE 2a-15k clone was expanded into 10-story cell factories and Cell-PHARM ACM hollow fiber bioreactors (UniSyn Fibertec Corp., San Diego, Calif.). The cells were grown in Dulbecco modified Eagle medium (DMEM) supplemented with 1% fetal bovine serum (FBS), 150 μg L-proline per ml, 100 U/ml penicillin, 100 μg/ml streptomycin, and 15 μM methotrexate. The conditioned supernatant was adjusted to pH 5.5 with 1M acetic acid or 3N NaOH prior to loading onto a cation exchange resin. Alternatively, the supernatant may be concentrated 5–15 fold and dia-filtrated against 40 mM NaP pH 5.0 using an Amicon spiral cartridge with a YM10 filter. Generally, supernatant from cell factories contained 0.4–1.0 mg/l crude AR, whereas the bioreactor contained 3–20 mg/l crude AR.

7.2.3. CATION EXCHANGE CHROMATOGRAPHY

Supernatant containing 5–20 mg/liter crude AR was adjusted to pH 5.0 and loaded onto a cation exchange column (Bakerbond CSx) equilibrated with 40 mM NaP pH 5.0. Generally 5 to 15 ml of resin were used for each milligram of AR. The flow rate was 1–10 ml/min and the chromatography was carried out at room temperature. The column was washed with 20 column volumes of 40 mM NaP, pH 7.0, or until a stable baseline was achieved. The AR was eluted in 10–15 column volumes of 1M NaCl in the same NaP buffer. Fractions were monitored by AR ELISA.

7.2.4. Q SEPHAROSE AND ACRYLIC HEPARIN CHROMATOGRAPHY

The AR pool from the CSx column was diluted to 100 mM NaCl with 40 mM NaP, pH 7.5 and loaded onto a Q-Sepharose column arranged in tandem with an acrylic heparin column. Generally 5–10 mls of Q-Sepharose and 4–8 mls of acrylic heparin are used per 5 mg AR. The flow rate was 1–10 ml/min at room temperature. The columns were washed with 40 mM NaP pH 7.5 until a stable baseline was acheived. The columns were disconnected and the 18 kD form of AR was batch eluted from the acrylic heparin column with 1.5 M NaCl in 40 mM NaP, pH 7.5 until a stable baseline was obtained.

The high-molecular weight form of AR (gp35) was generally retained on the Q-Sepharose resin. This column was then batch eluted with 1M NaCl in 40 mM NaP, pH 7.5, and assayed by AR ELISA.

7.2.5. REVERSE PHASE CHROMATOGRAPHY

AR eluted from the acrylic heparin column was acidified to pH 2–4 with 1M acetic acid and loaded onto a $C_4$ or $C_8$ reverse phase-HPLC column (Vydac). An analytical column was used for less than 1 mg AR, and semipreparative columns for 1–5 mg AR. The chromatographic support was suspended in acetonitrile (MeCN) with 0.15% TFA and equilibrated with 0.15% TFA in water. The flow rate was 0.5–1.5 ml/min for the analytical column and 2.5–5.0 ml/min for the semipreparative column at room temperature. The column was then washed with 0.15% TFA in water. Stepwise elution was performed as follows: (1) 17% MeCN/$H_2O$ with 0.1% TFA until a stable baseline was achieved, (2) a linear gradient of 17–27% MeCN/$H_2O$ with 0.1% TFA in 30–120 min. Fractions of 1–2 min were collected and assayed for AR by ELISA. Two major peaks were seen at approximately 21–23% acetonitrile. A chromatographic profile is shown in FIG. 14.

Reverse phase chromatography of gp35 eluted from the Q Sepharose column was run as above except the elution gradient was from 17–50% MeCN/$H_2O$ with 0.1% TFA in 60 min with the major peak eluting at 36–45 min (approximately 28–33% acetonitrile, see FIG. 15). The flow rate was 0.5 ml/min. A small amount of 18 kD AR eluted in fractions 30–35 (23–28% MeCN).

7.2.6. HEPARIN AFFINITY HPLC

When initial supernatants contained 1% serum or less than 1 mg/l AR, an additional heparin affinity HPLC step was required after reverse phase to obtain homogeneously purified AR. The reverse phase fractions containing AR were pooled and adjusted to pH 7.2 with 3N NaOH, and diluted to <20% organic content by 1:1 or 1:2 dilution with 40 mM NaP, pH7.2. This pool was applied to an FPLC TSK-heparin 5PW column (TosoHaas). The flow rate was 0.5–1.5 ml/min. The column was then washed with 40 mM NaP, pH7 and bound protein was eluted with a 70 ml linear gradient of 01.33M NaCl in 40 mM NaP, pH 7.2. Fractions were tested for AR ELISA reactivity and immunoblotting with AR-specific antisera. The major peak of the 18 kD form of AR eluted at fractions 36–37 (approximately 0.7–0.8M NaCl). A chromatographic profile is shown in FIG. 16.

Heparin HPLC of the reverse phase fractions containing gp35 was performed as above except the elution gradient was from 0–1M NaCl with the gp35 eluting in fractions 41–48 (approximately 0.68–0.8M NaCl, see FIG. 17).

7.2.7. CHROMATOGRAPHIC ANALYSIS OF PURIFIED AR

Aliquots from each stage of the purification scheme for AR were analyzed on a 12% polyacrylamide-SDS gel and visualized by Coomassie stain (FIGS. 18, 19). The purified material eluting from the final reverse phase column migrated as a single broad band of either 18 kD (FIG. 18, lane 4) or 40 kD (FIG. 19, lanes 3, 4). These two forms of AR were also biotinylated and analyzed on 12% SDS-PAGE, again demonstrating the preparations to be very homogeneous (FIG. 20). Aliquots (50–100 μg) of each batch of purified material were analyzed on a narrowbore Vydac C4 column. The 18 kD profile (containing fractions 25–38 from FIG. 14) is shown in FIG. 21A, and the 40 kD profile is shown in FIG. 22. The 18 kD form of AR again eluted in two major peaks, with a slight shoulder preceeding the first peak, whereas the 40 kD form of AR elutied as a single broad peak. The reverse phase pool of 18 kD AR was separated into two pools (representing fractions 25–30 and 31–38 in FIG. 14), and aliquots were again run on the Vydac C4 column (FIG. 21 B,C). Each pool had a distinct profile, with fractions 25–30 eluting at 20% acetonitrile and fractions 31–38 eluting at 22% acetonitrile, demonstrating that each pool contained a distinct and stable form of AR, presumably differing by minor variations of N- or C-terminal residues or in the extent of glycosylation.

7.2.8. AMINO ACID SEQUENCE ANALYSIS OF AR 18 kD FRACTION (f) 25–30

Amino terminal sequence analysis was performed on each of the three (18 kD f25–30 and 31–8, and gp35) recombinant AR samples purfied from the CHO/ARGE 2a cells. The amino terminal 17 residues of AR 18 kD f25–30 corresponded to residues 107–123 in the cDNA sequence of human AR (Plowman et al. Mol. Cell. Biol. 10, 1969–1981, 1990), except that cycle 7 was blank. It is likely that this cycle contained an asparagine-linked oligosaccharide since the cDNA predicted an asparagine at this position and cycle 9 contained a threonine, which would thus conform to the consensus sequence (NXT/S) for N-linked glycosylation. Glycosylated asparagine residues are not observed during sequence analysis due to problems with extracting the ATZ-ASN (oligosaccharide) following cleavage. It should be noted that the other potential glycosylation site (Asn-119) does not appear to be glycosylated as a PTH-Asn was observed in cycle 13 of this run. The only other item of interest in this sequencing run is that the cycle-to-cycle carry-over, or lag, increased following the two prolines in cycles 4 and 5. This is normally observed for Pro-Pro sequences and reflects the difficulty of cleaving proline residues with Edman chemistry.

In order to establish the C-terminus of this sample, amino acid composition and mass were analyzed. Results from the amino acid analyses are shown in Table 1. The compositions indicated presence of methionine and an additional equivalent of lysine and serine compared with the sequence of the 78 amino acid form or native AR originally isolated from TPA-treated MCF-7 cells. While some variation in absolute values between that predicted and that observed are apparent, there is agreement in the general trends. These results suggested that the C-terminus extended past Lys-184 to possibly residue 187.

TABLE I

| Amino | Residue/Mole | | Predicted for residues: | |
|---|---|---|---|---|
| Acid | 12 hr hydrolysis | 24 hr hydrolysis | 107–187 | 107–184 |
| Cys-acid | 5.2 | | 6 | 6 |
| ASX | 10.3 | 10.0 | 9.9 | 9.9 | 9 | 9 |
| THR | 3.6 | 3.7 | 4.1 | 4.2 | 3 | 3 |
| SER | 3.6 | 4.5 | 3.5 | 3.4 | 3 | 2 |
| GLX | 15.2 | 15.2 | 14.8 | 14.7 | 13 | 13 |
| PRO | 4.4 | 4.3 | 4.3 | 4.3 | 4 | 4 |
| GLY | 7.3 | 8.3 | 7.3 | 7.1 | 6 | 6 |
| ALA | 2.7 | 2.9 | 2.6 | 2.7 | 2 | 2 |
| VAL | 2.6 | 2.8 | 3.2 | 3.1 | 3 | 3 |
| MET | 0.7 | 0.7 | 0.8 | 0.8 | 1 | 0 |
| ILE | 1.9 | 1.9 | 2.1 | 2.1 | 2 | 2 |
| LEU | 1.8 | 2.2 | 1.9 | 1.7 | 1 | 1 |
| TYR | 3.3 | 3.2 | 3.5 | 3.4 | 2 | 2 |
| PHE | 3.6 | 3.4 | 3.9 | 3.7 | 3 | 3 |
| HIS | 2.1 | 2.2 | 2.2 | 2.2 | 2 | 2 |
| LYS | 16.4 | 15.3 | 15.8 | 15.8 | 16 | 15 |

TABLE I-continued

| Amino | Residue/Mole | | Predicted for residues: | |
|---|---|---|---|---|
| Acid | 12 hr hydrolysis | 24 hr hydrolysis | 107–187 | 107–184 |
| TRP | 0.0 | 0.0 | 0.0 | 0.0 | 0 | 0 |
| ARG | 5.8 | 5.7 | 5.6 | 5.6 | 5 | 5 |

Amino acid analysis of AR 18 kD f25–30. The residue/mole predicted is based on the cDNA sequence for the indicated residues. Analyses were accomplished in duplicate using 0.5 ug of sample per analysis.

Final confirmation of the C-terminus was accomplished using electrospray mass spectrometry following the reduction, alkylation, and deglycosylation of the sample. In electrospray mass spectrometry the sample is multiply charged due to the protonation of basic residues, histidines, and the amino terminus. This multiply charged spectra indicated some heterogeneity in the sample with the appearance of additional peaks of higher and lower masses than the major, numbered peaks. Deconvolution of these ions resulted in the assignment of the parent ion masses. The main ion observed had a mass of 10,053, which was 2 amu higher (0.02% mass deviation) than that predicted for AR residues 107–187. Expansion of this molecular ion region revealed the heterogeneity in the sample, most of which was accounted for by partial alkylation of the two histidine residues resulting in the increase of 106 amu for each pyridylethyl group added (ions noted at 10,159 and 10,265 amu). In addition to these masses, an additional one at mass 9,939 was observed. This ion reflected a slight contamination of f31–38 (which has a mass of 9,923, see below), assuming an oxidation of the methionine-186. Taken together with the N-terminal sequence data and the amino acid compositions, the mass data confirmed that the AR sample in f25–30 is 81 amino acids long, beginning with Val-107 and ending with Lys-187.

7.2.9. AMINO ACID SEQUENCE ANALYSIS OF AR 18 kD f31–38

The amino terminal 17 residues of AR 18 kD fractions 31–38 were identical to those in fractions 25–30, and corresponded to residues 107–123 in the cDNA sequence of human AR (Plowman et al. Mol. Cell. Biol. 10, 1969–1981, 1990). Also like f25–30, the protein in this fraction appeared to be glycosylated at residue 7 (Asn-113), but not at residue 13 (Asn-119). Results from the amino acid compositions of f31–38 are summarized in Table 2. These compositions appeared nearly identical to those obtained on f25–30, and revealed the presence of one equivalent of methionine and a higher amount of lysine. To establish the C-terminus of AR 18 kD f31–38, electrospray mass spectrometry was used. The spectra for the multiply charged ions also revealed the presence of some heterogeneity in the sample. Deconvolution of this spectra allowed assignment of the molecular mass as 9,923 amu. The heterogeneity was determined again to involve over alkylation of the sample. The determined mass corresponded to that predicted for residues 107–186 in the human AR sequence, deviating from that predicted (9,921.5) by only 1.5 amu (0.01%). Even though the compositions of both AR 18 kD f25–30 and f31–38 revealed the presence of equal amounts of lysine, the accuracy of electrospray mass spectrometry provides compelling evidence that the two reverse phase peaks of AR 18 kD differ at the C-terminus with f31–38 lacking Lys-187.

TABLE II

| Amino | Residue/Mole | | Predicted for residues: | |
|---|---|---|---|---|
| Acid | 12 hr hydrolysis | 24 hr hydrolysis | 107–187 | 107–184 |
| Cys-acid | 4.8 | | 6 | 6 |
| ASX | 9.9 | 10.1 | 10.0 | 9.8 | 9 | 9 |
| THR | 3.7 | 3.7 | 4.3 | 4.2 | 3 | 3 |
| SER | 3.9 | 3.5 | 3.3 | 3.3 | 3 | 2 |
| GLX | 14.8 | 14.9 | 14.9 | 14.8 | 13 | 13 |
| PRO | 4.4 | 4.6 | 4.5 | 4.3 | 4 | 4 |
| GLY | 7.3 | 6.9 | 6.9 | 6.9 | 6 | 6 |
| ALA | 2.6 | 2.6 | 2.5 | 2.5 | 2 | 2 |
| VAL | 2.4 | 2.2 | 2.9 | 2.9 | 3 | 3 |
| MET | 0.7 | 0.7 | 0.8 | 0.8 | 1 | 0 |
| ILE | 1.8 | 1.8 | 2.0 | 2.3 | 2 | 2 |
| LEU | 2.0 | 1.7 | 1.5 | 2.1 | 1 | 1 |
| TYR | 3.3 | 3.1 | 2.8 | 2.9 | 2 | 2 |
| PHE | 3.7 | 3.7 | 2.9 | 3.3 | 3 | 3 |
| HIS | 2.1 | 2.1 | 2.2 | 2.2 | 2 | 2 |
| LYS | 16.4 | 17.1 | 16.9 | 16.6 | 15 | 15 |
| TRP | 0.0 | 0.0 | 0.0 | 0.0 | 0 | 0 |
| ARG | 5.6 | 5.6 | 5.9 | 5.6 | 5 | 5 |

Amino acid analysis of AR 18 kD f31–38. The residue/mole predicted is based on the cDNA sequence for the indicated residues. Analyses were accomplished in duplicate using 0.5 ug of sample per analysis.

7.2.10. AMINO ACID SEQUENCE ANALYSIS OF gp35

The amino terminal 20 residues of 40 kD gp35 corresponded to residues 27–46 in the human AR cDNA sequence, with the exception that cycle 4 (predicted to be Asn-30) was blank. Again it is proposed that this position contained a glycosylated asparagine residue. No other differences in the amino acid sequence predicted by the cDNA data and that determined by direct sequencing was observed. Results from the amino acid analysis for gp35 are shown in Table 3. It was difficult to obtain an accurate mass measurement on the sample (see below) and thus a molar value for amount of sample hydrolyzed and analyzed was not calculated. Consequently, the results are expressed in mole percent, which is different from how the compositions for f25–30 and f31–38 were expressed (Tables 1 and 2). The most obvious changes in comparing the mole percent yields of gp35 with those of f25–30 and f31–38 are a substantial increase in the serine content and a reduction in the amount of lysine. Other changes are also evident, but not as dramatic. As stated previously, we were unable to obtain an accurate mass on deglycosylated gp35 using electrospray mass spectrometry. The reason for this appears to be related to an extreme amount of heterogeneity in the sample, which may be related to presence of O-linked sugars, glycosaminoglycans, or sulfation of the consensus tyrosine sulfation sites indicated in the cDNA sequence. The reconstructed ion current spectra (i.e. the ions generated by ionization of the sample as a function of scan number) contained a large burst of ions in scans 350–390. We were not able to deconvolute the spectra, due to its complexity, and therefore cannot identify the probable C- terminus of the gp35 sample.

TABLE III

| Amino Acid | Mole % | | | |
|---|---|---|---|---|
| | 12 hr hydrolysis | | 24 hr hydrolysis | |
| Cys-acid | 3.2 | | | |
| ASX | 13.1 | 13.0 | 12.9 | 12.9 |
| THR | 3.4 | 3.5 | 3.8 | 3.8 |
| SER | 12.3 | 12.3 | 11.5 | 11.5 |
| GLX | 16.5 | 16.5 | 16.6 | 16.8 |
| PRO | 6.5 | 6.5 | 6.5 | 6.5 |
| GLY | 8.0 | 8.3 | 8.0 | 8.0 |
| ALA | 2.8 | 2.8 | 2.8 | 2.8 |
| VAL | 4.4 | 43 | 49 | 49 |
| MET | 0.6 | 0.6 | 1.0 | 0.9 |
| ILE | 2.8 | 2.8 | 3.0 | 3.1 |
| LEU | 2.6 | 2.7 | 2.4 | 2.5 |
| TYR | 5.8 | 5.6 | 5.2 | 5.2 |
| PHE | 3.3 | 3.2 | 3.3 | 3.3 |
| HIS | 1.9 | 1.9 | 1.9 | 1.9 |
| LYS | 10.9 | 10.8 | 10.8 | 10.7 |
| TRP | 0.0 | 0.0 | 0.0 | 0.0 |
| ARG | 5.1 | 5.1 | 5.1 | 5.2 |

Amino acid analysis of gp35. The values are expressed in mole percent since we were unable to obtain an accurate mass measurement for gp35. Analyses were performed in duplicate using 0.5 ug of sample per analysis.

7.2.11. SUMMARY OF THE ANALYSIS OF THE VARIOUS FORMS OF RECOMBINANT AR (1) The sequence of AR 18 kD f25–30 is 81 amino acids long and starts at residue Val-107 in the human AR cDNA sequence, has one glycosylation site at Asn-113, and ends at Lys-187.

(2) The sequence of AR 18 kD f31–38 also starts at residue Val-107, also has one glycosylation site at Asn-113, but ended at Met-186, therefore containing 80 amino acids.

(3) The amino terminus of gp35 is at Leu-27 and there appears to be one glycosylation site in the first 20 residues (Asn-30). An accurate mass measurement on gp35 was not obtained due to the complexity of the spectra. Analysis of gp35 using repetitive enzymatic digestions, peptide mappings, and sequence analyses should permit determination of its C-terminus.

7.2.12. gp35 IS A LIGAND FOR THE EGF-RECEPTOR gp35 is a 35–40 kD soluble glycoprotein derived by alternate processing of the AR transmembrane precursor. We have purfied recombinant gp35 to homogeneity and have determined the sequence of its 20 N-terminal residues. This analysis demonstrates that gp35 has an additional N-terminal pro-region of 80 amino acids when compared to the 18 kD form of AR. This pro-region contains a highly charged, glycine-rich sequence, at least one N-linked glycosylation site, several potential O-linked glycoslyation sites, glycosaminoglycan attachment sites, and tyrosine sulfate consensus motifs. Even though gp35 contains the complete bioactive portion of AR, any of these post-translational modifications could alter its receptor binding specificity. To assess the bioactivity of gp35, the homogeneously purified protein was applied to the EGF-R tyrosine autophosphorylation assay. gp35 shows effective activation of the EGF-R tyrosine kinase at between 100–500 ng/ml (FIG. 11). EGF-R binding competition assays were performed using $^{125}$I-EGF (FIG. 23). These studies demonstrate that gp35 has a reduced affinity to EGF-R compared to EGF and the 18 kD form of AR. Therefore, gp35 is capable of binding and activating the human EGF-R, but with an affinity lower than that of the 18 kD form of AR. Conceivably, these differences could translate into altered activities through the EGF-R or with other members of the EGF-R family.

8. EXAMPLE

PURIFICATION AND CHARACTERIZATION OF AR EXPRESSED BY PROKARYOTIC CELLS

8.1. RESULTS

8.1.1. PRODUCTION AND PURIFICATION OF AMPHIREGULIN IN BACTERIAL CELLS

Bacterial expression of AR was first performed using a periplasmic secretion vector (pTacAPHILE) based on the tac promoter and the alkaline phosphatase leader sequence. Most of the recombinant protein produced by this system was held up as periplasmic inclusion bodies. Nominal amounts of active AR was recovered from the supernatants after 2–3 days induction. Conceivably the hydrophilic domain of AR disrupts translocation across the periplasmic membrane resulting in insoluble inclusion bodies. To circumvent these difficulties a bacterial expression system was selected for production of an inculsion body containing the unfused AR preceeded by an initiating methionine. However, this method requires solubilization and refolding of the recombinant protein.

Plasmid $pP_L$-Lambda is a thermoinducible bacterial expression vector that contains the strong and tightly regulated bacteriophage $P_L$ promoter. Initial difficulties in obtaining active AR from this system were overcome by recognition of two physical features of AR that are quite distinct from other EGF receptor-binding proteins. First, the highly basic, unglycosylated AR has a very high isoelectric point (pI 10.1), compared to that of EGF (pI 4.5) and TGF-α (pI 5.8). Most refolding protocols for this family of growth factors are performed at neutral pH. Under these conditions, EGF and TGF-α have a net negative charge whereas AR would have a highly positive charge. To compensate for the high pI of AR, a calculation was made that at pH 11.0, AR would have a net negative charge comparable to that used for refolding of EGF and TGF-α under neutral conditions. This prediction was confirmed by comparing the efficiency of AR refolding over a range of pH 7–11. Maximal activity was seen following refolding in CAPS buffer, pH 11.0. Second, AR is truncated on the C-terminus compared with EGF and TGF-α. The major soluble forms of AR identified from mammalian sources has only 3–6 amino acid residues after the sixth cysteine compared with TGF-α and EGF which extend 7–12 residues past the cysteine, respectively. In addition, this region includes a conserved leucine residue that is required for binding of EGF and TGF-α to the EGF-R. Native AR binds the EGF-R, yet lacks this C-terminal extension and the leucine residue. The initial constructs contained a nucleotide sequence encoding the 78 amino acid form of AR ($Val_{107}$-$Lys_{184}$) preceeded by a methionine. This construct only showed an approximate 1% refolding efficiency. Inclusion of an additional 4 C-terminal residues from the AR precursor (Ser-Met-Lys-Thr) (SEQUENCE ID NO:29) in this construct increased the refolding efficiency 10–40-fold. This construct (pPLMASMKT) was then used for all subsequent studies (FIG. 24, 25). Analysis of other AR-based expression constructs differing only in the sequence of these final four residues, suggests that the improved refolding depends more on the number of C-terminal residues than on the actual sequence.

8.1.2. CONSTRUCTION OF THE pPLMASMKT BACTERIAL EXPRESSION VECTOR

Plasmid $pP_L$-Lambda (obtained from Pharmacia) is a thermoinducible bacterial expression vector that contains the bacteriophage $P_L$ promoter and regulatory elements. The promoter is thermoregulated in N4830-1 bacteria containing the temperature-sensitive cI857 repressor. At 27°–30° C. the promoter is repressed and at 38°–42° C. the repressor activity is destroyed, permitting transcription from the $P_L$ promoter. This vector also contains the phage anti-termination function, N, and the N utilization (nut) site (FIG. 24). These features permit N gene expression from the host and inhibits transcription termination.

$pP_L$-Lambda was modified to remove the EcoRI, BamHI, and SmaI sites just upstream from the $P_L$ promoter by digestion with EcoRI and SmaI ligation following digestion with SmaI. The following expression unit was then isolated by PCR techniques from the human AR cDNA and cloned into the unique HpaI site within the N gene to generate pLMASMKT: (1) stop codons in all three reading frames, (2) lac and Cro gene Shine-Delgarno ribosome binding sites, (3) unique BglII restriction site, (4) initiating methionine, (5) nucleotide sequence encoding 82 amino acids of the AR precursor ($Val_{107}$-$Thr_{188}$), (6) stop codon and unique EcoRV, and XbaI restriction sites, (7) transcription termination sequences (see FIG. 24). The sequence of this expression unit is shown in FIG. 25. A related construct, pLMAAAT, was generated in a similar manner as with pLMASMKT, except the PCR primers were designed to insert Asp-Leu-Leu-Ala (SEQ ID NO:28) at the C-terminus instead of Ser-Met-Lys-Thr (SEQ ID NO:29). The final four amino acids of pLMAAAT correspond to the C-terminal sequence of human TGF-α, and includes a conserved leucine that has been shown to be required for high affinity binding of EGF and TGF-α to the EGF-R.

8.1.3. ISOLATION AND SOLUBILIZATION OF AR INCLUSION BODIES

Plasmids pLMASMKT and pLMAAAT were transformed into competent *E. coli* N4830-1 and grown at 30° C. in 1 liter LB media with 50 ug/ml ampicillin to an $OD_{600}$ of 0.7. Cultures were then induced by incubation at 42° C. for 18–24 hr. Following induction, cells were harvested by centrifugation at 5000×g, washed in STE buffer (50 mM Tris, pH 8.0/200 mM NaCl/2 mM EDTA). The pellet was resuspended in STE containing 2 mM mercaptoethanol, and lysed by addition of 0.2 mg/ml lysozyme followed by addition of Triton X-100 and Zwittergent (CalBiochem) to 1%. To ensure lysis and solubilization of non-inclusion body protein, the preparation was subjected to sonication for 2 min, followed by centrifugation at 13000×g for 30 min in Beckman SW28 rotor. The slurry was washed in 20 ml STE and respun at 13000K for 30 min at 4° C. The inclusion body pellet was resuspended in 6M guanidine-HCl (GuHCl)/50 mM CAPS, pH 11.0.

8.1.4. RENATURATION OF SOLUBILIZED AR INCLUSION BODY PREPARATION

The AR inclusion body preparation was diluted to 60 mM GuHCl with 50 mM CAPS, pH 11.0/1 mM EDTA/1.25 mM reducing glutathione/0.5 mM oxidizing glutathione/0.001% tween 20. The final protein concentration was 50–100 μg/ml by Biorad protein assay. Refolding was acheived by incubation at 4° C., 18–24 hr. The solution was then dialyzed against 50 mM NaP, pH 7.5. The buffer exchanged material was successively filtered through 5 Mm, 0.45 μm, and 0.22 mm filters or subjected to 60,000×g centrifugation prior to cation exchange chromatography. Alternatively, the refolded material was buffer exchanged by ultrafiltration through a 10,000 MW. membrane against 3-volumes 50 mM NaP, pH 7.5.

8.1.5. CATION EXCHANGE CHROMATOGRAPHY

Cleared, refolded bacterially produced AR was sequentially loaded onto a Q-Sepharose column followed by a cation exchange column (Bakerbond CSx) equilibrated with 40 mM NaP pH 7.0. The flow rate was 1.25 ml/min and the chromatography was carried out at room temperature. The column was washed with 20 column volumes of 40 mM NaP, pH 7.0, or until a stable baseline was achieved. The AR was eluted with a 50 ml linear gradient of 0.2–1M NaCl in 40 mM NaP, pH 7.0. Fractions were tested for AR ELISA reactivity, by immunoblotting, and EGF-R tyrosine autophosphorylation. Peak AR activity was in fractions 20–24 (520–580 mM NaCl). A chromatographic profile is shown in FIG. 26.

8.1.6. HEPARIN AFFINITY HPLC

The peak AR fractions from cation exchange chromatography were pooled, diluted to 0.2M NaCl with 40 mM NaP, pH 7.0, and applied to an FPLC TSK-heparin 5PW column (TosoHaas). The flow rate was 1 ml/min. The column was then washed with 40 mM NaP, pH 7.0 and bound protein was eluted with a 30 ml linear gradient of 0–1.0M NaCl in 40 mM NaP, pH 7.0. Fractions were tested for AR ELISA reactivity, by immunoblotting, and EGF-Receptor tyrosine autophosphorylation. Peak AR activity was in fractions 25–26 (approximately 800 mM NaCl). A chromatographic profile is shown in FIG. 27.

8.1.7. ANALYSIS OF AR PURIFIED FROM BACTERIA

Aliquots from the pLMSMKT AR inclusion body preparation, CSx peak, and heparin HPLC peak were analyzed by 15% SDS-PAGE and visualized by Coomassie stain (FIG. 28). The unglycosylated bacterial AR-SMKT migrated at 14 kD, consistent with the N-glycanase treated native AR. Immunoblot analysis with anti-$AR_{108-130}$ confirmed the 14 kD species to be AR. pLMAAAT showed an expression, size, and purification profile similar to that of pLMSMKT. AR activity was measured using the AR-specific ELISA, murine fibroblast growth stimulation, and EGF-R tyrosine phosphorylation assay. AR-SMKT showed a dose dependent response in the EGF-R tyrosine phosphorylation assay (FIG. 29, lanes 3–5), which was sensitive to inhibition by 30 ug/ml heparin (FIG. 29, lanes 6–8). Likewise, the bacterially produced AAAT stimulated EGF-R tyrosine phosphorylation (FIG. 29, lanes 12–14), and this activity was again blocked by the presence of heparin sulfate (FIG. 29, lanes 15–17). EGF-induced trysoine phosphorylation of EGF-R was unaffected by heparin sulfate (FIG. 29, lane 9).

Bacterially produced AR-SMKT was found to inhibit the binding of $^{125}$I-EGF to NRHER5 membranes as well as to live cells (FIG. 23). A 50% inhibition of $^{125}$I-EGF binding to NRHER5 membranes was seen at approximately 0.1 nM EGF (0.1 ng/well), 100 nM native or recombinant AR-18 kD (100 ng/well), >300 nM gp35 (>500 ng/well), 150 nM AR-SMKT (100 Ang/well), 1.5 nM AAAT (1 ng/well). Unlabeled EGF, and AAAT completely inhibited $^{125}$I-EGF-receptor interaction at higher concentrations, whereas the maximum competition with native or recombinant AR-18 kD, and bacterial AR-SMKT was about 85%. These results suggest the following: (1) AR has a lower affinity for EGF-R than EGF, (2) native and recombinant glycosylated AR are equipotent in this assay, (3) unglycosylated AR-SMKT is very similar to native and recombinant AR-18 kD based on its EGF-R competition curve in addition to its potency in stimulating EGF-R tyrosine phosphorylation, (4) AR has a relatively lower affinity than EGF to NR5HER5 membranes as compared with A-431 membranes, (5) AAAT has a 10–100-fold higher affinity to the EGF-R than AR-SMKT, (6) gp35 binds EGF-R with low affinity.

The NRHER5 cells represent a "clean" assay line for human EGF-R, since the parent NR6 cells lack any receptors for EGF and AR, and retroviral transfection into these cells has resulted in dramatic overexpression of the EGF-R. The tyrosine phosphorylation and competition binding assays using NR5HER5 cells are therefore not complicated by potential binding to EGF-R related molecules. In addition, NR5HER5 and A-431 cells may have different profiles of cell surface proteoglycan expression, which may affect the measured affinity of AR binding. Interestingly, AR has an affinity to the EGF-R approximately 10–1000 times lower than does EGF, yet AR stimulates EGF-R tyrosine phosphorylation at concentrations similar to that of EGF. In addition, inclusion of a C-terminal leucine in the AR-related construct AAAT, results in a molecule that competes as well as EGF for binding the EGF-R. These studies suggest that part of the reduced EGF-R binding characteristics of AR compared to EGF is the result of its lack of this conserved C-terminal leucine. However, even in the absence of this leucine, AR is a potent ligand for the EGF-R, whereas loss or alteration of the C-terminal leucine in EGF or TGF-α, severely reduces or eliminates their binding and signaling through the EGF-R.

9. EXAMPLE

PRODUCTION OF AR-SPECIFIC ANTIBODIES

9.1. MATERIALS AND METHODS

9.1.1. MONOCLONAL ANTIBODY PRODUCTION

BALB/c female mice were used for immunization with purified recombinant AR-18 kD purified from CHO/ARGE 2a cells. 10 µg of AR-18 kD in complete Freund's adjuvant was used per injection into the mouse footpad. Subsequent boosts were performed every 2 weeks using 10 µg AR in complete Fruend's. One week following the second boost, the popliteal nodes were isolated and fused as previously described (Radka, S. F. et al., 1982, J Immunol 128:2804–2806). Hybrids resulting from the fusions were screened for AR-specific antibody production by a solid-phase ELISA essentially as described above, except AR was plated at 10 ng/well.

9.2. RESULTS

9.2.1. AR-NEUTRALIZING ANTIBODY ASSAY

Aliquots of uncloned hybridoma supernatants were diluted 1:1 in DMEM and incubated with 100 ng/ml AR for 5 min at room temperature. This MAb-ligand mixture was then added to a monolayer of NRHER5 cells and the EGF-R tyrosine phosphorylation assay carried out as described above.

9.3. AR MAB PRODUCTION AND CHARACTERIZATION

A series of monoclonal antibodies directed against AR were generated by immunizing mice with purified recombinant human AR-18 kD. Hybridoma supernatants were screened using an ELISA with 10 ng AR/well. Thirty AR-specific MAbs were identified from 2916 hybridomas. Each of these 30 MAbs were tested for the following: (1) immunoprecipitation of $^{35}$S-labeled CHO/ARGE 2a supernatants; (2) blocking of AR-mediated tyrosine phosphorylation of EGF-R in NRHER5 cells; (3) ELISA activity against recombinant human, bovine, mouse, and rat AR, unglycosylated AR-SMKT, TGF-α, EGF, HB-EGF (heparin binding-EGF), and two chimerics based on human AR and HB-EGF (HHA, AAH). A summary of these results is shown in Table 4. All thirty MAbs recognized both AR-18 kD and AR-SMKT, however 6 showed stronger ELISA reactivity to the bacterial AR-SMKT. These results suggest that all MAbs recognize epitopes to the protein core of AR, since they react to both glycosylated and unglycosylated AR. Eight MAbs immunoprecipitated soluble forms of AR, and two of these preferentially recognized the 18 kD form over gp35. Five MAbs were capable of competing for the binding of AR to EGF-R, based on the EGF-R tyrosine phosphorylation assay. These hybridoma supernatants neutralized 100 ng/ml AR-18 kD (FIG. 30) or AR-SMKT, but all failed to block EGF-R tyrosine phosphorylation by EGF, TGF-α, or HBEGF, suggesting they were potent and specific inhibitors of human AR. None of the MAbs reacted by ELISA to EGF, TGF-α, or bovine AR, but initial analysis suggests that 1 or 2 cross-react to mouse and rat AR or HB-EGF. Eight MAbs recognized HHA, a recombinant chimeric where the N-terminal portion is derived from HB-EGF and the C-terminal portion is from AR. A total of 7 MAbs recognized AAH, a recombinant chimeric where the N-terminal portion is derived from AR and the C-terminal portion is from HB-EGF—the reverse of HHA. Preliminary screening suggests only 1 MAb recognizes both HHA and AAH, and this is also the MAb that appears to recognize HB-EGF. This analysis permits an initial domain mapping of the MAb epitopes, and resulted in the selection of 12 hybridomas for cloning and further characterization. Intriguingly, all the strong blocking MAbs recognized HHA and not AAH, suggesting that a major neutralizing epitope for AR lies distal to leucine-165 (based on the AR precursor sequence), encompassing the "third" cysteine-loop of mature AR. However, one crude hybridoma superantent was able to partially block AR activation of EGF-R, yet failed to react to either HHA or AAH, suggesting it may recognize a distinct neutralizing epitope. Further characterization of the neutralizing potential of these MAbs and their suitability for immunostaining can be done following cloning and purification.

This diverse panel of AR-specific MAbs will facilitate studies of AR processing, expression, tissue localization, and function. Specifically the neutralizing MAbs may be used to block certain types of AR-mediated or AR-dependent cell proliferation. Examples of such hyperproliferative pathologies include, but not limited to, psoriasis, proliferative breast disease, epithelial carcinomas, glomerlonephropathies, and atherosclerotic lesions.

10. EXAMPLE

AR STABILITY AND RELEASE IN DELIVERY SYSTEMS

10.1. AMPHIREGULIN FORMULATION AND DELIVERY

A series of studies was undertaken to evaluate the stability of both mammalian and bacterial AR in different formulations. Samples were placed in 10, 25 and 50 mM buffers ranging in pH from 4.5 to 9.5 which contained NaCl at concentrations of 50 or 150 mM. The effects of different stabilizing additives including Tween-80 (a non-ionic surfactant), glycerol, sucrose, mannitol, polyvinylpyrrolidone and polyethylene glycol were also studied. The different formulations containing AR were subjected to refrigeration at 4° C., incubation at 50° C. or repeated freeze/thaw cycles at −70° C. The AR was evaluated at time zero and at specified times after the treatments by SDS-PAGE, reverse phase HPLC, ELISA and a phosphorylation assay. Based on the results of these studies, the preferred formulation for bacterial and mammalian AR was found to be 10 mM sodium phosphate, 150 mM NaCl with 0.01% Tween-80 at pH 6.5. The protein was stable when stored in this formulation at either 4° C. or −70° C. for more than 1 month.

Amphiregulin was incorporated into DuoDERM hydroactive paste and a 30% (w/w) Pluronic polyol gel to evaluate the utility of these carriers as sustained release formulations. In vitro release studies were performed on these systems and assayed by ELISA. FIG. 31 shows the in vitro mean cumulative percent release (obtained with a Franz diffusion cell at 37° C.) of mammalian and bacterial AR from Pluronic gels loaded with 100 μg AR/g gel. The gel sustained the AR release for a period of at least 48 hrs. Between 80 and 90% of the incorporated AR was released from the gel. The released material was found to be active when assayed for its ability to phosphorylate the EGF receptor. FIG. 32 shows the cumulative amount of bacterial AR released from Pluronic gel over time from gels loaded with two different concentrations of AR. This figure demonstrates that the dose of AR delivered from the gel can be varied by varying the initial amount of AR incorporated into the delivery system. FIG. 33 shows the in vitro cumulative percent release of bacterial AR from DuoDERM paste over time. The release was sustained for approximately 8 hrs in this system. By incorporating the AR into different carriers, the rate of delivery can be controlled. The sustained release systems described above can be used for topical delivery of AR for the treatment of skin disorders such as full or partial thickness wounds. The Pluronic gel formulation could also be used for parenteral delivery of AR. The AR could be encapsulated into biodegradable polymeric matrices such as poly(lactide-co-glycolide) microspheres for prolonged release parenteral administration. In addition, a microencapsulated form of AR could be used in an oral delivery system to protect the AR from inactivation due to low pH and proteolytic cleavage in the stomach.

11. DEPOSIT OF MICROORGANISMS

The following microorganisms have been deposited with the Agricultural Research Culture Collection, Northern Regional Research Center (NRRL) and have been assigned the following accession numbers:

| Microorganism | Plasmid | Acession No. |
| --- | --- | --- |
| Escherichia coli HB101 | pAR1 | B-18438 |
| Escherichia coli HB101 | pARH12 | B-18439 |
| Escherichia coli HB101 | pARH6 | B-18440 |
| Escherichia coli JM109 | pTacAPAR1 | B-18441 |
| Escherichia coli JM109 | pTacAPHILE | B-18442 |

The present invention is not to be limited in scope by the cell lines deposited or the embodiments disclosed herein which are intended as single illustrations of one aspect of the invention and any which are functionally equivalent are within the scope of the invention. Indeed, various modifications of the invention, in addition to those shown and described herein, will become apparent to those skilled in the art from the foregoing description. Such modifications are intended to fall within the scope of the appended claims.

It is also to be understood that all base pair and amino acid residue numbers and sizes given for nucleotides and peptides are approximate and used for the purposes of description.

What is claimed is:

1. A substantially purified bovine amphiregulin, AR, protein having the amino acid sequence (SEQ ID NO:30):
ValValLysProLysLysAsnLysThr-GluSerGluLysThrSerAspLysProLysArg LysLysLysGlyGlyLysAsnGlyLysAsnArgArgAsnArgLysLysLysAsnLeuCysAspThrGluPheGlnAsnPheCysIle-HisGlyLysCysThrPheLeuGluGlnLeuGlu ThrValSerCysGlnCysTyrProGluTyrPheGly-GluArgCysGlyGluLys.

2. The bovine AR protein of claim 1, further containing four additional amino acid residues at the carboxy-terminal end of the protein, said additional amino acid residues enhancing the folding efficiency of said AR protein.

3. A substantially purified essentially of the amino acid sequence (SEQ ID NO:31):
ValIleLysProLysGluAsnLysThr-GluGlyGluLysSerSerGluLysProLysArg LysLysLysGlyGlyLysGlyGlyLysGlyArgArgAsnArgLysLysLysLysAsnPro CysAlaAlaLysPheGlnAsnPhe-CysIleHisGlyGluCysArgTyrIleGluAsnLeu GluVal-ValThrCysHisCysHisGlnAspTyr-PheGlyGluArgCysGlyGluLys.

4. The rat AR protein of claim 3, further consisting of a sequence of four additional amino acid residues at the carboxy-terminal end of the protein, said additional amino acid residues enhancing the folding efficiency of said AR protein.

5. A substantially purified mouse AR protein having the amino acid sequence (SEQ ID NO:32):
ValIleLysProLysLysAsnLysThr-GluGlyGluLysSerThrGluLysProLysArg LysLysLysGlyGlyLysAsnGlyGluGlyArgArg-
AsnLysLysLysLysAsnProCys
ThrAlaLysPheGlnAsnPheCysIle-
HisGlyGluCysArgTyrIleGluAsnLeuGlu ValValThr-
CysAsnCysHisGlnAspTyrPheGly-
GluArgCysGlyGluLys.

6. The mouse AR protein of claim 5, further containing four additional amino acid residues at the carboxy-terminal end of the protein, said additional amino acid residues enhancing the folding efficiency of said AR protein.

7. The AR protein of claim 2, 4 or 6, wherein the sequence of four additional amino acide residues is Ser-Met-Lys-Thr (SEQ ID NO. 29).

8. A substantially pure human amphiregulin polypeptide having the sequence (SEQ ID NO:33):

ValValLysProProGlnAsnLysThr-
GluSerGluAsnThrSerAspLysProLysArg LysLysLysG-
lyGlyLysAsnGlyLysAsnArgArgAs-
nArgLysLysLysAsnProCys
AsnAlaGluPheGlnAsnPheCysIle-
HisGlyGluCysLysTyrIleGluHisLeuGlu AlaValThr-
CysLysCysGlnGlnGluTyrPheGlyGluArg
CysGlyGluLys-Xaa$_4$, wherein Xaa$_4$ represents a sequence of four amino acid residues attached to the carboxy-terminal end of the amphiregulin protein, said additional amino acid residues enhancing the folding efficiency of said AR protein.

9. The amphiregulin polypeptide of claim 8 wherein Xaa$_4$ is a sequence selected from the group consisting of Ser-Met-Lys-Thr (SEQ ID NO:29) and Asp-Leu-Leu-Ala (SEQ ID NO:28).

10. A substantially pure soluble human amphiregulin glycoprotein having the following properties:

(a) an epidermal growth factor receptor binding domain comprising six cysteine residues;

(b) a heparin binding domain comprising the amino acid sequence: LysProLysArgLysLysLysGlyGlyLys (SEQ ID NO:27);

(c) a molecular weight of about 35 to 40 kD; and (d) the human sequence depicted in FIG. 2 from amino acid residue number 27 to 184 (SEQ ID NO:34).

11. A substantially pure human amphiregulin transmembrane glycoprotein having the following properties:

(a) an epidermal growth factor receptor binding domain comprising six cysteine residues;

(b) a heparin binding domain comprising the amino acid sequence: LysProLysArgLysLysLysGlyGlyLys (SEQ ID NO:27);

(c) a molecular weight of about 45 kD; and (d) the human sequence depicted in FIG. 2 from amino acid residue number 27 to 252 (SEQ ID NO:35).

12. A substantially pure human amphiregulin transmembrane glycoprotein having the following properties:

(a) an epidermal growth factor receptor binding domain comprising six cysteine residues;

(b) a heparin binding domain comprising the amino acid sequence: LysProLysArgLysLysLysGlyGlyLys (SEQ ID NO:27);

(c) a molecular weight of about 26 kD; and (d) the human sequence depicted in FIG. 2 selected from the group consisting of: (i) the amino acid sequence from amino acid 101 to 252 (SEQ ID NO:36); and (ii) the amino acid sequence from amino acid 107 to 252 (SEQ ID NO:37).

* * * * *